US010487110B2

(12) United States Patent
Verdine et al.

(10) Patent No.: US 10,487,110 B2
(45) Date of Patent: *Nov. 26, 2019

(54) STABILIZED COMPOUNDS HAVING SECONDARY STRUCTURE MOTIFS

(71) Applicant: President and Fellows of Harvard College, Cambridge, MA (US)

(72) Inventors: Gregory L. Verdine, Boston, MA (US); Christian E. Schafmeister, Somerville, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/917,560

(22) Filed: Mar. 9, 2018

(65) Prior Publication Data
US 2018/0305400 A1 Oct. 25, 2018

Related U.S. Application Data

(63) Continuation of application No. 15/287,513, filed on Oct. 6, 2016, now Pat. No. 9,951,099, which is a
(Continued)

(51) Int. Cl.
*C07K 1/04* (2006.01)
*C07K 14/47* (2006.01)
(Continued)

(52) U.S. Cl.
CPC .............. *C07K 1/00* (2013.01); *A61K 38/02* (2013.01); *C07K 1/04* (2013.01); *C07K 1/047* (2013.01);
(Continued)

(58) Field of Classification Search
CPC ........ A61K 38/02; A61K 38/03; C07K 1/047; C07K 2/00; C07K 4/12; C07K 14/746
See application file for complete search history.

(56) References Cited

U.S. PATENT DOCUMENTS 7,083,983 B2 8/2006 Lane et al.
7,084,244 B2 8/2006 Gilon et al.
(Continued)

FOREIGN PATENT DOCUMENTS

AU 2008232709 A1 10/2008
EP 467699 A2 1/1992
(Continued)

OTHER PUBLICATIONS

Extended European Search Report for EP 10800148.8, dated Oct. 16, 2013.
(Continued)

*Primary Examiner* — Jeffrey E. Russel
(74) *Attorney, Agent, or Firm* — Wolf, Greenfield & Sacks, P.C.

(57) ABSTRACT

The present invention provides novel stabilized crosslinked compounds having secondary structure motifs, libraries of these novel compounds, and methods for the synthesis of these compounds libraries thereof. The synthesis of these novel stabilized compounds involves (1) synthesizing a peptide from a selected number of natural or non-natural amino acids, wherein the peptide comprises at least two moieties capable of undergoing reaction to promote carbon-carbon bond formation; and (2) contacting the peptide with a reagent to generate at least one crosslinker and to effect stabilization of a secondary structure motif. The present invention, in a preferred embodiment, provides stabilized p53 donor helical peptides. Additionally, the present invention provides methods for disrupting the p53/MDM2 binding interaction comprising (1) providing a crosslinked stabilized α-helical structure; and (2) contacting the crosslinked stabilized α-helical structure with MDM2.

18 Claims, 22 Drawing Sheets

Specification includes a Sequence Listing.

Related U.S. Application Data continuation of application No. 14/068,844, filed on Oct. 31, 2013, now Pat. No. 9,505,801, which is a continuation of application No. 13/680,905, filed on Nov. 19, 2012, now Pat. No. 8,895,699, which is a continuation of application No. 12/796,212, filed on Jun. 8, 2010, now Pat. No. 8,324,428, which is a continuation of application No. 11/148,976, filed on Jun. 9, 2005, now Pat. No. 7,786,072, which is a continuation of application No. 09/574,086, filed on May 18, 2000, now Pat. No. 7,192,713.

(60) Provisional application No. 60/167,634, filed on Nov. 26, 1999, provisional application No. 60/134,708, filed on May 18, 1999.

(51) Int. Cl.
| | | |
|---|---|---|
| *C07K 1/00* | (2006.01) | |
| *A61K 38/02* | (2006.01) | |
| *C07K 1/113* | (2006.01) | |
| *C07K 14/00* | (2006.01) | |
| *C07K 1/10* | (2006.01) | |
| *C12N 15/10* | (2006.01) | |
| *A61K 38/00* | (2006.01) | |

(52) U.S. Cl.
CPC .............. *C07K 1/10* (2013.01); *C07K 1/113* (2013.01); *C07K 14/001* (2013.01); *C07K 14/4746* (2013.01); *C12N 15/1093* (2013.01); *A61K 38/00* (2013.01)

(56) References Cited

U.S. PATENT DOCUMENTS

| | | |
|---|---|---|
| 7,183,059 B2 | 2/2007 | Verdine et al. |
| 7,192,713 B1 | 3/2007 | Verdine et al. |
| 7,202,332 B2 | 4/2007 | Arora et al. |
| 7,247,700 B2 | 7/2007 | Korsmeyer et al. |
| 7,538,190 B2 | 5/2009 | Robinson et al. |
| 7,705,118 B2 | 4/2010 | Arora et al. |
| 7,723,469 B2 | 5/2010 | Walensky et al. |
| 7,745,573 B2 | 6/2010 | Robinson et al. |
| 7,786,072 B2 | 8/2010 | Verdine et al. |
| 8,198,405 B2 | 6/2012 | Walensky et al. |
| 8,324,428 B2 | 12/2012 | Verdine et al. |
| 8,592,377 B2 | 11/2013 | Verdine et al. |
| 8,796,418 B2 | 8/2014 | Walensky et al. |
| 8,889,632 B2 | 11/2014 | Bernal et al. |
| 8,895,699 B2 | 11/2014 | Verdine et al. |
| 8,957,026 B2 | 2/2015 | Verdine et al. |
| 9,074,009 B2 | 7/2015 | Bradner et al. |
| 9,163,330 B2 | 10/2015 | Verdine et al. |
| 9,273,099 B2 | 3/2016 | Walensky et al. |
| 9,458,189 B2 | 10/2016 | Verdine et al. |
| 9,464,115 B2 | 10/2016 | Walensky et al. |
| 9,487,562 B2 | 11/2016 | Moellering et al. |
| 9,505,801 B2 | 11/2016 | Verdine et al. |
| 9,556,227 B2 | 1/2017 | Verdine et al. |
| 9,617,309 B2 | 4/2017 | Verdine et al. |
| 9,951,099 B2 | 4/2018 | Verdine et al. |
| 10,030,049 B2 | 7/2018 | Nash et al. |
| 2004/0023887 A1 | 2/2004 | Pillutla et al. |
| 2004/0038901 A1 | 2/2004 | Basler et al. |
| 2004/0067503 A1 | 4/2004 | Tan et al. |
| 2004/0171809 A1 | 9/2004 | Korsmeyer et al. |
| 2005/0250680 A1 | 11/2005 | Walensky et al. |
| 2006/0008848 A1 | 1/2006 | Verdine et al. |
| 2006/0014675 A1 | 1/2006 | Arora et al. |
| 2006/0148715 A1 | 7/2006 | Tweardy |
| 2008/0262200 A1 | 10/2008 | Nash |
| 2009/0047711 A1 | 2/2009 | Nash |
| 2009/0088553 A1 | 4/2009 | Nash |
| 2009/0149630 A1 | 6/2009 | Walensky et al. |
| 2009/0176964 A1 | 7/2009 | Walensky et al. |
| 2009/0326192 A1 | 12/2009 | Nash et al. |
| 2010/0081611 A1 | 4/2010 | Bradner et al. |
| 2010/0168388 A1 | 7/2010 | Bernal et al. |
| 2010/0184628 A1 | 7/2010 | Nash |
| 2010/0184645 A1 | 7/2010 | Verdine et al. |
| 2010/0216688 A1 | 8/2010 | Nash et al. |
| 2010/0234563 A1 | 9/2010 | Arora et al. |
| 2010/0298201 A1 | 11/2010 | Nash et al. |
| 2011/0028753 A1 | 2/2011 | Verdine et al. |
| 2011/0144303 A1 | 6/2011 | Nash et al. |
| 2011/0144306 A1 | 6/2011 | Verdine et al. |
| 2011/0223149 A1 | 9/2011 | Nash et al. |
| 2011/0263815 A1 | 10/2011 | Nash |
| 2012/0082636 A1 | 4/2012 | Walensky et al. |
| 2012/0172311 A1 | 7/2012 | Nash et al. |
| 2012/0190818 A1 | 7/2012 | Nash |
| 2012/0270800 A1 | 10/2012 | Verdine et al. |
| 2013/0005943 A1 | 1/2013 | Arora et al. |
| 2013/0023646 A1 | 1/2013 | Nash et al. |
| 2013/0177979 A1 | 7/2013 | Turkson |
| 2013/0211046 A1 | 8/2013 | Verdine et al. |
| 2014/0005118 A1 | 1/2014 | Verdine et al. |
| 2014/0011979 A1 | 1/2014 | Verdine et al. |
| 2014/0162339 A1 | 6/2014 | Verdine et al. |
| 2014/0235549 A1 | 8/2014 | Moellering et al. |
| 2014/0256912 A1 | 9/2014 | Moellering et al. |
| 2014/0296160 A1 | 10/2014 | Walensky et al. |
| 2014/0323701 A1 | 10/2014 | Nash et al. |
| 2015/0225471 A1 | 8/2015 | Liang |
| 2015/0239937 A1 | 8/2015 | Verdine et al. |
| 2015/0284437 A1 | 10/2015 | Verdine et al. |
| 2015/0376227 A1 | 12/2015 | Verdine et al. |
| 2016/0024153 A1 | 1/2016 | Verdine et al. |
| 2016/0122405 A1 | 5/2016 | Palchaudhuri et al. |
| 2016/0215036 A1 | 7/2016 | Verdine et al. |
| 2016/0244494 A1 | 8/2016 | Verdine et al. |
| 2016/0257725 A1 | 9/2016 | Verdine et al. |
| 2017/0066799 A1 | 3/2017 | Verdine et al. |
| 2017/0088581 A1 | 3/2017 | Verdine et al. |
| 2018/0100001 A1 | 4/2018 | Verdine et al. |

FOREIGN PATENT DOCUMENTS

| | | |
|---|---|---|
| EP | 729972 A1 | 9/1996 |
| JP | 2010-510236 A | 4/2010 |
| WO | WO 89/009233 A1 | 10/1989 |
| WO | WO 93/001203 A1 | 1/1993 |
| WO | WO 94/025482 A1 | 11/1994 |
| WO | WO 95/000534 A1 | 1/1995 |
| WO | WO 96/02642 A1 | 2/1996 |
| WO | WO 96/20951 A1 | 7/1996 |
| WO | WO 96/028449 A1 | 9/1996 |
| WO | WO 96/34878 A1 | 11/1996 |
| WO | WO 97/000267 A1 | 1/1997 |
| WO | WO 97/13537 A1 | 4/1997 |
| WO | WO 97/26002 A1 | 7/1997 |
| WO | WO 97/030072 A1 | 8/1997 |
| WO | WO 97/37705 A1 | 10/1997 |
| WO | WO 98/01467 A2 | 1/1998 |
| WO | WO 98/046631 A1 | 10/1998 |
| WO | WO 98/51707 A1 | 11/1998 |
| WO | WO 99/14259 A1 | 3/1999 |
| WO | WO 99/34833 A1 | 7/1999 |
| WO | WO 99/34850 A1 | 7/1999 |
| WO | WO 00/06187 A2 | 2/2000 |
| WO | WO 02/064790 A2 | 8/2002 |
| WO | WO 2003/106491 A2 | 12/2003 |
| WO | WO 2003/106491 A3 | 12/2003 |
| WO | WO 2004/041275 A1 | 5/2004 |
| WO | WO 2004/058804 A1 | 7/2004 |
| WO | WO 2005/040202 A2 | 5/2005 |
| WO | WO 2005/040202 A3 | 5/2005 |
| WO | WO 2005/044839 A2 | 5/2005 |
| WO | WO 2005/044839 A3 | 5/2005 |
| WO | WO 2005/085457 A2 | 9/2005 |
| WO | WO 2005/090388 A1 | 9/2005 |
| WO | WO 2005/118620 A2 | 12/2005 |
| WO | WO 2005/118620 A3 | 12/2005 |

(56) References Cited

FOREIGN PATENT DOCUMENTS

| WO | WO 2005/118634 A2 | 12/2005 |
|----|-------------------|---------|
| WO | WO 2005/118634 A3 | 12/2005 |
| WO | WO 2006/103666 A2 | 10/2006 |
| WO | WO 2007/141533 A2 | 12/2007 |
| WO | WO 2008/061192 A2 | 5/2008 |
| WO | WO 2008/095063 A1 | 8/2008 |
| WO | WO 2008/121767 A2 | 10/2008 |
| WO | WO 2009/042237 A2 | 4/2009 |
| WO | WO 2009/126292 A2 | 10/2009 |
| WO | WO 2010/011313 A2 | 1/2010 |
| WO | WO 2010/034029 A1 | 3/2010 |
| WO | WO 2010/034034 A1 | 3/2010 |
| WO | WO 2010/068684 A2 | 6/2010 |
| WO | WO 2010/121288 A1 | 10/2010 |
| WO | WO 2011/008260 A2 | 1/2011 |
| WO | WO 2012/040459 A2 | 3/2012 |
| WO | WO 2012/065181 A2 | 5/2012 |
| WO | WO 2012/174423 A1 | 12/2012 |
| WO | WO 2014/047673 A1 | 4/2014 |
| WO | WO 2014/052647 A2 | 4/2014 |
| WO | WO 2014/055564 A1 | 4/2014 |

OTHER PUBLICATIONS

Invitation to Pay Additional Fees for PCT/US2010/001952, dated Oct. 29, 2010.
International Search Report and Written Opinion for PCT/US2010/001952, dated Feb. 2, 2011.
International Preliminary Report on Patentability for PCT/US2010/001952, dated Jan. 26, 2012.
Extended European Search Report for EP 09800675.2, dated Dec. 6, 2012.
Invitation to Pay Additional Fees for PCT/US2009/004260, dated Mar. 19, 2010.
International Search Report and Written Opinion for PCT/US2009/004260, dated Oct. 15, 2010.
International Preliminary Report on Patentability for PCT/US2009/004260, dated Feb. 3, 2011.
Extended European Search Report for EP 12159110.1, dated Jul. 20, 2012.
Extended European Search Report (Replacement Copy) for EP 12159110.1, dated Sep. 27, 2012.
International Search Report and Written Opinion for PCT/US2008/058575, dated Nov. 17, 2008.
International Preliminary Report on Patentability for PCT/US2008/058575, dated Oct. 8, 2009.
Invitation to Pay Additional Fees for PCT/US2011/052755, dated Feb. 16, 2012.
International Search Report and Written Opinion for PCT/US2011/052755, dated Apr. 25, 2012.
International Preliminary Report on Patentability for PCT/US2011/052755, dated Apr. 4, 2013.
International Search Report and Written Opinion for PCT/US2012/042738, dated Oct. 18, 2012.
International Preliminary Report on Patentability for PCT/US2012/042738, dated Jan. 3, 2014.
Invitation to Pay Additional Fees for PCT/US2013/062004, dated Jan. 2, 2014.
International Search Report and Written Opinion for PCT/US2013/062004, dated Apr. 23, 2014.
International Preliminary Report on Patentability for PCT/US2013/062004, dated Apr. 9, 2015.
International Search Report and Written Opinion for PCT/US2013/062929, dated Jan. 30, 2014.
International Preliminary Report on Patentability for PCT/US2013/062929, dated Apr. 16, 2015.
International Search Report and Written Opinion for PCT/US2014/025544, dated Sep. 10, 2014.
International Preliminary Report on Patentability for PCT/US2014/025544, dated Sep. 24, 2015.
International Search Report and Written Opinion for PCT/US2014/058680, dated Apr. 23, 2015.
Extended European Search Report for EP 12800679.8, dated Oct. 2, 2014.
International Search Report and Written Opinion for PCT/US2012/042719, dated Nov. 1, 2012.
International Preliminary Report on Patentability for PCT/US2012/042719, dated Jan. 3, 2014.
International Search Report and Written Opinion for PCT/US2008/052580, dated May 16, 2008.
Extended European Search Report for EP 16182714.2, dated Jan. 30, 2017.
Extended European Search Report for EP 14775716.5, dated Jul. 5, 2016.
International Search Report and Written Opinion for PCT/US2014/042329, dated Nov. 24, 2014.
International Preliminary Report on Patentability for PCT/US2014/042329, dated Dec. 23, 2015.
International Search Report and Written Opinion for PCT/US2014/041338, dated Nov. 10, 2014.
International Preliminary Report on Patentability for PCT/US2014/041338, dated Dec. 17, 2015.
International Preliminary Report on Patentability for PCT/US2014/058680, dated Apr. 14, 2016.
[No Author Listed] Bladder Cancer. Merck Manuals. Aug. 21, 2014. merckmanuals.com/home/kidney_and_urinary_tract_disorders/cancers_of_the_kidney_and_genitourinary_tract/bladder_cancer.html. 2 pages.
[No Author Listed] Brain Tumors. Merck Manuals. Aug. 21, 2014. merckmanuals.com/home/brain_spinal_cord_and_nerve_disorders/tumors_of_the_nervous_system/brain_tumors.html. 9 pages.
[No Author Listed] Breast Cancer. Merck Manuals. Aug. 21, 2014. merckmanuals.com/home/womens_health_issues/breast_disorders/breast_cancer.html. 20 pages.
[No Author Listed] Colorectal Cancer. Merck Manuals. Aug. 21, 2014. merckmanuals.com/home/digestive_disorders/tumors_of_the_digestive_system/colorectal_cancer.html. 5 pages.
[No Author Listed] Designing Custom Peptides from SIGMA Genosys, p. 1. Accessed Jul. 27, 2012.
[No Author Listed] Overview of Leukemia. Merck Manuals. Aug. 20, 2014. merckmanuals.com/home/blood_disorders/leukemias/overview_of_leukemia.html?qt=Leukemia&alt=sh. 2 pages.
[No Author Listed] Prostate Cancer. Merck Manuals. Aug. 21, 2014. merckmanuals.com/home/kidney_and_urinary_tract_disorders/cancers_of_the_kidney_and_genitourinary_tract/prostate_cancer.html?qt=prostatecancer&alt=sh. 8 pages.
[No Author Listed] Wikipedia Entry, "Willgerodt Rearrangement." Oct. 7, 2012. http://en.wikipedia.org/wiki/Willgerodt_rearrangement. [Last accessed Feb. 12, 2013].
Adhikary et al., Transcriptional regulation and transformation by Myc proteins. Nat Rev Mol Cell Biol. Aug. 2005;6(8):635-45.
Agola et al., Rab GTPases as regulators of endocytosis, targets of disease and therapeutic opportunities. Clin Genet. Oct. 2011; 80(4): 305-318.
Aman et al., cDNA cloning and characterization of the human interleukin 13 receptor alpha chain. J Biol Chem. Nov. 15, 1996;271(46):29265-70.
Andrews et al., Forming Stable Helical Peptides Using Natural and Artificial Amino Acids. Tetrahedron. 1999;55:11711-43.
Andrews et al., Kinetic analysis of the interleukin-13 receptor complex. J Biol Chem. Nov. 29, 2002;277(48):46073-8. Epub Sep. 26, 2002.
Armstrong et al., X=Y-Zh Systems as potential 1,3-dipoles. 5. Intramolecular cycloadditions of imines of a-amino acid esters. Tetrahedron. 1985;41(17):3547-58.
Artavanis-Tsakonas et al., Notch signaling: cell fate control and signal integration in development. Science. Apr. 30, 1999;284(5415):770-6.
Attisano et al., TGFbeta and Wnt pathway cross-talk. Cancer Metastasis Rev. Jan.-Jun. 2004;23(1-2):53-61.
Austin et al., A Template for Stabilization of a Peptide α-Helix: Synthesis and Evaluation of Conformational Effects by Circular Dichroism and NMR. J. Am. Chem. Soc. 1997;119:6461-72.

(56) References Cited

OTHER PUBLICATIONS

Babcock, Proteins, radicals, isotopes, and mutants in photosynthetic oxygen evolution. Proc Natl Acad Sci U S A. Dec. 1, 1993;90(23):10893-5.
Babine et al., Molecular Recognition of Proteinminus signLigand Complexes: Applications to Drug Design. Chem Rev. Aug. 5, 1997;97(5):1359-1472.
Balthaser et al., Remodelling of the natural product fumagillol employing a reaction discovery approach. Nat Chem. Dec. 2011;3(12):969-73.
Banerjee et al., Structure of a DNA glycosylase searching for lesions. Science. Feb. 24, 2006;311(5764):1153-7.
Banerjee et al., Structure of a repair enzyme interrogating undamaged DNA elucidates recognition of damaged DNA. Nature. Mar. 31, 2005;434(7033):612-8.
Bang et al., Total chemical synthesis of crambin. J Am Chem Soc. Feb. 11, 2004;126(5):1377-83.
Barker et al., Mining the Wnt pathway for cancer therapeutics. Nat Rev Drug Discov. Dec. 2006;5(12):997-1014.
Beloken et al., Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.
Belokon et al., Improved procedures for the synthesis of (S)-2-[N-(N'-benzyl-prolyl)amino]benzophenone (BPB) and Ni(II) complexes of Schiff's bases derived from BPB and amino acids. Tetrahedron: Asymmetry. 1998;9:4249-52.
Bennett et al., Regulation of osteoblastogenesis and bone mass by Wnt10b. Proc Natl Acad Sci U S A. Mar. 1, 2005;102(9):3324-9. Epub Feb. 22, 2005.
Berendsen et al., A glimpse of the Holy Grail? Science. Oct. 23, 1998;282(5389):642-3.
Berge et al., Pharmaceutical salts. J Pharm Sci. Jan. 1977;66(1):1-19.
Bernal et al., Reactivation of the p53 tumor suppressor pathway by a stapled p53 peptide. J Am Chem Soc. Mar. 7, 2007;129(9):2456-7. Epub Feb. 7, 2007.
Biagini et al., Cross-metathesis of Unsaturated α-amino Acid Derivatives. J Chem Soc Perkin Trans. 1998;1:2485-99.
Bierzynski et al., A salt bridge stabilizes the helix formed by isolated C-peptide of Rnase A. Proc Natl Acad Sci U S A. Apr. 1982;79(8):2470-4.
Blackwell et al., Highly Efficient Synthesis of Covalently Cross-Linked Peptide Helices by Ring-Closing Metathesis. Angew Chem Int Ed. 1998;37(23):3281-84.
Blackwell et al., Ring-closing metathesis of olefinic peptides: design, synthesis, and structural characterization of macrocyclic helical peptides. J Org Chem. Aug. 10, 2001;66(16):5291-302.
Blangetti et al., Suzuki-miyaura cross-coupling in acylation reactions, scope and recent developments.Molecules. Jan. 17, 2013;18(1):1188-213. doi:10.3390/molecules18011188.
Blundell et al., Atomic positions in rhombohedral 2-zinc insulin crystals. Nature. Jun. 25, 1971;231(5304):506-11.
Bode et al., Chemoselective amide ligations by decarboxylative condensations of N-alkylhydroxylamines and alpha-ketoacids. Angew Chem Int Ed Engl. Feb. 13, 2006;45(8):1248-52.
Boyden et al., High bone density due to a mutation in LDL-receptor-related protein 5. N Engl J Med. May 16, 2002;346(20):1513-21.
Bracken et al., Synthesis and Nuclear Magnetic Resonance Structure Determination of an α-Helical, Bicyclic, Lactam-Bridged Hexapeptide. J Am Chem Soc. 1994;116:6431-32.
Bradley et al., Limits of cooperativity in a structurally modular protein: response of the Notch ankyrin domain to analogous alanine substitutions in each repeat. J Mol Biol. Nov. 22, 2002;324(2):373-86.
Brandt et al., Dimeric fragment of the insulin receptor alpha-subunit binds insulin with full holoreceptor affinity. J Biol Chem. Apr. 13, 2001;276(15):12378-84. Epub Jan. 12, 2001.
Bray, Notch signalling: a simple pathway becomes complex. Nat Rev Mol Cell Biol. Sep. 2006;7(9):678-89.
Brou et al., A novel proteolytic cleavage involved in Notch signaling: the role of the disintegrin-metalloprotease TACE. Mol Cell. Feb. 2000;5(2):207-16.
Brubaker et al., Solution structure of the interacting domains of the Mad-Sin3 complex: implications for recruitment of a chromatin-modifying complex. Cell. Nov. 10, 2000;103(4):655-65.
Brusselle et al., Allergen-induced airway inflammation and bronchial responsiveness in wild-type and interleukin-4-deficient mice. Am J Respir Cell Mol Biol. Mar. 1995;12(3):254-9.
Burger et al., Synthesis of a-(trifluoromethyl)-substituted a-amino acids. Part 7. An efficient synthesis for a-trifluoromethyl-substituted w-carboxy a-amino acids. Chemiker-Zeitung. 1990;114(3):101-04. German.
Cabezas et al., The Hydrogen Bond Mimic Approach: Solid-phase Synthesis of a Peptide Stabilized as an α-Helix with a Hydrazone Link. J. Am. Chem. Soc., 1999;121:3862-75.
Caricasole et al., The Wnt pathway, cell-cycle activation and beta-amyloid: novel therapeutic strategies in Alzheimer's disease? Trends Pharmacol Sci. May 2003;24(5):233-8.
Carlson et al., Specificity landscapes of DNA binding molecules elucidate biological function. Proc Natl Acad Sci U S A. Mar. 9, 2010;107(10):4544-9. doi: 10.1073/pnas.0914023107. Epub Feb. 22, 2010.
Chen et al., Determination of the helix and beta form of proteins in aqueous solution by circular dichroism. Biochemistry. Jul. 30, 1974;13(16):3350-9.
Chen et al., Determination of the Secondary Structures of Proteins by Circular Dichroism and Optical Rotatory Dispersion. Biochemistry. 1972;11(22):4120-31.
Chen et al., Small molecule-mediated disruption of Wnt-dependent signaling in tissue regeneration and cancer. Nat Chem Biol. Feb. 2009;5(2):100-7. Epub Jan. 4, 2009.
Cheng et al., Emerging role of RAB GTPases in cancer and human disease. Cancer Res. Apr. 1, 2005;65(7):2516-9.
Cheng et al., The RAB25 small GTPase determines aggressiveness of ovarian and breast cancers. Nat Med. Nov. 2004;10(11):1251-6. Epub Oct. 24, 2004.
Cheon et al., beta-Catenin stabilization dysregulates mesenchymal cell proliferation, motility, and invasiveness and causes aggressive fibromatosis and hyperplastic cutaneous wounds. Proc Natl Acad Sci U S A. May 14, 2002;99(10):6973-8. Epub Apr. 30, 2002.
Chia et al., Emerging roles for Rab family GTPases in human cancer. Biochim Biophys Acta. Apr. 2009;1795(2):110-6.
Chiaramonte et al., Studies of murine schistosomiasis reveal interleukin-13 blockade as a treatment for established and progressive liver fibrosis. Hepatology. Aug. 2001;34(2):273-82.
Christodoulides et al., WNT10B mutations in human obesity. Diabetologia. Apr. 2006;49(4):678-84. Epub Feb. 14, 2006.
Clark et al., Supramolecular Design by Covalent Capture. Design of a Peptide Cylinder via Hydrogen-Bond-Promoted Intermolecular Olefin Metathesis. J Am Chem Soc. 1995;117:12364-65.
Clevers, Wnt/beta-catenin signaling in development and disease. Cell. Nov. 3, 2006;127(3):469-80.
Cohn et al., Cutting Edge: IL-4-independent induction of airway hyperresponsiveness by Th2, but not Th1, cells. J Immunol. Oct. 15, 1998;161(8):3813-6.
Colaluca et al., NUMB controls p53 tumour suppressor activity. Nature. Jan. 3, 2008;451(7174):76-80. doi: 10.1038/nature06412.
Cole et al., Transcription-independent functions of MYC: regulation of translation and DNA replication. Nat Rev Mol Cell Biol. Oct. 2008;9(10):810-5. Epub Aug. 13, 2008.
Cong et al., A protein knockdown strategy to study the function of beta-catenin in tumorigenesis. BMC Mol Biol. Sep. 29, 2003;4:10.
Cossu et al., Wnt signaling and the activation of myogenesis in mammals. EMBO J. Dec. 15, 1999;18(24):6867-72.
Cox et al., Insulin receptor expression by human prostate cancers. Prostate. Jan. 1, 2009;69(1):33-40. doi: 10.1002/pros.20852.
Cusack et al., 2,4,6-Tri-isopropylbenzenesulphonyl Hydrazide: A Convenient Source of Di-imide. Tetrahedron. 1976;32:2157-62.
Danial et al., Dual role of proapoptotic BAD in insulin secretion and beta cell survival. Nat Med. Feb. 2008;14(2):144-53. doi: 10.1038/nm1717. Epub Jan. 27, 2008.

(56) References Cited

OTHER PUBLICATIONS

Darnell, Transcription factors as targets for cancer therapy. Nat Rev Cancer. Oct. 2002;2(10):740-9.
David et al., Expressed protein ligation. Method and applications. Eur J Biochem. Feb. 2004;271(4):663-77.
Dawson et al., Synthesis of proteins by native chemical ligation. Science. Nov. 4, 1994;266(5186):776-9.
De Guzman et al., Structural basis for cooperative transcription factor binding to the CBP coactivator. J Mol Biol. Feb. 3, 2006;355(5):1005-13. Epub Oct. 5, 2005.
De La O et al., Notch and Kras reprogram pancreatic acinar cells to ductal intraepithelial neoplasia. Proc Natl Acad Sci U S A. Dec. 2, 2008;105(48):18907-12. doi: 10.1073/pnas.0810111105. Epub Nov. 21, 2008.
De Meyts et al., Insulin interactions with its receptors: experimental evidence for negative cooperativity. Biochem Biophys Res Commun. Nov. 1, 1973;55(1):154-61.
De Meyts, The structural basis of insulin and insulin-like growth factor-I receptor binding and negative co-operativity, and its relevance to mitogenic versus metabolic signalling. Diabetologia. Sep. 1994;37 Suppl 2:S135-48.
De Strooper et al., A presenilin-1-dependent gamma-secretase-like protease mediates release of Notch intracellular domain. Nature. Apr. 8, 1999;398(6727):518-22.
Debinski et al., Retargeting interleukin 13 for radioimmunodetection and radioimmunotherapy of human high-grade gliomas. Clin Cancer Res. Oct. 1999;5(10 Suppl):3143s-3147s.
Del Bianco et al., Mutational and energetic studies of Notch 1 transcription complexes. J Mol Biol. Feb. 8, 2008;376(1):131-40. Epub Nov. 28, 2007.
Denmark et al., Cyclopropanation with Diazomethane and Bis(oxazoline)palladium(II) Complexes. J Org Chem. May 16, 1997;62(10):3375-3389.
Devereux et al., A comprehensive set of sequence analysis programs for the VAX. Nucleic Acids Res. Jan. 11, 1984;12(1 Pt 1):387-95.
Dombroski et al., Isolation of an active human transposable element. Science. Dec. 20, 1991;254(5039):1805-8.
Doron et al., Probiotics: their role in the treatment and prevention of disease. Expert Rev Anti Infect Ther. 2006;4:261-75.
Dovey et al., Functional gamma-secretase inhibitors reduce beta-amyloid peptide levels in brain. J Neurochem. Jan. 2001;76(1):173-81.
Duronio, Insulin receptor is phosphorylated in response to treatment of HepG2 cells with insulin-like growth factor I. Biochem J. Aug. 15, 1990;270(1):27-32.
Eglen et al., The use of AlphaScreen technology in HTS: current status. Curr Chem Genomics. Feb. 25, 2008;1:2-10. doi: 10.2174/1875397300801010002.
Eisenmesser et al., Solution structure of interleukin-13 and insights into receptor engagement. J Mol Biol. Jun. 29, 2001;310(1):231-41.
Eliel, Stereochemistry of Carbon Compounds, McGraw-Hill, New York 1962.
Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.
Ellisen et al., TAN-1, the human homolog of the *Drosophila* notch gene, is broken by chromosomal translocations in T lymphoblastic neoplasms. Cell. Aug. 23, 1991;66(4):649-61.
Erlanson et al., Facile synthesis of cyclic peptides containing di-, tri-, tetra-, and Pentasulfides. Tetrahedron Letters. 1998;39(38):6799-6802.
Erlanson et al., The leucine zipper domain controls the orientation of AP-1 in the NFAT.AP-1.DNA complex. Chem Biol. Dec. 1996;3(12):981-91.
Evans et al., The Rise of Azide-Alkyne 1,3-Dipolar 'Click' Cycloaddition and its Application to Polymer Science and Surface Modification. Australian Journal of Chemistry. 2007;60:384-95.
Favrin et al., Two-state folding over a weak free-energy barrier. Biophys J. Sep. 2003;85(3):1457-65.

Fischbach et al., Specific biochemical inactivation of oncogenic Ras proteins by nucleoside diphosphate kinase. Cancer Res. Jul. 15, 2003;63(14):4089-94.
Fischer et al., The HIV-1 Rev activation domain is a nuclear export signal that accesses an export pathway used by specific cellular RNAs. Cell. Aug. 11, 1995;82(3):475-83.
Fisher et al., Myc/Max and other helix-loop-helix/leucine zipper proteins bend DNA toward the minor groove. Proc Natl Acad Sci U S A. Dec. 15, 1992;89(24):11779-83.
Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.
Friedman-Einat et al., Target gene identification: target specific transcriptional activation by three murine homeodomain/VP16 hybrid proteins in *Saccharomyces cerevisiae*. J Exp Zool. Feb. 15, 1996;274(3):145-56.
Friedmann et al., RAM-induced allostery facilitates assembly of a notch pathway active transcription complex. J Biol Chem. May 23, 2008;283(21):14781-91. doi: 10.1074/jbc.M709501200. Epub Apr. 1, 2008.
Fromme et al., Structural basis for removal of adenine mispaired with 8-oxoguanine by MutY adenine DNA glycosylase. Nature. Feb. 12, 2004;427(6975):652-6.
Fryer et al., Mastermind mediates chromatin-specific transcription and turnover of the Notch enhancer complex. Genes Dev. Jun. 1, 2002;16(11):1397-411.
Fuchs et al., Socializing with the neighbors: stem cells and their niche. Cell. Mar. 19, 2004;116(6):769-78.
Fung et al., Delta-like 4 induces notch signaling in macrophages: implications for inflammation. Circulation. Jun. 12, 2007;115(23):2948-56. Epub May 28, 2007.
Furstner et al., Alkyne Metathesis: Development of a Novel Molybdenum-Based Catalyst System and Its Application to the Total Synthesis of Epothilone A and C. Chem Euro J. 2001;7(24):5299-5317.
Furstner et al., Mo[N(t-Bu)(AR)]3 Complexes as Catalyst Precursors: In Situ Activation and Application to Metathesis Reactions of Alkynes and Diynes. J Am Chem Soc. 1999;121:9453-54.
Furstner et al., Nozaki—Hiyama—Kishi Reactions Catalytic in Chromium. J Am Chem Soc. 1996:118:12349-57.
Fustero et al., Asymmetric synthesis of new beta,beta-difluorinated cyclic quaternary alpha-amino acid derivatives. Org Lett. Aug. 31, 2006;8(18):4129-32.
Gallivan et al., A neutral, water-soluble olefin metathesis catalyst based on an N-heterocyclic carbene ligand. Tetrahedron Letters. 2005;46:2577-80.
Gante, Peptidomimetics—Tailored Enzyme Inhibitors. J Angew Chem Int Ed Engl. 1994;33:1699-1720.
Garg et al., Mutations in NOTCH1 cause aortic valve disease. Nature. Sep. 8, 2005;437(7056):270-4. Epub Jul. 17, 2005.
Gat et al., De Novo hair follicle morphogenesis and hair tumors in mice expressing a truncated beta-catenin in skin. Cell. Nov. 25, 1998;95(5):605-14.
Gavathiotis et al., BAX activation is initiated at a novel interaction site. Nature. Oct. 23, 2008;455(7216):1076-81.
Gentle et al., Direct production of proteins with N-terminal cysteine for site-specific conjugation. Bioconjug Chem. May-Jun. 2004;15(3):658-63.
Gerber-Lemaire et al., Glycosylation pathways as drug targets for cancer: glycosidase inhibitors. Mini Rev Med Chem. Sep. 2006;6(9):1043-52.
Giannis et al., Peptidomimetics for Receptor Ligands—Discovery, Development, and Medical Perspectives. Angew Chem Int Ed Engl. 1993;32:1244-67.
Gong et al., LDL receptor-related protein 5 (LRP5) affects bone accrual and eye development. Cell. Nov. 16, 2001;107(4):513-23.
Goodson et al., Potential Growth Antagonists. I. Hydantoins and Disubstituted Glycines. J Org Chem. 1960;25:1920-24.
Görlich et al., Transport between the cell nucleus and the cytoplasm. Annu Rev Cell Dev Biol. 1999;15:607-60.
Goudreau et al., Potent inhibitors of the hepatitis C virus NS3 protease: design and synthesis of macrocyclic substrate-based beta-strand mimics. J Org Chem. Sep. 17, 2004;69(19):6185-201.

(56) References Cited

OTHER PUBLICATIONS

Goun et al., Molecular transporters: synthesis of oligoguanidinium transporters and their application to drug delivery and real-time imaging. Chembiochem. Oct. 2006;7(10):1497-515.

Greenfield et al., Computed circular dichroism spectra for the evaluation of protein conformation. Biochemistry. Oct. 1969;8(10):4108-16.

Greenlee et al., A General Synthesis of α-vinyl-α-amino acids. Tetrahedron Letters. 1978;42:3999-4002.

Grossmann et al., Inhibition of oncogenic Wnt signaling through direct targeting of β-Proc Natl Acad Sci U S A. Oct. 30, 2012;109(44):17942-7. doi: 10.1073/pnas.1208396109. Epub Oct. 15, 2012.

Grubbs et al., Ring-Closing Metathesis and Related Processes in Organic Synthesis. Acc Chem Res. 1995;28:446-52.

Grünig et al., Requirement for IL-13 independently of IL-4 in experimental asthma. Science. Dec. 18, 1998;282(5397):2261-3.

Guinn et al., Synthesis and characterization of polyamides containing unnatural amino acids. Biopolymers. May 1995;35(5):503-12.

Guo et al., Probing the alpha-helical structural stability of stapled p53 peptides: molecular dynamics simulations and analysis. Chem Biol Drug Des. Apr. 2010;75(4):348-59. doi: 10.1111/j.1747-0285.2010.00951.x.

Gupta et al., Long-term effects of tumor necrosis factor-alpha treatment on insulin signaling pathway in HepG2 cells and HepG2 cells overexpressing constitutively active Akt/PKB. J Cell Biochem. Feb. 15, 2007;100(3):593-607.

Harper et al., Efficacy of a bivalent L1 virus-like particle vaccine in prevention of infection with human papillomavirus types 16 and 18 in young women: a randomized controlled trial. Lancet. Nov. 13-19, 2004;364(9447):1757-65.

Harris et al., Synthesis of proline-modified analogues of the neuroprotective agent glycyl-1-prolyl-glutamic acid (GPE). Tetrahedron. 2005;61:10018-35.

Hartmann et al., Dual roles of Wnt signaling during chondrogenesis in the chicken limb. Development. Jul. 2000;127(14):3141-59.

Hartmann, A Wnt canon orchestrating osteoblastogenesis. Trends Cell Biol. Mar. 2006;16(3):151-8. Epub Feb. 7, 2006.

Hellman et al., Electrophoretic mobility shift assay (EMSA) for detecting protein-nucleic acid interactions. Nat Protoc. 2007;2(8):1849-61.

Henchey et al., Contemporary strategies for the stabilization of peptides in the α-helical conformation. Curr Opin Chem Biol. 2008;12:692-97.

Hilton et al., Notch signaling maintains bone marrow mesenchymal progenitors by suppressing osteoblast differentiation. Nat Med. Mar. 2008;14(3):306-14. doi: 10.1038/nm1716. Epub Feb. 24, 2008.

Hipfner et al., Connecting proliferation and apoptosis in development and disease. Nat Rev Mol Cell Biol. Oct. 2004;5(10):805-15.

Hoang et al., Dickkopf 3 inhibits invasion and motility of Saos-2 osteosarcoma cells by modulating the Wnt-beta-catenin pathway. Cancer Res. Apr. 15, 2004;64(8):2734-9.

Holford et al., Adding 'splice' to protein engineering. Structure. Aug. 15, 1998;6(8):951-6.

Huang et al., How insulin binds: the B-chain alpha-helix contacts the L1 beta-helix of the insulin receptor. J Mol Biol. Aug. 6, 2004;341(2):529-50.

Huang et al., Tankyrase inhibition stabilizes axin and antagonizes Wnt signalling. Nature. Oct. 1, 2009;461(7264):614-20. Epub Sep. 16, 2009.

Jackson et al., General Approach to the Synthesis of Short α-Helical Peptides. J Am Chem Soc. 1991;113:9391-92.

Jamieson et al., Granulocyte-macrophage progenitors as candidate leukemic stem cells in blast-crisis CML. N Engl J Med. Aug. 12, 2004;351(7):657-67.

Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.

Jordan et al., Wnt4 overexpression disrupts normal testicular vasculature and inhibits testosterone synthesis by repressing steroidogenic factor 1/beta-catenin synergy. Proc Natl Acad Sci U S A. Sep. 16, 2003;100(19):10866-71. Epub Aug. 29, 2003.

Joutel et al., Notch3 mutations in CADASIL, a hereditary adult-onset condition causing stroke and dementia. Nature. Oct. 24, 1996;383(6602):707-10.

Junutula et al., Molecular characterization of Rab11 interactions with members of the family of Rab11-interacting proteins. J Biol Chem. Aug. 6, 2004;279(32):33430-7. Epub Jun. 1, 2004.

Karle et al., Structural characteristics of alpha-helical peptide molecules containing Aib residues. Biochemistry. Jul. 24, 1990;29(29):6747-56.

Karle, Flexibility in peptide molecules and restraints imposed by hydrogen bonds, the Aib residue, and core inserts. Biopolymers. 1996;40(1):157-80.

Karwoski et al., Lysinonorleucine cross-link formation in alpha amino heptenoic acid-substituted peptide derivatives. Biopolymers. 1978;17(5):1119-27.

Katoh et al., Cross-talk of WNT and FGF signaling pathways at GSK3beta to regulate beta-catenin and SNAIL signaling cascades. Cancer Biol Ther. Sep. 2006;5(9):1059-64. Epub Sep. 4, 2006.

Katsu et al., The human frizzled-3 (FZD3) gene on chromosome 8p21, a receptor gene for Wnt ligands, is associated with the susceptibility to schizophrenia. Neurosci Lett. Dec. 15, 2003;353(1):53-6.

Kaul et al., Stereochemical control of peptide folding. Bioorg Med Chem. Jan. 1999;7(1):105-17.

Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846 last accessed Apr. 9, 2012. Abstract only. 2 pages.

Kazmaier, Sythesis of Quaternary Amino Acids Containing β, γ—as well as γ,δ-Unsaturated Side Chains via Chelate-Enolate Claisen Rearrangement. Tetrahedron Letters. 1996;37(30):5351-4.

Kelly-Welch et al., Interleukin-4 and Interleukin-13 Signaling Connections Maps. Science. 2003;300:1527-28.

Khalil et al., An efficient and high yield method for the N-tert-butoxycarbonyl protection of sterically hindered amino acids. Tetrahedron Lett. 1996;37(20):3441-44.

Kim et al., Introduction of all-hydrocarbon i,i+3 staples into alpha-helices via ring-closing olefin metathesis. Org Lett. Jul. 2, 2010;12(13):3046-9. doi: 10.1021/o11010449.

Kim et al., Stereochemical effects of all-hydrocarbon tethers in i,i+4 stapled peptides. Bioorg Med Chem Lett. May 1, 2009;19(9):2533-6. Epub Mar. 13, 2009.

Kim et al., Synthesis of all-hydrocarbon stapled α-helical peptides by ring-closing olefin metathesis. Nat Protoc. Jun. 2011;6(6):761-71. doi: 10.1038/nprot.2011.324. Epub May 12, 2011.

Kimmerlin et al., '100 years of peptide synthesis': ligation methods for peptide and protein synthesis with applications to beta-peptide assemblies. J Pept Res. Feb. 2005;65(2):229-60.

Kinage et al., Highly regio-selective synthesis of beta-amino alcohol by reaction with aniline and propylene carbonate in self solvent systems over large pore zeolite catalyst. Green and Sustainable Chem. Aug. 2011;1: 76-84.

Kinzler et al., Identification of FAP locus genes from chromosome 5q21. Science. Aug. 9, 1991;253(5020):661-5.

Knackmuss et al., Specific inhibition of interleukin-13 activity by a recombinant human single-chain immunoglobulin domain directed against the IL-13 receptor alpha1 chain. Biol Chem. Mar. 2007;388(3):325-30.

Kohler et al., DNA specificity enhanced by sequential binding of protein monomers. Proc Natl Acad Sci U S A. Oct. 12, 1999;96(21):11735-9.

Kolb et al., Click Chemistry: Diverse Chemical Function from a Few Good Reactions. Angew Chem Int Ed Engl. Jun. 1, 2001;40(11):2004-2021.

Kondo et al., Frizzled 4 gene (FZD4) mutations in patients with familial exudative vitreoretinopathy with variable expressivity. Br J Ophthalmol. Oct. 2003;87(10):1291-5.

(56) References Cited

OTHER PUBLICATIONS

Konishi et al., Gamma-secretase inhibitor prevents Notch3 activation and reduces proliferation in human lung cancers. Cancer Res. Sep. 1, 2007;67(17):8051-7.
Korcsmáros et al., Uniformly curated signaling pathways reveal tissue-specific cross-talks and support drug target discovery. Bioinformatics. Aug. 15, 2010;26(16):2042-50. Epub Jun. 11, 2010.
Korinek et al., Depletion of epithelial stem-cell compartments in the small intestine of mice lacking Tcf-4. Nat Genet. Aug. 1998;19(4):379-83.
Kotha et al., Modification of constrained peptides by ring-closing metathesis reaction. Bioorg Med Chem Lett. Jun. 4, 2001;11(11):1421-3.
Kouzarides, Acetylation: a regulatory modification to rival phosphorylation? EMBO J. Mar. 15, 2000;19(6):1176-9.
Kovall et al., Crystal structure of the nuclear effector of Notch signaling, CSL, bound to DNA. EMBO J. Sep. 1, 2004;23(17):3441-51. Epub Aug. 5, 2004.
Kozlovsky et al., GSK-3 and the neurodevelopmental hypothesis of schizophrenia. Eur Neuropsychopharmacol. Feb. 2002;12(1):13-25.
Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.
Kristensen et al., Functional reconstitution of insulin receptor binding site from non-binding receptor fragments. J Biol Chem. May 24, 2002;277(21):18340-5. Epub Mar. 18, 2002.
Kurose et al., Cross-linking of a B25 azidophenylalanine insulin derivative to the carboxyl-terminal region of the alpha-subunit of the insulin receptor. Identification of a new insulin-binding domain in the insulin receptor. J Biol Chem. Nov. 18, 1994;269(46):29190-7.
Kussie et al., Structure of the MDM2 oncoprotein bound to the p53 tumor suppressor transactivation domain. Science. Nov. 8, 1996;274(5289):948-53.
Kutchukian et al., All-atom model for stabilization of alpha-helical structure in peptides by hydrocarbon staples. J Am Chem Soc. Apr. 8, 2009;131(13):4622-7.
Lacombe et al., Reduction of Olefins on Solid Support Using Diimide. Tetranderon Lett. 1998;39:6785-86.
Lammi et al., Mutations in AXIN2 cause familial tooth agenesis and predispose to colorectal cancer. Am J Hum Genet. May 2004;74(5):1043-50. Epub Mar. 23, 2004.
Laporte et al., Molecular and structural basis of cytokine receptor pleiotropy in the interleukin-4/13 system. Cell. Jan. 25, 2008;132(2):259-72.
Le Geuzennec et al., Molecular characterization of Sin3 PAH-domain interactor specificity and identification of PAH partners. Nucleic Acids Res. 2006;34(14):3929-37. Epub Aug. 12, 2006.
Le Geuzennec et al., Molecular determinants of the interaction of Mad with the PAH2 domain of mSin3. J Biol Chem. Jun. 11, 2004;279(24):25823-9. Epub Mar. 26, 2004.
Leduc et al., Helix-stabilized cyclic peptides as selective inhibitors of steroid receptor—coactivator interactions. Proc Natl Acad Sci USA. 2003;100(20):11273-78.
Lewis et al., Apoptosis in T cell acute lymphoblastic leukemia cells after cell cycle arrest induced by pharmacological inhibition of notch signaling. Chem Biol. Feb. 2007;14(2):209-19.
Li et al., Alagille syndrome is caused by mutations in human Jagged1, which encodes a ligand for Notch1. Nat Genet. Jul. 1997;16(3):243-51.
Li et al., Modulation of Notch signaling by antibodies specific for the extracellular negative regulatory region of NOTCH3. J Biol Chem. Mar. 21, 2008;283(12):8046-54. doi: 10.1074/jbc.M800170200. Epub Jan. 8, 2008.
Li et al., Notch3 signaling promotes the development of pulmonary arterial hypertension. Nat Med. Nov. 2009;15(11):1289-97. doi: 10.1038/nm.2021. Epub Oct. 25, 2009.
Liang et al., Wnt5a inhibits B cell proliferation and functions as a tumor suppressor in hematopoietic tissue. Cancer Cell. Nov. 2003;4(5):349-60.
Lindsay et al., Rab coupling protein (RCP), a novel Rab4 and Rab11 effector protein. J Biol Chem. Apr. 5, 2002;277(14):12190-9. Epub Jan. 10, 2002.
Liskamp, Conformationally restricted amino acids and dipeptides, (non)peptidomimetics and secondary structure mimetics. Recl Travl Chim Pays-Bas. 1994;113:1-19.
Little et al., A Mutation in the LDL Receptor-Related Protein 5 Gene Results in the Autosomal Dominant High-Bone-Mass Trait. Am J Hum Genet. 2002;70:11-19.
Liu et al., Chemical Ligation Approach to Form a Peptide Bond between Unprotected Peptide Segments. Concept and Model Study. J Am Chem Soc. 1994;116(10):4149-53.
Liu et al., Targeted degradation of beta-catenin by chimeric F-box fusion proteins. Biochem Biophys Res Commun. Jan. 23, 2004;313(4):1023-9.
Lo et al., Phosphorylation by the beta-catenin/MAPK complex promotes 14-3-3-mediated nuclear export of TCF/POP-1 in signal-responsive cells in C. elegans. Cell. Apr. 2, 2004;117(1):95-106.
Logan et al., The Wnt signaling pathway in development and disease. Annu Rev Cell Dev Biol. 2004;20:781-810.
Lomar et al., Synthese symmetrischerf ketone unter verwendung von 2-Phenyl-2-oxazolin-5-on. Chemische Berichte. 1980;113(12):3706-15.
Losey et al., Crystal structure of *Staphylococcus aureus* tRNA adenosine deaminase TadA in complex with RNA. Nat Struct Mol Biol. Feb. 2006;13(2):153-9. Epub Jan. 15, 2006.
Lou et al., The first three domains of the insulin receptor differ structurally from the insulin-like growth factor 1 receptor in the regions governing ligand specificity. Proc Natl Acad Sci U S A. Aug. 15, 2006;103(33):12429-34. Epub Aug. 7, 2006.
Loughlin et al., Functional variants within the secreted frizzled-related protein 3 gene are associated with hip osteoarthritis in females. Proc Natl Acad Sci U S A. Jun. 29, 2004;101(26):9757-62. Epub Jun. 21, 2004.
Lu et al., Both Pbxl and E2A-Pbx1 bind the DNA motif ATCAATCAA cooperatively with the products of multiple murine Hox genes, some of which are themselves oncogenes. Mol Cell Biol. Jul. 1995;15(7):3786-95.
Lu et al., Structural determinants within Pbx1 that mediate cooperative DNA binding with pentapeptide-containing Hox proteins: proposal for a model of a Pbxl-Hox-DNA complex. Mol Cell Biol. Apr. 1996;16(4):1632-40.
Lubman et al., Quantitative dissection of the Notch:CSL interaction: insights into the Notch-mediated transcriptional switch. J Mol Biol. Jan. 19, 2007;365(3):577-89. Epub Oct. 3, 2006.
Luo et al., Wnt signaling and human diseases: what are the therapeutic implications? Lab Invest. Feb. 2007;87(2):97-103. Epub Jan. 8, 2007.
Luscher et al., The basic region/helix-loop-helix/leucine zipper domain of Myc proto-oncoproteins: function and regulation. Oncogene. May 13, 1999;18(19):2955-66.
Luu et al., Wnt/beta-catenin signaling pathway as a novel cancer drug target. Curr Cancer Drug Targets. Dec. 2004;4(8):653-71.
Lyu et al., "α-Helix Stabilization by Natural and Unnatural Amino Acids with Alkyl Side Chains," Proc. Nat'l Acad. Sci. USA 88:5317-5320 (1991).
Macmillan, Evolving strategies for protein synthesis converge on native chemical ligation. Angew Chem Int Ed Engl. Nov. 27, 2006;45(46):7668-72.
Marshall et al., Back to the future: ribonuclease A. Biopolymers. 2008;90(3):259-77.
McKern et al., Structure of the insulin receptor ectodomain reveals a folded-over conformation. Nature. Sep. 14, 2006;443(7108):218-21. Epub Sep. 6, 2006.
McNamara et al., Peptides constrained by an aliphatic linkage between two C(alpha) sites: design, synthesis, and unexpected conformational properties of an i,(i + 4)-linked peptide. J Org Chem. Jun. 29, 2001;66(13):4585-94.
Mellegaardwaetzig et al., Allylic amination via decarboxylative c—n bond formation. Synlett. 2005;18:2759-2762.

(56) References Cited

OTHER PUBLICATIONS

Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.
Menting et al., How insulin engages its primary binding site on the insulin receptor. Nature. Jan. 10, 2013;493(7431):241-5. doi: 10.1038/nature11781.
Meyers et al., Formation of mutually exclusive Rab11 complexes with members of the family of Rab11-interacting proteins regulates Rab11 endocytic targeting and function. J Biol Chem. Dec. 13, 2002;277(50):49003-10. Epub Oct. 9, 2002.
Miller et al., Application of Ring-Closing Metathesis to the Synthesis of Rigidified Amino Acids and Peptides. J Am Chem Soc. 1996;118(40):9606-9614.
Miller et al., Synthesis of Conformationally Restricted Amino Acids and Peptides Employing Olefin Metathesis. J Am Chem Soc. 1995;117(21):5855-5856.
Miloux et al., Cloning of the human IL-13R alpha1 chain and reconstitution with the IL4R alpha of a functional IL-4/IL-13 receptor complex. FEBS Lett. Jan. 20, 1997;401(2-3):163-6.
Miyaoka et al., Increased expression of Wnt-1 in schizophrenic brains. Schizophr Res. Jul. 27, 1999;38(1):1-6.
Moellering et al., Computational modeling and molecular optimization of stabilized alpha-helical peptides targeting NOTCH-CSL transcriptional complexes. European Journal of Cancer Supplements Nov. 2010; 8(7):30. DOI: 10.1016/S1359-6349(10)71774-2. Abstract 69.
Moellering et al., Direct inhibition of the NOTCH transcription factor complex. Nature. Nov. 12, 2009;462(7270):182-8.
Moon et al., WNT and beta-catenin signalling: diseases and therapies. Nat Rev Genet. Sep. 2004;5(9):689-99.
Morin, beta-catenin signaling and cancer. Bioessays. Dec. 1999;21(12):1021-30.
Moses et al., The growing applications of click chemistry. Chem Soc Rev. Aug. 2007;36(8):1249-62.
Moy et al., Solution structure of human IL-13 and implication for receptor binding. J Mol Biol. Jun. 29, 2001;310(1):219-30.
Mudher et al., Alzheimer's disease-do tauists and baptists finally shake hands? Trends Neurosci. Jan. 2002;25(1):22-6.
Muir et al., Expressed protein ligation: a general method for protein engineering. Proc Natl Acad Sci U S A. Jun. 9, 1998;95(12):6705-10.
Muir, Semisynthesis of proteins by expressed protein ligation. Annu Rev Biochem. 2003;72:249-89. Epub Feb. 27, 2003.
Muppidi et al., Conjugation of spermine enhances cellular uptake of the stapled peptide-based inhibitors of p53-Mdm2 interaction. Bioorg Med Chem Lett. Dec. 15, 2011;21(24):7412-5. doi: 10.1016/j.bmcl.2011.10.009. Epub Oct. 12, 2011.
Mynarcik et al., Alanine-scanning mutagenesis of a C-terminal ligand binding domain of the insulin receptor alpha subunit. J Biol Chem. Feb. 2, 1996;271(5):2439-42.
Mynarcik et al., Identification of common ligand binding determinants of the insulin and insulin-like growth factor 1 receptors. Insights into mechanisms of ligand binding. J Biol Chem. Jul. 25, 1997;272(30):18650-5.
Myung et al., The ubiquitin-proteasome pathway and proteasome inhibitors. Med Res Rev. Jul. 2001;21(4):245-73.
Nair et al., X-ray structures of Myc-Max and Mad-Max recognizing DNA. Molecular bases of regulation by proto-oncogenic transcription factors. Cell. Jan. 24, 2003;112(2):193-205.
Nakashima et al., Cross-talk between Wnt and bone morphogenetic protein 2 (BMP-2) signaling in differentiation pathway of C2C12 myoblasts. J Biol Chem. Nov. 11, 2005;280(45):37660-8. Epub Sep. 2, 2005.
Nam et al., Structural basis for cooperativity in recruitment of MAML coactivators to Notch transcription complexes. Cell. Mar. 10, 2006;124(5):973-83.
Nam et al., Structural requirements for assembly of the CSL.intracellular Notch1.Mastermind-like 1 transcriptional activation complex. J Biol Chem. Jun. 6, 2003;278(23):21232-9. Epub Mar. 18, 2003.
Narhi et al., Role of native disulfide bonds in the structure and activity of insulin-like growth factor 1: genetic models of protein-folding intermediates. Biochemistry. May 18, 1993;32(19):5214-21.
Nefedova et al., Involvement of Notch-1 signaling in bone marrow stroma-mediated de novo drug resistance of myeloma and other malignant lymphoid cell lines. Blood. May 1, 2004;103(9):3503-10. Epub Dec. 11, 2003.
Ngo et al., Computational complexity, protein structure prediction, and the levinthal paradox. In: The Protein Folding Problem and Tertiary Structure Prediction. K. Mem, Jr., et al. Eds. 1994:433-506.
Niemann et al., Homozygous WNT3 mutation causes tetra-amelia in a large consanguineous family. Am J Hum Genet. Mar. 2004;74(3):558-63. Epub Feb. 5, 2004.
Nilsson et al., Staudinger ligation: a peptide from a thioester and azide. Org Lett. Jun. 29, 2000;2(13):1939-41.
Niranjan et al., The Notch pathway in podocytes plays a role in the development of glomerular disease. Nat Med. Mar. 2008;14(3):290-8. doi: 10.1038/nm1731. Epub Mar. 2, 2008.
Nishisho et al., Mutations of chromosome 5q21 genes in FAP and colorectal cancer patients. Science. Aug. 9, 1991;253(5020):665-9.
Noguera-Troise et al., Blockade of Dll4 inhibits tumour growth by promoting non-productive angiogenesis. Nature. Dec. 21, 2006;444(7122):1032-7.
Okamura et al., Redundant regulation of T cell differentiation and TCRalpha gene expression by the transcription factors LEF-1 and TCF-1. Immunity. Jan. 1998;8(1):11-20.
Olson et al., Sizing up the heart: development redux in disease. Genes Dev. Aug. 15, 2003;17(16):1937-56. Epub Jul. 31, 2003.
O'Neil et al., A Thermodynamic Scale for the Helix-forming Tendencies of the Commonly Occurring Amino Acids. Science 1990;250:646-51.
O'Neil et al., FBW7 mutations in leukemic cells mediate NOTCH pathway activation and resistance to gamma-secretase inhibitors. J Exp Med. Aug. 6, 2007;204(8):1813-24. Epub Jul. 23, 2007.
Oswald et al., RBP-Jkappa/SHARP recruits CtIP/CtBP corepressors to silence Notch target genes. Mol Cell Biol. Dec. 2005;25(23):10379-90.
Pakotiprapha et al., Crystal structure of Bacillus stearothermophilus UvrA provides insight into ATP-modulated dimerization, UvrB interaction, and DNA binding. Mol Cell. Jan. 18, 2008;29(1):122-33. Epub Dec. 27, 2007.
Palchaudhuri et al., Differentiation induction in acute myeloid leukemia using site-specific DNA-targeting. 55th ASH Annual Meeting and Exposition. Dec. 9, 2013. Accessed at https://ash.confex.com/ash/2013/webprogram/Paper60843.html.
Palomero et al., Mutational loss of PTEN induces resistance to NOTCH1 inhibition in T-cell leukemia. Nat Med. Oct. 2007;13(10):1203-10. Epub Sep. 16, 2007.
Park et al., Notch3 gene amplification in ovarian cancer. Cancer Res. Jun. 15, 2006;66(12):6312-8.
Parrish et al., Perspectives on alkyl carbonates in organic synthesis. Tetrahedron, 2000; 56(42): 8207-8237.
Pellois et al., Semisynthetic proteins in mechanistic studies: using chemistry to go where nature can't. Curr Opin Chem Biol. Oct. 2006;10(5):487-91. Epub Aug. 28, 2006.
Phelan et al., A General Method for Constraining Short Peptides to an α-Helical Conformation. J Am Chem Soc. 1997;119(3):455-60.
Picksley et al., Immunochemical analysis of the interaction of p53 with MDM2;—fine mapping of the MDM2 binding site on p53 using synthetic peptides. Oncogene. Sep. 1994;9(9):2523-9.
Pillutla et al., Peptides identify the critical hotspots involved in the biological activation of the insulin receptor. J Biol Chem. Jun. 21, 2002;277(25):22590-4. Epub Apr. 18, 2002.
Pinnix et al., Active Notch1 confers a transformed phenotype to primary human melanocytes. Cancer Res. Jul. 1, 2009;69(13):5312-20. doi: 10.1158/0008-5472.CAN-08-3767. Epub Jun. 23, 2009.
Polakis, The oncogenic activation of beta-catenin. Curr Opin Genet Dev. Feb. 1999;9(1):15-21.

(56) References Cited

OTHER PUBLICATIONS

Qian et al., Helix-coil Theories: A Comparative Study for Finite Length Polypeptides. J. Phys. Chem. 1992;96:3987-94.
Qiu et al., Convenient, Large-Scale Asymmetric Synthesis of Enantiomerically Pure trans-Cinnamylglycine and -α-Alanine. Tetrahedron. 2000;56:2577-82.
Rao et al., Inhibition of NOTCH signaling by gamma secretase inhibitor engages the RB pathway and elicits cell cycle exit in T-cell acute lymphoblastic leukemia cells. Cancer Res. Apr. 1, 2009;69(7):3060-8. doi: 10.1158/0008-5472.CAN-08-4295. Epub Mar. 24, 2009.
Rawlinson et al., CRM1-mediated nuclear export of dengue virus RNA polymerase NS5 modulates interleukin-8 induction and virus production. J Biol Chem. Jun. 5, 2009;284(23):15589-97. Epub Mar. 18, 2009.
Reya et al., Wnt signalling in stem cells and cancer. Nature. Apr. 14, 2005;434(7035):843-50.
Rich et al., Synthesis of the cytostatic cyclic tetrapeptide, chlamydocin. Tetranderon Letts. 1983;24(48):5305-08.
Ridgway et al., Inhibition of D114 signalling inhibits tumour growth by deregulating angiogenesis. Nature. Dec. 21, 2006;444(7122):1083-7.
Robert, A hierarchical "nesting" approach to describe the stability of alpha helices with side-chain interactions. Biopolymers. 1990;30(3-4):335-47.
Robitaille et al., Mutant frizzled-4 disrupts retinal angiogenesis in familial exudative vitreoretinopathy. Nat Genet. Oct. 2002;32(2):326-30. Epub Aug. 12, 2002.
Rodova et al., The polycystic kidney disease-1 promoter is a target of the beta-catenin/T-cell factor pathway. J Biol Chem. Aug. 16, 2002;277(33):29577-83. Epub Jun. 4, 2002.
Roos et al., Synthesis of α-Substituted α-Amino Acids via Cationic Intermediates. J Org Chem. 1993;58:3259-68.
Ross et al., Inhibition of adipogenesis by Wnt signaling. Science. Aug. 11, 2000;289(5481):950-3.
Rudinger, Characteristics of the amino acids as components of a peptide hormone sequence. In: Peptide Hormones. J. A. Parsons, ed. University Park Press. Jun. 1976:1-7.
Sadot et al., Down-regulation of beta-catenin by activated p53. Mol Cell Biol. Oct. 2001;21(20):6768-81.
Sali et al., Stabilization of protein structure by interaction of alpha-helix dipole with a charged side chain. Nature. Oct. 20, 1988;335(6192):740-3.
Sampietro et al., Crystal structure of a beta-catenin/BCL9/Tcf4 complex. Mol Cell. Oct. 20, 2006;24(2):293-300.
Satoh et al., AXIN1 mutations in hepatocellular carcinomas, and growth suppression in cancer cells by virus-mediated transfer of AXIN1. Nat Genet. Mar. 2000;24(3):245-50.
Sattler et al., Structure of Bcl-xL-Bak peptide complex: recognition between regulators of apoptosis. Science. Feb. 14, 1997;275(5302):983-6.
Saxon et al., Cell surface engineering by a modified Staudinger reaction. Science. Mar. 17, 2000;287(5460):2007-10.
Schäffer et al., A novel high-affinity peptide antagonist to the insulin receptor. Biochem Biophys Res Commun. Nov. 14, 2008;376(2):380-3. doi: 10.1016/j.bbrc.2008.08.151. Epub Sep. 7, 2008.
Schäffer et al., Assembly of high-affinity insulin receptor agonists and antagonists from peptide building blocks. Proc Natl Acad Sci U S A. Apr. 15, 2003;100(8):4435-9. Epub Apr. 8, 2003.
Schafmiester et al., An All-Hydrocarbon Cross-Linking System for Enhancing the Helicity and Metabolic Stability of Peptides. J Am Chem Soc. 2000;122:5891-92.
Scheffzek et al., The Ras-RasGAP complex: structural basis for GTPase activation and its loss in oncogenic Ras mutants. Science. Jul. 18, 1997;277(5324):333-8.
Schinzel et al., The phosphate recognition site of *Escherichia coli* maltodextrin phosphorylase. FEBS Lett. Jul. 29, 1991;286(1-2):125-8.
Schmiedeberg et al., Reversible backbone protection enables combinatorial solid-phase ring-closing metathesis reaction (RCM) in peptides. Org Lett. Jan. 10, 2002;4(1):59-62.
Scholtz et al., The mechanism of alpha-helix formation by peptides. Annu Rev Biophys Biomol Struct. 1992;21:95-118.
Schrock et al., Tungsten(VI) Neopentylidyne Complexes. Organometallics. 1982;1:1645-51.
Schwarzer et al., Protein semisynthesis and expressed protein ligation: chasing a protein's tail. Curr Opin Chem Biol. Dec. 2005;9(6):561-9. Epub Oct. 13, 2005.
Scott et al., Evidence of insulin-stimulated phosphorylation and activation of the mammalian target of rapamycin mediated by a protein kinase B signaling pathway. Proc Natl Acad Sci U S A. Jun. 23, 1998;95(13):7772-7.
Seabra et al., Rab GTPases, intracellular traffic and disease. Trends Mol Med. Jan. 2002;8(1):23-30.
Seiffert et al., Presenilin-1 and -2 are molecular targets for gamma-secretase inhibitors. J Biol Chem. Nov. 3, 2000;275(44):34086-91.
Shair, A closer view of an oncoprotein-tumor suppressor interaction. Chem Biol. Nov. 1997;4(11):791-4.
Shiba et al., Structural basis for Rab11-dependent membrane recruitment of a family of Rab11-interacting protein 3 (FIP3)/Arfophilin-1. Proc Natl Acad Sci U S A. Oct. 17, 2006;103(42):15416-21. Epub Oct. 9, 2006.
Si et al., CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Siddle et al., Specificity in ligand binding and intracellular signalling by insulin and insulin-like growth factor receptors. Biochem Soc Trans. Aug. 2001;29(Pt 4):513-25.
Singh et al., Iridium(I)-catalyzed regio- and enantioselective allylic amidation.Tet. Lett. 2007;48 (40): 7094-7098.
Skinner et al., Basic helix-loop-helix transcription factor gene family phylogenetics and nomenclature. Differentiation. Jul. 2010;80(1):1-8. doi: 10.1016/j.diff.2010.02.003. Epub Mar. 10, 2010.
Smith et al., Structural resolution of a tandem hormone-binding element in the insulin receptor and its implications for design of peptide agonists. Proc Natl Acad Sci U S A. Apr. 13, 2010;107(15):6771-6. doi: 10.1073/pnas.1001813107. Epub Mar. 26, 2010.
Soucek et al., Modelling Myc inhibition as a cancer therapy. Nature. Oct. 2, 2008;455(7213):679-83. Epub Aug. 17, 2008.
Sparey et al., Cyclic sulfamide gamma-secretase inhibitors. Bioorg Med Chem Lett. Oct. 1, 2005;15(19):4212-6.
Stein et al., Rab proteins and endocytic trafficking: potential targets for therapeutic intervention. Adv Drug Deliv Rev. Nov. 14, 2003;55(11):1421-37.
Stenmark et al., The Rab GTPase family. Genome Biol. 2001;2(5):3007.1-3007.7.
Still et al., Semianalytical Treatment of Solvation for Molecular Mechanics and Dynamics. J Am Chem Soc. 1990;112:6127-29.
Struhl et al., Presenilin is required for activity and nuclear access of Notch in *Drosophila*. Nature. Apr. 8, 1999;398(6727):522-5.
Stueanaes et al., Beta-adrenoceptor stimulation potentiates insulin-stimulated PKB phosphorylation in rat cardiomyocytes via cAMP and PKA. Br J Pharmacol. May 2010;160(1):116-29. doi: 10.1111/j.1476-5381.2010.00677.x.
Su et al., Eradication of pathogenic beta-catenin by Skp1/Cullin/F box ubiquitination machinery. Proc Natl Acad Sci U S A. Oct. 28, 2003;100(22):12729-34. Epub Oct. 16, 2003.
Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.
Takeda et al., Human sebaceous tumors harbor inactivating mutations in LEF1. Nat Med. Apr. 2006;12(4):395-7. Epub Mar. 26, 2006.
Tanaka, Design and synthesis of non-proteinogenic amino acids and secondary structures of their peptides. Yakugaku Zasshi. Oct. 2006;126(10):931-44. Japanese.

(56) References Cited

OTHER PUBLICATIONS

Thompson et al., Mutants of interleukin 13 with altered reactivity toward interleukin 13 receptors. J Biol Chem. Oct. 15, 1999;274(42):29944-50.

Thundimadathil, New Reactions with Click Chemistry. An R&D Magazine Webcast. Oct. 10, 2012. www.rdmag.com/articles/2012/10/new-reactions-click-chemistry. [Last accessed Feb. 13, 2013}.

Tian et al., Linear non-competitive inhibition of solubilized human gamma-secretase by pepstatin A methylester, L685458, sulfonamides, and benzodiazepines. J Biol Chem. Aug. 30, 2002;277(35):31499-505. Epub Jun. 18, 2002.

Tian et al., The role of the Wnt-signaling antagonist DKK1 in the development of osteolytic lesions in multiple myeloma. N Engl J Med. Dec. 25, 2003;349(26):2483-94.

Tolbert et al., New methods for proteomic research: preparation of proteins with N-terminal cysteines for labeling and conjugation. Angew Chem Int Ed Engl. Jun. 17, 2002;41(12):2171-4.

Toniolo, Conformationally restricted peptides through short-range cyclizations. Int J Pept Protein Res. Apr. 1990;35(4):287-300.

Toomes et al., Mutations in LRP5 or FZD4 underlie the common familial exudative vitreoretinopathy locus on chromosome 11q. Am J Hum Genet. Apr. 2004;74(4):721-30. Epub Mar. 11, 2004.

Tornøe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.

Torrance et al., Combinatorial chemoprevention of intestinal neoplasia. Nat Med. Sep. 2000;6(9):1024-8.

Tsuji et al., Antiproliferative activity of REIC/Dkk-3 and its significant down-regulation in non-small-cell lung carcinomas. Biochem Biophys Res Commun. Nov. 23, 2001;289(1):257-63.

Tsuji et al., Synthesis of γ, δ-unsay urated ketones by the intramolecular decarboxylative allylation of allyl β-reto carboxylates and alkenyl allyl carbonates catalyzed by molybdenum, nickel, and rhodium complexes. Chemistry Letters. 1984; 13(10):1721-1724.

Tsuruzoe et al., Insulin receptor substrate 3 (IRS-3) and IRS-4 impair IRS-1- and IRS-2-mediated signaling. Mol Cell Biol. Jan. 2001;21(1):26-38.

Ueki et al., Increased insulin sensitivity in mice lacking p85beta subunit of phosphoinositide 3-kinase. Proc Natl Acad Sci U S A. Jan. 8, 2002;99(1):419-24. Epub Dec. 18, 2001.

Ueki et al., Positive and negative regulation of phosphoinositide 3-kinase-dependent signaling pathways by three different gene products of the p85alpha regulatory subunit. Mol Cell Biol. Nov. 2000;20(21):8035-46.

Uesugi et al., The alpha-helical FXXPhiPhi motif in p53: TAF interaction and discrimination by MDM2. Proc Natl Acad Sci U S A. Dec. 21, 1999;96(26):14801-6.

Ullman et al., Luminescent oxygen channeling immunoassay: measurement of particle binding kinetics by chemiluminescence. Proc Natl Acad Sci U S A. Jun. 7, 1994;91(12):5426-30.

Vaickus et al., Immune markers in hematologic malignancies. Crit Rev Oncol Hematol. Dec. 1991;11(4):267-97.

Van Genderen et al., Development of several organs that require inductive epithelial-mesenchymal interactions is impaired in LEF-1-deficient mice. Genes Dev. Nov. 15, 1994;8(22):2691-703.

Van Gijn et al., The wnt-frizzled cascade in cardiovascular disease. Cardiovasc Res. Jul. 2002;55(1):16-24.

Varallo et al., Beta-catenin expression in Dupuytren's disease: potential role for cell-matrix interactions in modulating beta-catenin levels in vivo and in vitro. Oncogene. Jun. 12, 2003;22(24):3680-4.

Vartak et al., Allosteric Modulation of the Dopamine Receptor by Conformationally Constrained Type VI β-Turn Peptidomimetics of Pro-Leu-Gly-$NH_2$ . J Med Chem. 2007;50(26):6725-6729.

Venancio et al., Reconstructing the ubiquitin network: cross-talk with other systems and identification of novel functions. Genome Biol. 2009;10(3):R33. Epub Mar. 30, 2009.

Verdine et al., Stapled peptides for intracellular drug targets. Methods Enzymol. 2012;503:3-33. doi: 10.1016/B978-0-12-396962-0.00001-X.

Verdine et al., The challenge of drugging undruggable targets in cancer: lessons learned from targeting BCL-2 family members. Clin Cancer Res. Dec. 15, 2007;13(24):7264-70.

Verma et al., Small interfering RNAs directed against beta-catenin inhibit the in vitro and in vivo growth of colon cancer cells. Clin Cancer Res. Apr. 2003;9(4):1291-300.

Voet et al., Biochemistry. Second Edition. John Wiley & Sons, Inc. 1995:235-241.

Walensky et al., A stapled BID BH3 helix directly binds and activates BAX. Mol Cell. Oct. 20, 2006;24(2):199-210.

Walensky et al., Activation of apoptosis in vivo by a hydrocarbon-stapled BH3 helix. Science. Sep. 3, 2004;305(5689):1466-70.

Walter et al., Critical role for IL-13 in the development of allergen-induced airway hyperreactivity. J Immunol. Oct. 15, 2001;167(8):4668-75.

Wang et al., Inhibition of p53 degradation by Mdm2 acetylation. FEBS Lett. Mar. 12, 2004;561(1-3):195-201.

Wang, 4-Alkyl-2-trichloromethyloxazolidin-5-ones: Valuable Precursors to Enantiomerically Pure C- and N-Protected α-Alkyl Prolines. Synlett. 1999;1:33-36.

Weaver et al., Transition metal-catalyzed decarboxylative allylation and benzylation reactions.Chemical Rev. Mar. 9, 2011;111(3):1846-913.

Wei et al., Disorder and structure in the Rab11 binding domain of Rab11 family interacting protein 2. Biochemistry. Jan. 27, 2009;48(3):549-57. doi: 10.1021/bi8020197.

Weng et al., Activating mutations of NOTCH1 in human T cell acute lymphoblastic leukemia. Science. Oct. 8, 2004;306(5694):269-71.

Weng et al., Growth suppression of pre-T acute lymphoblastic leukemia cells by inhibition of notch signaling. Mol Cell Biol. Jan. 2003;23(2):655-64.

Westhoff et al., Alterations of the Notch pathway in lung cancer. Proc Natl Acad Sci U S A. Dec. 29, 2009;106(52):22293-8. doi: 10.1073/pnas.0907781106. Epub Dec. 10, 2009.

Wild et al., Peptides Corresponding to a Predictive α-Helical Domain of Human Immunodeficiency Virus Type 1 gp41 are Potent Inhibitors of Virus Infection. Proc. Nat'l Acad. Sci. USA 1994;91:9770-74.

Williams et al., Asymmetric synthesis of 2,6-diamino-6-(hydroxymethyl)pimelic acid: assignment of stereochemistry. J Am Chem Soc. 1991;113(18):6976-6981.

Williams et al., Asymmetric Synthesis of Monosubstituted and α,α-Disubstituted α-Amino Acids via Diastereoselective Glycine Enolate Alkylations. J Am Chem Soc. 1991;113:9276-86.

Wills-Karp et al., Interleukin-13: central mediator of allergic asthma. Science. Dec. 18, 1998;282(5397):2258-61.

Wills-Karp, Interleukin-13 in asthma pathogenesis. Immunol Rev. Dec. 2004;202:175-90.

Wills-Karp, The gene encoding interleukin-13: a susceptibility locus for asthma and related traits. Respir Res. 2000;1(1):19-23. Epub Jul. 17, 2000.

Wilson et al., Crystal structure of the CSL-Notch-Mastermind ternary complex bound to DNA. Cell. Mar. 10, 2006;124(5):985-96.

Wilson et al., The FIP3-Rab11 protein complex regulates recycling endosome targeting to the cleavage furrow during late cytokinesis. Mol Biol Cell. Feb. 2005;16(2):849-60. Epub Dec. 15, 2004.

Woon et al., Linking of 2-oxoglutarate and substrate binding sites enables potent and highly selective inhibition of JmjC histone demethylases. Angew Chem Int Ed Engl. Feb. 13, 2012;51(7):1631-4. doi: 10.1002/anie.201107833. Epub Jan. 12, 2012.

Wu et al., MAML1, a human homologue of *Drosophila* mastermind, is a transcriptional co-activator for NOTCH receptors. Nat Genet. Dec. 2000;26(4):484-9.

Wu et al., Therapeutic antibody targeting of individual Notch receptors. Nature. Apr. 15, 2010;464(7291):1052-7. doi: 10.1038/nature08878.

Xi et al., Use of DNA and peptide nucleic acid molecular beacons for detection and quantification of rRNA in solution and in whole cells. Appl Environ Microbiol. Sep. 2003;69(9):5673-8.

Xing et al., Crystal structure of a beta-catenin/axin complex suggests a mechanism for the beta-catenin destruction complex. Genes Dev. Nov. 15, 2003;17(22):2753-64. Epub Nov. 4, 2003.

(56) References Cited

OTHER PUBLICATIONS

Yang et al., Synthesis and helical structure of lactam bridged BH3 peptides derived from pro-apoptotic Bcl-2 family proteins. Bioorg Med Chem Lett. 2004;14:1403-06.
Yang et al., Therapeutic dosing with anti-interleukin-13 monoclonal antibody inhibits asthma progression in mice. J Pharmacol Exp Ther. Apr. 2005;313(1):8-15. Epub Jan. 11, 2005.
Ye et al., Neurogenic phenotypes and altered Notch processing in *Drosophila* Presenilin mutants. Nature. Apr. 8, 1999;398(6727):525-9.
Yu et al., The role of Axin2 in calvarial morphogenesis and craniosynostosis. Development. Apr. 2005;132(8):1995-2005.
Zhang et al., 310 Helix versus alpha-helix: a molecular dynamics study of conformational preferences of Aib and Alanine. J. American Cancer Society. Dec. 1994; 116(26):11915-11921.
Zhang et al., A cell-penetrating helical peptide as a potential HIV-1 inhibitor. J Mol Biol. May 2, 2008;378(3):565-80. doi: 10.1016/j.jmb.2008.02.066. Epub Mar. 6, 2008.
Zhang et al., A triazole-templated ring-closing metathesis for constructing novel fused and bridged triazoles. Chem Commun (Camb). Jun. 21, 2007;(23):2420-2.
Zhou et al., Identification of Ubiquitin Target Proteins Using Cell-Based Arrays. J Proteome Res. 2007;6:4397-4406.
Zhou et al., Lymphoid enhancer factor 1 directs hair follicle patterning and epithelial cell fate. Genes Dev. Mar. 15, 1995;9(6):700-13.
Zhou et al., Tyrosine kinase inhibitor STI-571/Gleevec down-regulates the beta-catenin signaling activity. Cancer Lett. Apr. 25, 2003;193(2):161-70.
Zimm et al., Theory of the Phase Transition between Helix and Random Coil in Polypeptide Chains. J Chem Phys. 1959;31:526-35.
Zor et al., Solution structure of the KIX domain of CBP bound to the transactivation domain of c-Myb. J Mol Biol. Mar. 26, 2004;337(3):521-34.
U.S. Appl. No. 13/383,881, filed Jan. 13, 2012, Verdine et al.
U.S. Appl. No. 14/880,080, filed Oct. 9, 2015, Verdine et al.
U.S. Appl. No. 15/789,421, filed Oct. 20, 2017, Verdine et al.
U.S. Appl. No. 13/055,279, filed Jan. 21, 2011, Verdine et al.
U.S. Appl. No. 14/748,287, filed Jun. 24, 2015, Verdine et al.
U.S. Appl. No. 12/593,384, filed Mar. 5, 2010, Verdine et al.
U.S. Appl. No. 14/027,064, filed Sep. 13, 2013, Verdine et al.
U.S. Appl. No. 15/275,118, filed Sep. 23, 2016, Verdine et al.
U.S. Appl. No. 13/825,709, filed Mar. 22, 2013, Verdine et al.
U.S. Appl. No. 14/615,235, filed Feb. 5, 2015, Verdine et al.
U.S. Appl. No. 14/126,642, filed Dec. 16, 2013, Moellering et al.
U.S. Appl. No. 14/431,280, filed Mar. 25, 2015, Verdine et al.
U.S. Appl. No. 14/432,804, filed Apr. 1, 2015, Liang et al.
U.S. Appl. No. 14/775,315, filed Sep. 11, 2015, Verdine et al.
U.S. Appl. No. 14/898,222, filed Dec. 14, 2015, Verdine et al.
U.S. Appl. No. 14/896,132, filed Dec. 4, 2015, Palchaudhuri et al.
U.S. Appl. No. 15/026,473, filed Mar. 31, 2016, Verdine et al.
U.S. Appl. No. 14/127,039, filed Dec. 17, 2013, Moellering et al.
U.S. Appl. No. 09/574,086, filed May 18, 2000, Verdine et al.
U.S. Appl. No. 11/148,976, filed Jun. 9, 2005, Verdine et al.
U.S. Appl. No. 12/796,212, filed Jun. 8, 2010, Verdine et al.
U.S. Appl. No. 13/680,905, filed Nov. 19, 2012, Verdine et al.
U.S. Appl. No. 14/068,844, filed Oct. 31, 2013, Verdine et al.
U.S. Appl. No. 15/287,513, filed Oct. 6, 2016, Verdine et al.
U.S. Appl. No. 12/420,816, filed Apr. 8, 2009, Nash et al.
U.S. Appl. No. 13/570,146, filed Aug. 8, 2012, Nash et al.
U.S. Appl. No. 14/156,350, filed Jan. 15, 2014, Nash et al.
EP 10800148.8, Oct. 16, 2013, Extended European Search Report.
PCT/US2010/001952, Oct. 29, 2010, Invitation to Pay Additional Fees.
PCT/US2010/001952, Feb. 2, 2011, International Search Report and Written Opinion.
PCT/US2010/001952, Jan. 26, 2012, International Preliminary Report on Patentability.
EP 09800675.2, dated Dec. 6, 2012, Extended European Search Report.
PCT/US2009/004260, Mar. 19, 2010, Invitation to Pay Additional Fees.
PCT/US2009/004260, Oct. 15, 2010, International Search Report and Written Opinion.
PCT/US2009/004260, Feb. 3, 2011, International Preliminary Report on Patentability.
EP 12159110.1, Jul. 20, 2012, Extended European Search Report.
EP 12159110.1, Sep. 27, 2012, Extended European Search Report (Replacement).
EP 16182714.2, Jan. 30, 2017, Extended European Search Report.
PCT/US2008/058575, Nov. 17, 2008, International Search Report and Written Opinion.
PCT/US2008/058575, Oct. 8, 2009, International Preliminary Report on Patentability.
PCT/US2011/052755, Feb. 16, 2012, Invitation to Pay Additional Fees.
PCT/US2011/052755, Apr. 25, 2012, International Search Report and Written Opinion.
PCT/US2011/052755, Apr. 4, 2013, International Preliminary Report on Patentability.
PCT/US2012/042738, Oct. 18, 2012, International Search Report and Written Opinion.
PCT/US2012/042738, Jan. 3, 2014, International Preliminary Report on Patentability.
PCT/US2013/062004, Jan. 2, 2014, Invitation to Pay Additional Fees.
PCT/US2013/062004, Apr. 23, 2014, International Search Report and Written Opinion.
PCT/US2013/062004, Apr. 9, 2015, International Preliminary Report on Patentability.
PCT/US2013/062929, Jan. 30, 2014, International Search Report and Written Opinion.
PCT/US2013/062929, Apr. 16, 2015, International Preliminary Report on Patentability.
EP 14775716.5, dated Jul. 5, 2016, Extended European Search Report.
PCT/US2014/025544, Jul. 22, 2014, Invitation to Pay Additional Fees.
PCT/US2014/025544, Sep. 10, 2014, International Search Report and Written Opinion.
PCT/US2014/025544, Sep. 24, 2015, International Preliminary Report on Patentability.
PCT/US2014/042329, Nov. 24, 2014, International Search Report and Written Opinion.
PCT/US2014/042329, Dec. 23, 2015, International Preliminary Report on Patentability.
PCT/US2014/041338, Nov. 10, 2014, International Search Report and Written Opinion.
PCT/US2014/041338, Dec. 17, 2015, International Preliminary Report on Patentability.
PCT/US2014/058680, Apr. 23, 2015, International Search Report and Written Opinion.
PCT/US2014/058680, Apr. 14, 2016, International Preliminary Report on Patentability.
EP 12800679.8, Oct. 2, 2014, Extended European Search Report.
PCT/US2012/042719, Nov. 1, 2012, International Search Report and Written Opinion.
PCT/US2012/042719, Jan. 3, 2014, International Preliminary Report on Patentability.
PCT/US2008/052580, May 16, 2008, International Search Report and Written Opinion.
Benito et al,. Bicyclic Organo-Peptides as Selective Carbohydrate Receptors: Design, Solid-phase Synthesis, and on-bead Binding Capability. QSAR & Combinatorial Science, 2004; 23:117-129.
Reenberg et al., Specific Recognition of Disaccharides in Water by an Artificial Bicyclic Carbohydrate Receptor. European Journal of Org. Chem. 2007; 30:5003-5009.
Timmerman et al,. Rapid and quantitative cyclization of multiple peptide loops onto synthetic scaffolds for structural mimicry of protein surfaces. Chembiochem. May 2005;6(5):821-4.

ns, T. Kolter, *Angew. Chem. Int. Ed. Engl.*

STABILIZED COMPOUNDS HAVING SECONDARY STRUCTURE MOTIFS

RELATED APPLICATIONS

This application is a continuation of and claims priority under 35 U.S.C. § 120 to U.S. Patent Application, U.S. Ser. No. 15/287,513, filed Oct. 6, 2016, now U.S. Pat. No. 9,951,099; which is a continuation of and claims priority under 35 U.S.C. § 120 to U.S. Patent Application, U.S. Ser. No. 14/068,844, filed Oct. 31, 2013, now U.S. Pat. No. 9,505,801; which is a continuation of and claims priority under 35 U.S.C. § 120 to U.S. Patent Application, U.S. Ser. No. 13/680,905, filed Nov. 19, 2012, now U.S. Pat. No. 8,895,699; which is a continuation of and claims priority under 35 U.S.C. § 120 to U.S. Patent Application, U.S. Ser. No. 12/796,212, filed Jun. 8, 2010, now U.S. Pat. No. 8,324,428; which is a continuation of and claims priority under 35 U.S.C. § 120 to U.S. Patent Application, U.S. Ser. No. 11/148,976, filed Jun. 9, 2005, now U.S. Pat. No. 7,786,072; which is a continuation of and claims priority under 35 U.S.C. § 120 to U.S. Patent Application, U.S. Ser. No. 09/574,086, filed May 18, 2000, now U.S. Pat. No. 7,192,713; which claims the benefit of priority under U.S.C. § 119(e) to U.S. Provisional Patent Applications, U.S. Ser. No. 60/167,634, filed Nov. 26, 1999, and U.S. Ser. No. 60/134,708, filed May 18, 1999.

GOVERNMENT SUPPORT

This invention was made with government support under GM51330 awarded by the National Institutes of Health. The government has certain rights in the invention.

BACKGROUND OF THE INVENTION

The important biological roles that peptides play as hormones, enzyme inhibitors, substrates, neurotransmitters, and neuromediators has led to the widespread use of peptides in medicinal chemistry as therapeutic agents. Through binding to receptors or enzymes, peptides are able to influence cell-cell communication and control vital cell functions such as metabolism, immune defense and reproduction. Babine et al., *Chem. Rev.* 1997, 97, 1359). Unfortunately, the utility of peptides as drugs is severely limited by several factors, including their rapid degradation by peptidases under physiological conditions, their poor cell permeability, and their lack of binding specificity resulting from conformational flexibility.

In response to these unfavorable characteristics of peptide drugs, many research groups have developed strategies for the design and synthesis of chemical compounds, known as "peptidomimetics", in which sensitive peptide moieties are removed and replaced with more robust functionalities. In particular, researchers have sought to improve peptide stability and cell permeability by replacing the amide functionality with groups such as hydroxyethylene, (E)-alkenes, carba groups and phosphonamide groups (see, Gante, *J. Angew. Chem. Int. Ed. Engl.* 1994, 33, 1699-1720, and references cited therein).

Another approach that researchers have taken in the development of peptide drugs is the study of, initiation of, and retention of peptide secondary structures. These secondary structures, α-helices, β-sheets, turns, and loops, are essential conformational components for peptides and proteins because bioactive conformations are fixed to a high degree by such structural elements. Because of the biological importance of these secondary structures, the development of novel structures incorporating these secondary structures has been a subject of intense research (see, for example, R. M. J. Liskamp, *Recl. Tray. Chim. Pays-Bas* 1994, 113, 1; Giannis, T. Kolter, *Angew. Chem. Int. Ed. Engl.* 1993, 32, 1244; P. D. Bailey, Peptide Chemistry, Wiley, New York, 1990, p. 182). In particular, the formation of α-helices by peptides has been of interest because many biologically important protein interactions, such as p53/MDM2 and Bcl-X1/Bak, are mediated by one protein donating a helix into a cleft of its α-helix-accepting partner. Unfortunately, it has been very difficult to mimic the approximately 12 amino acids (i.e., three turns of an alpha helix) required to form a stabilized isolated helical peptide. As described in "Bioorganic Chemistry: Peptides and Proteins", Chapter 12, Peptide Mimetics, Nakanishi and Kahn, the entire contents of which are incorporated herein by reference, most of the effort in the design and synthesis of α-helix mimetics has centered around N-termination initiation motifs. Furthermore, studies have been undertaken to understand the mechanisms of α-helix formation by peptides, and thus studies of helix-stabilizing side chain interactions, and template-nucleated α-helix formation have been investigated (see, J. Martin Scholtz and Robert L. Baldwin, "The Mechanism of α-Helix Formation by Peptides, *Ann. Rev. Biophys. Biomol. Struct.* 1992, 21, 95, the entire contents of which are incorporated herein by reference) in an attempt to understand-helix formation to aid in the future development of stabilized α-helix structures.

Clearly, it would be desirable to develop novel methods to generate stabilized-helical structures, as well as other secondary structures, to enable the investigation of complex structure-function relationships in proteins and ultimately to enable the development of novel therapeutics incorporating specific stabilized secondary structure motifs.

SUMMARY OF THE INVENTION

The present invention provides novel compounds having stabilized secondary structure motifs, and methods for their preparation. In general, the synthesis of these stabilized secondary structures involves (1) synthesizing a peptide from a selected number of natural or non-natural amino acids, wherein said peptide comprises at least two reactive moieties capable of undergoing a carbon-carbon bond forming reaction; and (2) contacting said peptide with a reagent to generate at least one crosslinker and to effect stabilization of a specific secondary structure motif. In one embodiment, the present invention provides novel alpha helix structures having stabilizing crosslinkers, libraries of these novel alpha helix structures, and methods for the synthesis of these alpha helices and libraries thereof. In certain embodiments, olefin metathesis reactions are utilized to generate these novel α-helical structures comprising (1) synthesizing a peptide from a selected number of natural or non-natural amino acids, wherein said peptide comprises at least two vinyl amino acids capable of undergoing an olefin metathesis reaction or comprises at least one divinyl amino acid and at least two vinyl amino acids capable of undergoing olefin metathesis reactions; and (2) contacting said peptide with a metathesis catalyst to generate at least one crosslinker and to effect stabilization of an alpha helix structure. In one preferred embodiment, at least two vinyl amino acids are incorporated into the peptide synthesis to generate at least one crosslinker. In another preferred embodiment, at least two vinyl amino acids and at least one divinyl amino acid are incorporated to generate at least two crosslinkers originating from the same amino acid. Alternatively, any combination of divinyl amino acids and vinyl amino acids may be incorporated to generate desired crosslinked structures. It will also be appreciated that in certain embodiments, one or more of either of these crosslinker motifs can be incorporated into a desired stabilized α-helix structure.

In another embodiment, the method of the present invention is utilized to provide stabilized p53 donor helical peptides by incorporating vinyl amino acids into this structural motif and reacting said vinyl amino acids to generate stabilized α-helical structures. Additionally, the present invention provides methods for disrupting the p53/MDM2 binding interaction comprising (1) providing a crosslinker stabilized α-helical structure; and (2) contacting said stabilized α-helical structure with MDM2.

As will be appreciated by one of ordinary skill in the art, in one embodiment, the novel compounds having stabilized secondary structure motifs of the present invention can be synthesized one-at-at time, using traditional peptide synthetic techniques, to generate a particular structural motif. In preferred embodiments, however, the these novel stabilized secondary structures are synthesized using combinatorial synthetic techniques, in solution or on the solid support, to generate diverse libraries of novel stabilized compounds having desired secondary structure motifs. Whether using traditional synthetic techniques or combinatorial synthetic techniques, the method of the present invention provides for the generation of compounds having desired stabilized secondary structure motifs that can be based on existing structural motifs (p53) or that can represent novel unnatural peptide secondary structure motifs to explore heretofore unknown biological interactions.

DESCRIPTION OF CERTAIN PREFERRED EMBODIMENTS

Figure 1:
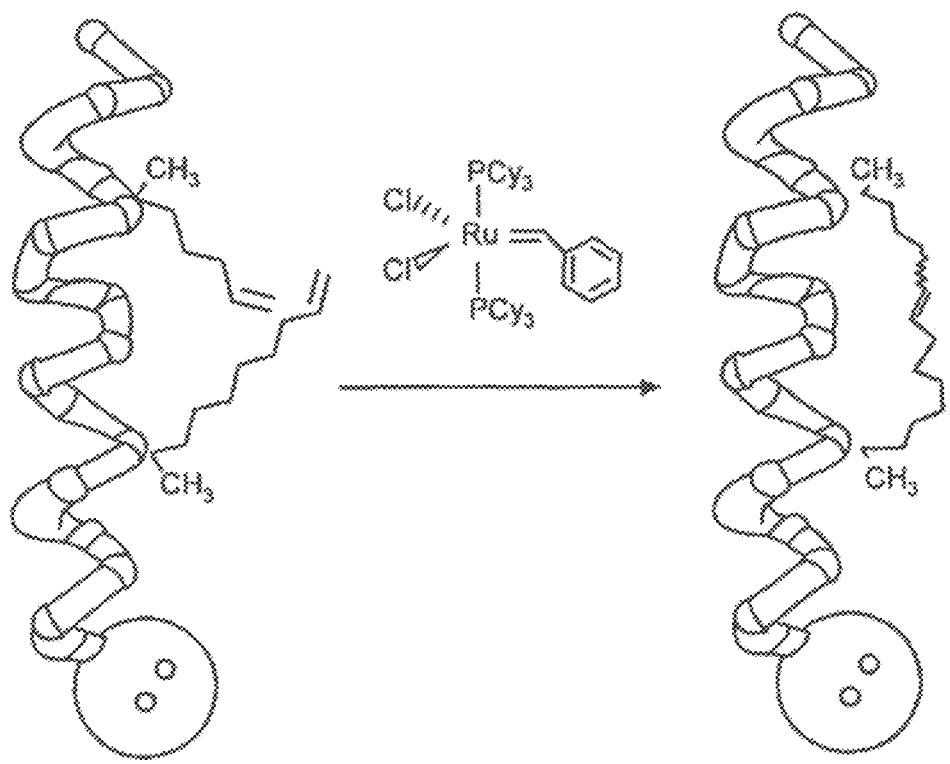
FIG. 1 depicts a particularly preferred embodiment of the invention in which a helix crosslinker is installed using olefin metathesis.

The present invention provides stabilized compounds having specific secondary structure motifs and improved methods for generating stabilized compounds having these specific secondary structure motifs. The novel stabilized compounds of the present invention are useful where such structural motifs are advantageous; for example, in drug design and delivery, and in but a few examples, as inhibitors of p53/MDM2 and Bak/Bcl-$x_L$ interactions.

In general, the synthesis of these stabilized secondary structures involves (1) synthesizing a peptide from a selected number of natural or non-natural amino acids, wherein said peptide comprises at least two reactive moieties capable of undergoing a C—C bond forming reaction; and (2) contacting said peptide with a reagent to generate at least one crosslinker and to effect stabilization of a specific secondary structure motif. In one embodiment, the present invention provides novel alpha helix structures having stabilizing crosslinkers, libraries of these novel alpha helix structures, and methods for the synthesis of these alpha helices and libraries thereof. In certain embodiments, olefin metathesis reactions are utilized to generate these novel α-helical structures comprising (1) synthesizing a peptide from a selected number of natural or non-natural amino acids, wherein said peptide comprises at least two vinyl amino acids capable of undergoing an olefin metathesis reaction or comprises at least one divinyl amino acid and at least two vinyl amino acids capable of undergoing olefin metathesis reactions; and (2) contacting said peptide with a metathesis catalyst to generate at least one crosslinker and to effect stabilization of an alpha helix structure. In one preferred embodiment, at least two vinyl amino acids are incorporated into the peptide synthesis to generate at least one crosslinker. In another preferred embodiment, at least two vinyl amino acids and at least one divinyl amino acid are incorporated to generate at least two crosslinkers originating from the same amino acid. Alternatively, any combination of divinyl amino acids and vinyl amino acids may be incorporated to generate desired crosslinked structures. It will also be appreciated that in certain embodiments, one or more of either of these crosslinker motifs can be incorporated into a desired stabilized α-helix structure.

In another embodiment, the method of the present invention is utilized to provide stabilized p53 donor helical peptides by incorporating vinyl amino acids into this structural motif and reacting said vinyl amino acids to generate stabilized α-helical structures. Additionally, the present invention provides methods for disrupting the p53/MDM2 binding interaction comprising (1) providing a crosslinker stabilized α-helical structure; and (2) contacting said stabilized α-helical structure with MDM2.

As will be appreciated by one of ordinary skill in the art, in one embodiment, the novel compounds having stabilized secondary structure motifs of the present invention can be synthesized one-at-at time, using traditional peptide synthetic techniques, to generate a particular structural motif. In preferred embodiments, however, the these novel stabilized secondary structures are synthesized using combinatorial synthetic techniques, in solution or on the solid support, to generate diverse libraries of novel stabilized compounds having desired secondary structure motifs. Whether using traditional synthetic techniques or combinatorial synthetic techniques, the method of the present invention provides for the generation of compounds having desired stabilized secondary structure motifs that can be based on existing structural motifs or that can represent novel unnatural peptide secondary structure motifs to explore heretofore unknown biological interactions.

Certain preferred embodiments of the novel compound having stabilized secondary structures will be described below; however, this description is not meant to limit the scope of the present invention. Rather, it will be appreciated that all equivalents are intended to be included within the scope of the present invention.

Synthesis of Novel Compounds Having Stabilized Secondary Structure Motifs

As discussed above, the present invention provides novel stabilized compounds having specific secondary structure motifs, libraries thereof, and methods for the preparation of these compounds and libraries thereof. In certain preferred embodiments, the present invention also provides novel α-helix structures, libraries thereof, and methods for the preparation of these α-helices and libraries thereof. Although the following discussion and description of the method of the present invention focuses on alpha helices, it will be appreciated that the methods of the present invention can be applied to generate other peptide secondary structures as well.

Figure 2:
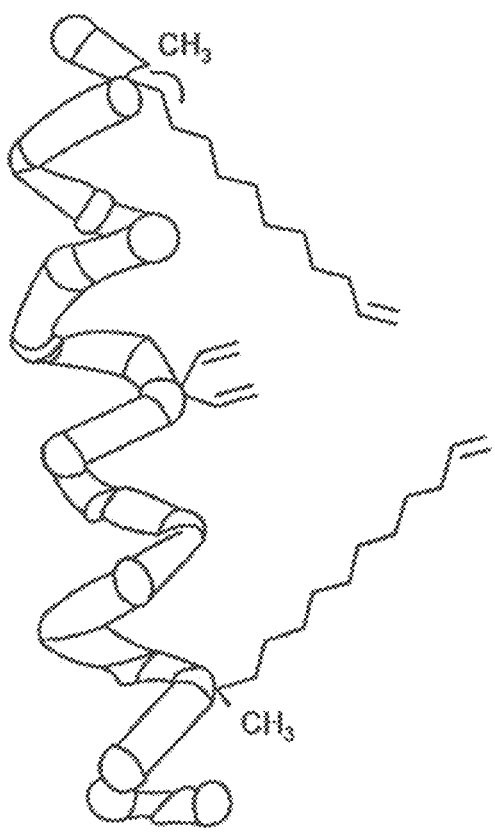
FIG. 2 depicts the installation of a divinyl amino acid for the stabilization of four turns (represented by SEQ ID NO:4).

The synthesis of novel α-helix structures first involves the selection of a desired number of amino acid starting materials. As one of ordinary skill in the art will realize, the number, stereochemistry, and type of amino acid structures (natural or non-natural) selected will depend upon the size of the α-helix to be prepared, the ability of the particular amino acids to generate the α-helix structural motif, and any particular motifs that are desirable to mimic (for example, the p53 donor helical peptide). Furthermore, as mentioned above, for the synthesis of the stabilized alpha helixes, in one preferred embodiment, at least two of the desired amino acids to be utilized in the synthesis are vinyl amino acids capable of undergoing ring closing metathesis reactions to generate at least one stabilizing crosslinker, as shown in FIG. 1. In another preferred embodiment, the peptide to be synthesized incorporates at least two vinyl amino acids and one divinyl amino acid to generate at least two stabilizing crosslinkers originating from the same amino acid moiety, as shown in FIG. 2. It will be appreciated, however, that the number of crosslinking moieties is not limited to one or two, as described above, respectively; rather the number of crosslinking moieties utilized can be varied with the length of the alpha helix as desired, and as compatible with the desired structure to be generated.

Figure 3:
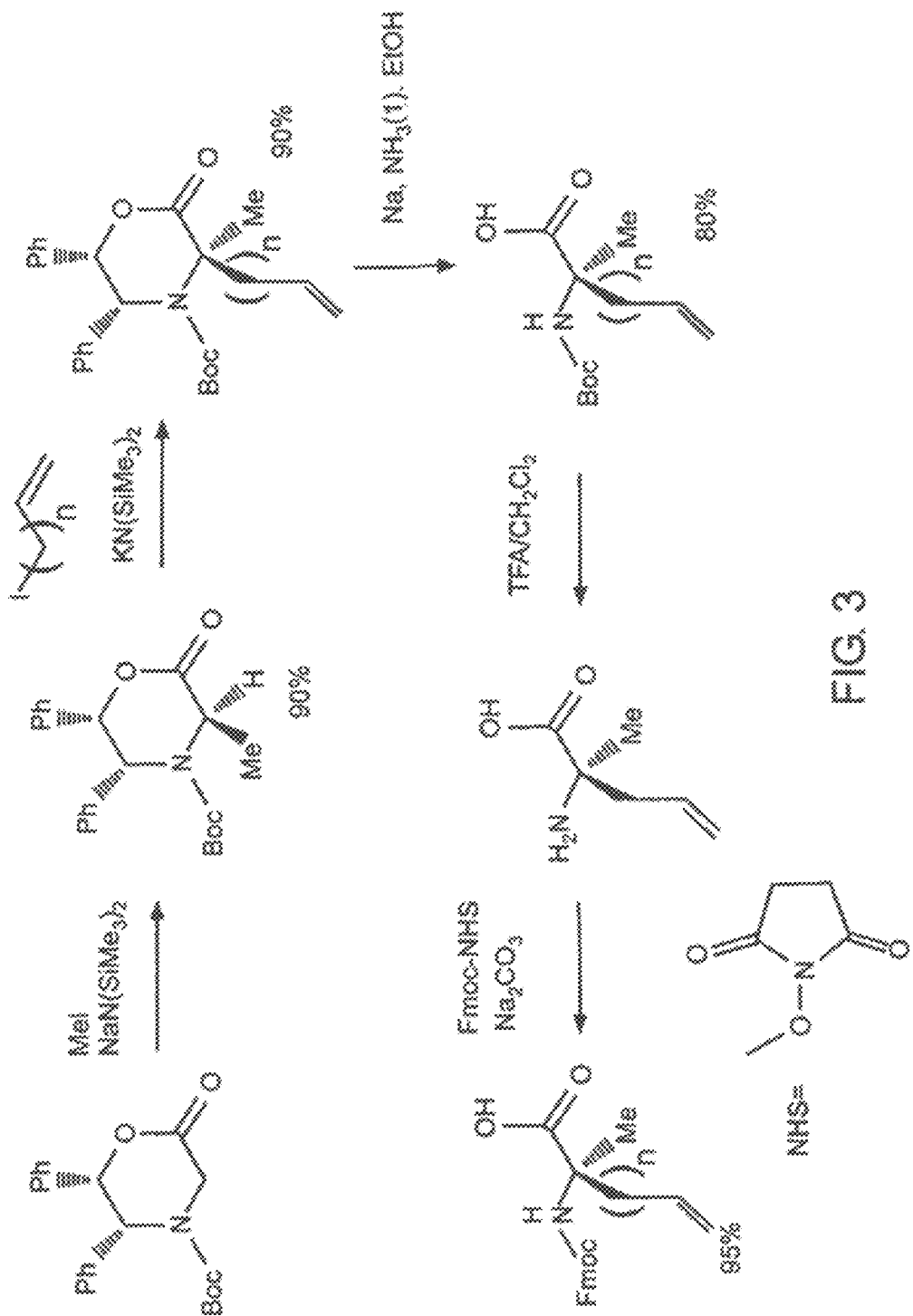
FIG. 3 depicts the synthesis of α-methyl α-alkylolefin amino acids.
Figure 4:
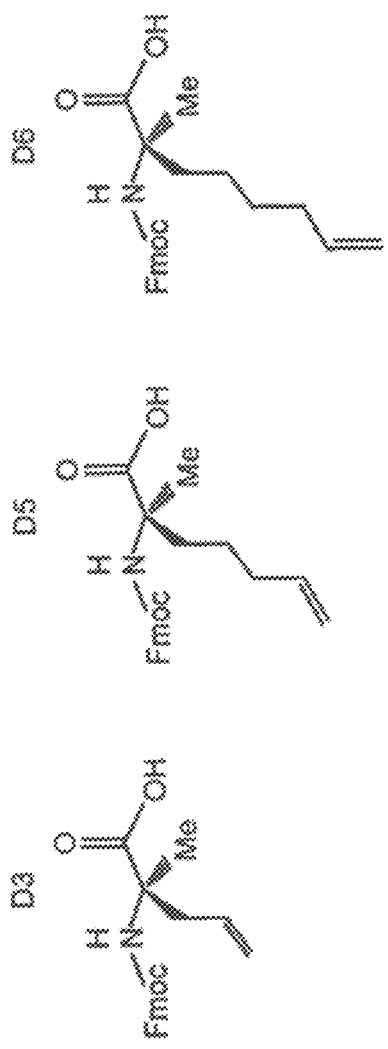
FIG. 4 depicts several different α-methyl α-alkylolefin amino acids for use in the present invention.
Figure 4:
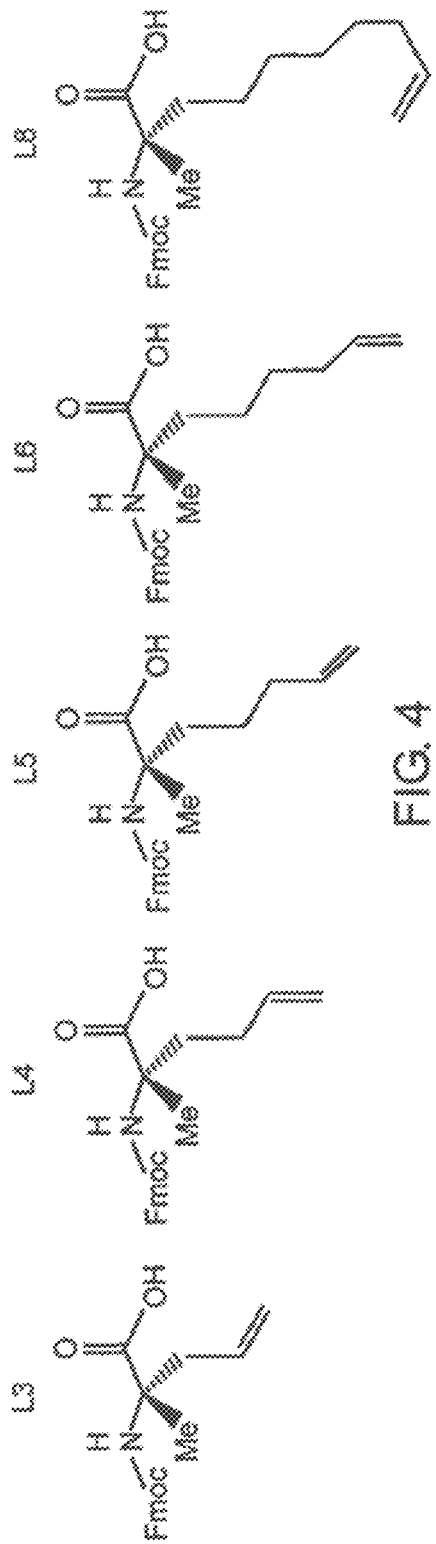

In particularly preferred embodiments, α-methyl, α-vinyl amino acids are utilized in the present invention as precursors for crosslinker formation. FIG. 3 depicts a general scheme of the synthesis of α-methyl, α-alkylolefin amino acids. As shown in FIG. 3, commercially available lactone (1) is treated with methyl iodide and sodium tetramethyl disilylazide to generate the methylated lactone (2). Subsequent treatment with a homoallyl iodide in the presence of potassium tetramethyl disilylazide yields the homoallyloxazinone (3). Sodium metal reduction, acid hydrolysis, and protection with Fmoc-NHS generates the protected α-methyl, α-alkylolefin (4) for use in the synthesis of the novel alpha helix structures. As one of ordinary skill in the art will realize, a variety of homoallyl reagents can be utilized to generate amino acids having different lengths of olefin chains. It will also be appreciated that these olefin chains can also be further functionalized with moieties including, but not limited to, branched or linear alkyl moieties, hydroxyl moieties, thiol moieties, amines, carboxyl moieties and substituted or unsubstituted aryl moieties, to name a few. FIG. 4 also depicts certain preferred α-methyl, α-alkylolefin amino acids for use in the present invention having different olefin chain lengths.

Figure 5:
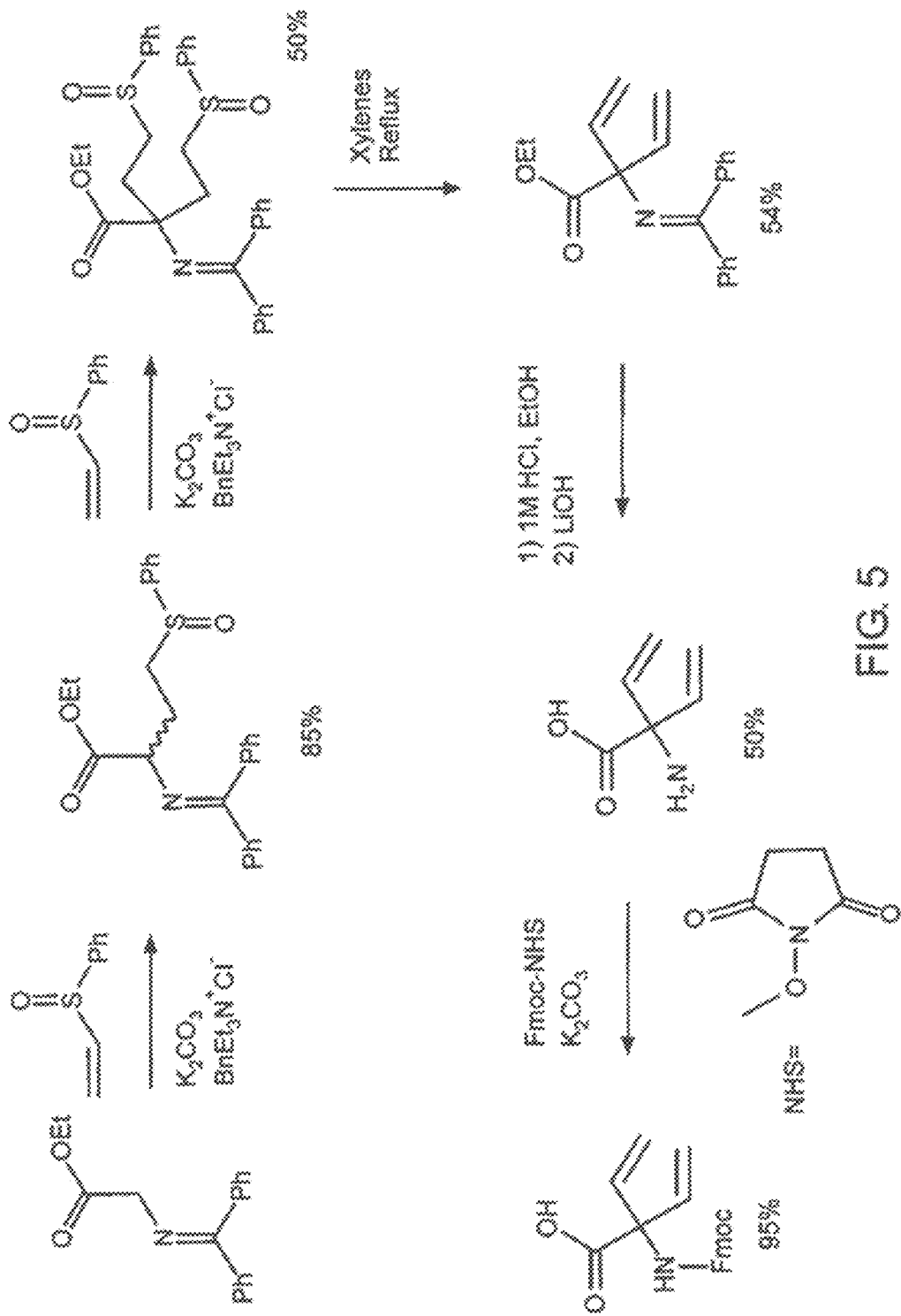
FIG. 5 depicts the synthesis of an Fmoc protected divinyl amino acid.

As discussed above, the novel α-helices of the present invention may also contain two crosslinking units originating from one amino acid. This is facilitated by the synthesis of a divinyl amino acid, from which two olefin metathesis reactions can originate, and is preferably incorporated into the desired peptide synthesis. FIG. 5 depicts the synthesis of an Fmoc protected divinyl amino acid. As shown in FIG. 5, reaction of diphenyliminoglycine (1) sequentially with two equivalents of phenylvinylsulfoxide (2) generates a bis phenylsulfoxide (3), which, upon treatment with xylenes under reflux conditions, eliminates to yield the divinyl moiety (4). Subsequent saponification, acid hydrolysis and deprotection yields the unprotected divinyl glycine moiety (5). Finally, protection with Fmoc-NHS at room temperature yields the protected divinyl glycine moiety (6) for use in the synthesis of the novel α-helix structures of the present invention.

Although vinyl amino acids and divinyl amino acids are preferably utilized to generate the preferred crosslinking moieties as discussed above using ring closing metathesis reactions, the other amino acids utilized in the peptide synthesis may be selected from any standard or nonstandard amino acids. The standard amino acids include Glycine, Alanine, Valine, Leucine, Isoleucine, Proline, Phenylalanine, Tryptophan, Methionine, Serine, Threonine, Cysteine, Tyrosine, Asparagine, Glutamine, Aspartic acid, Glutamic acid, Lysine, Arginine and Histidine. There are over 700 known nonstandard amino acids any of which may be included in the peptide precursors for use in the present invention. See, for example, S. Hunt, The Non-Protein Amino Acids: In Chemistry and Biochemistry of the Amino Acids, edited by G. C. Barrett, Chapman and hall, 1985. Some examples of non-standard amino acids are β-alanine, D-alanine, 4-hydroxyproline, desmosine, D-glutamic acid, α-aminobutyric acid, β-cyanoalanine, norvaline, 4-(E)-butenyl-4(R)-methyl-N-methyl-L-threonine, N-methyl-L-leucine, and statine. Additionally, the amino acids suitable for use in the present invention may be derivatized to include amino acid residues that are hydroxylated, phosphorylated, sulfonated, and glycosylated, to name a few. Additionally, these amino acids may include functional groups including, but not limited to alcohol, thiol, ketone, aldehyde, ester, ether, amine, imine, amide, nitro acid, carboxylic acid, disulfide, carbonate, carboalkoxy acid, isocyanate, carbodiimide, carboalkoxy and halogen functional groups. It will be appreciated by one of ordinary skill in the art, however, that certain amino acids are capable of promoting formation of alpha helix structures or other desired secondary structures, and thus these specific amino acids are particularly preferred for use in the present invention, depending on the desired secondary structure to be generated. For a detailed discussion of helix propensities studied in various substitution experiments, see Scholtz and Baldwin, the entire contents of which are incorporated herein by reference. Furthermore, as discussed above, it may be desirable to mimic an existing peptide α-helical structure, or other secondary structure, having the crosslinking moiety incorporated therein according to the method of the present invention.

Once the desired amino acids are selected for the synthesis of a desired peptide according to the present invention, synthesis of the desired peptide can be achieved using standard deprotection and coupling reactions. One example of a preferred solution phase peptide synthesis coupling protocol includes the use of N,N-dicyclohexylcarbodiimide (DCC)/1-hydroxybenzotriazole (HOBT) as a peptide coupling agent (see, M. Bordansky, Petpide Chemistry, Springer Verlag, N.Y., 1988, pp. 55-146 the entire contents of which are incorporated herein by reference). Other peptide synthesis techniques have been extensively discussed in "Bioorganic Chemistry" as cited herein. One of ordinary skill in the art will realize that the choice of a particular synthetic technique will depend upon the particular structures to be synthesized.

After a desired peptide is synthesized using an appropriate technique, the peptide is contacted with a specific reagent to promote carbon-carbon bond formation. In one particular embodiment, a metathesis catalyst is utilized to effect one or more olefin metathesis reactions and subsequent generation of a crosslinker and stabilization of the alpha helix or other desired secondary structure. One of ordinary skill in the art will realize that a variety of metathesis catalysts can be utilized in the present invention. Selection of a particular catalyst will vary with the reaction conditions utilized and the functional groups present in the particular peptide. Exemplary catalysts include, but are not limited to stabilized, late transition metal carbene complex catalysts such as Group VIII transition metal carbene catalysts, most preferably Ru and Os metal centers having a +2 oxidation state, an electron count of 16 and pentacoordinated. One of ordinary skill in the art will realize that other appropriate olefin metathesis catalysts may be utilized. For an excellent discussion of metathesis reactions, see, Grubbs et al., "Ring Closing Metathesis and Related Processes in Organic Synthesis" Acc. Chem. Res. 1995, 28, 446-452, and U.S. Pat. No. 5,811,515.

It will also be appreciated, that in addition to olefin metathesis catalysts, other reagents capable of promoting carbon-carbon bond formation can also be utilized. For example, other reactions that can be utilized, include, but are not limited to palladium coupling reactions, transition metal catalyzed cross coupling reactions, pinacol couplings (terminal aldehydes), hydrozirconation (terminal alkynes), nucleophilic addition reactions, and NHK (Nozaki-Hiyama-Kishi (Fürstner et al., J. Am. Chem. Soc. 1996, 118, 12349)) coupling reactions. Thus, the appropriate reactive moieties (alkene, alkyne, aldehyde etc.) are first incorporated into desired amino acids or unnatural amino acids (see vinyl amino acid synthesis for one example), and then the peptide is subjected to reaction conditions to effect carbon-carbon bond formation which results in the formation of a cross-linker and subsequent stabilization of a desired secondary structure.

Figure 6:
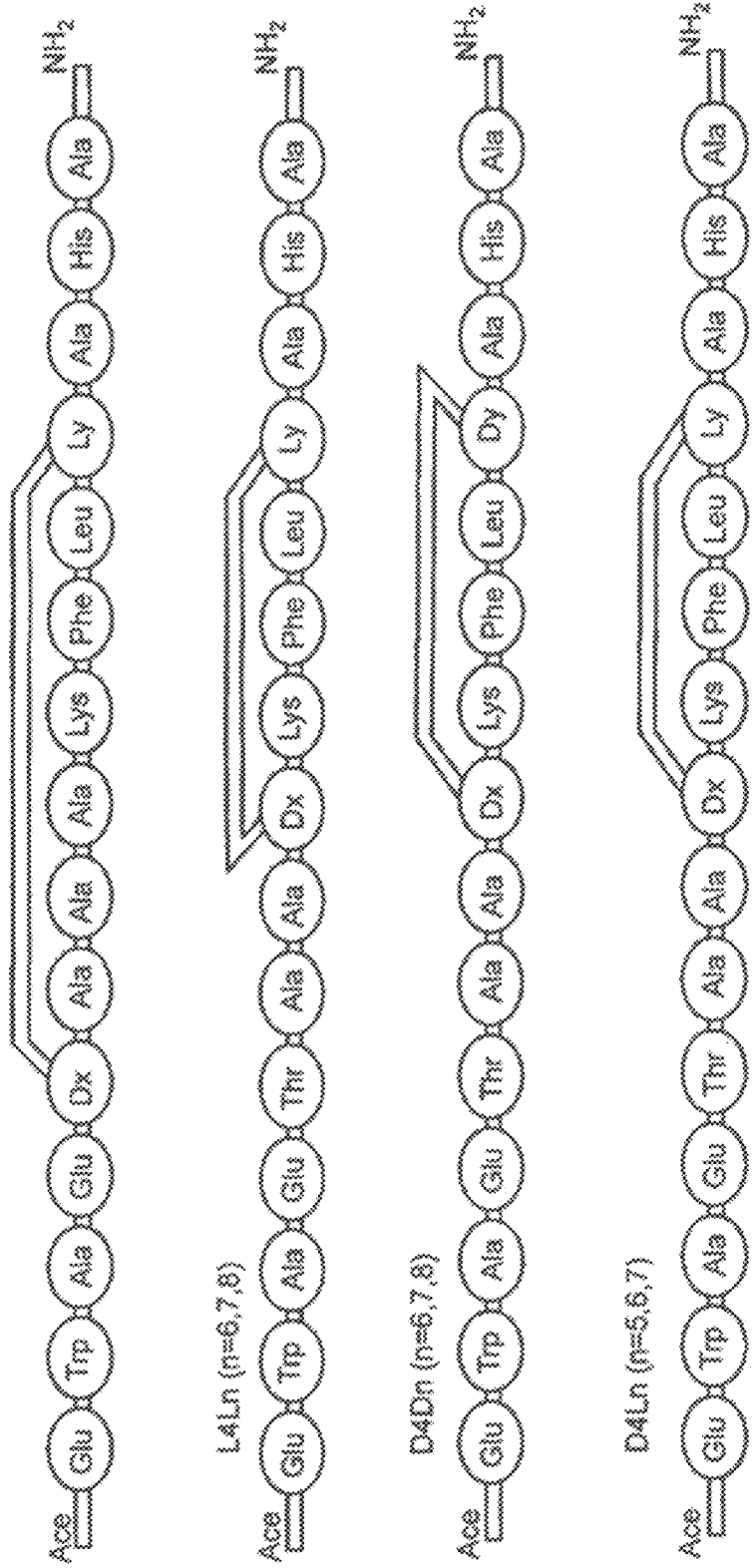
FIG. 6 depicts several different stabilized α-helix structures of the present invention (wherein D7Ln is represented by SEQ ID NO:2, and L4Ln, D4Dn, and D4Ln, are represented by SEQ ID NO:3).
Figure 6A:
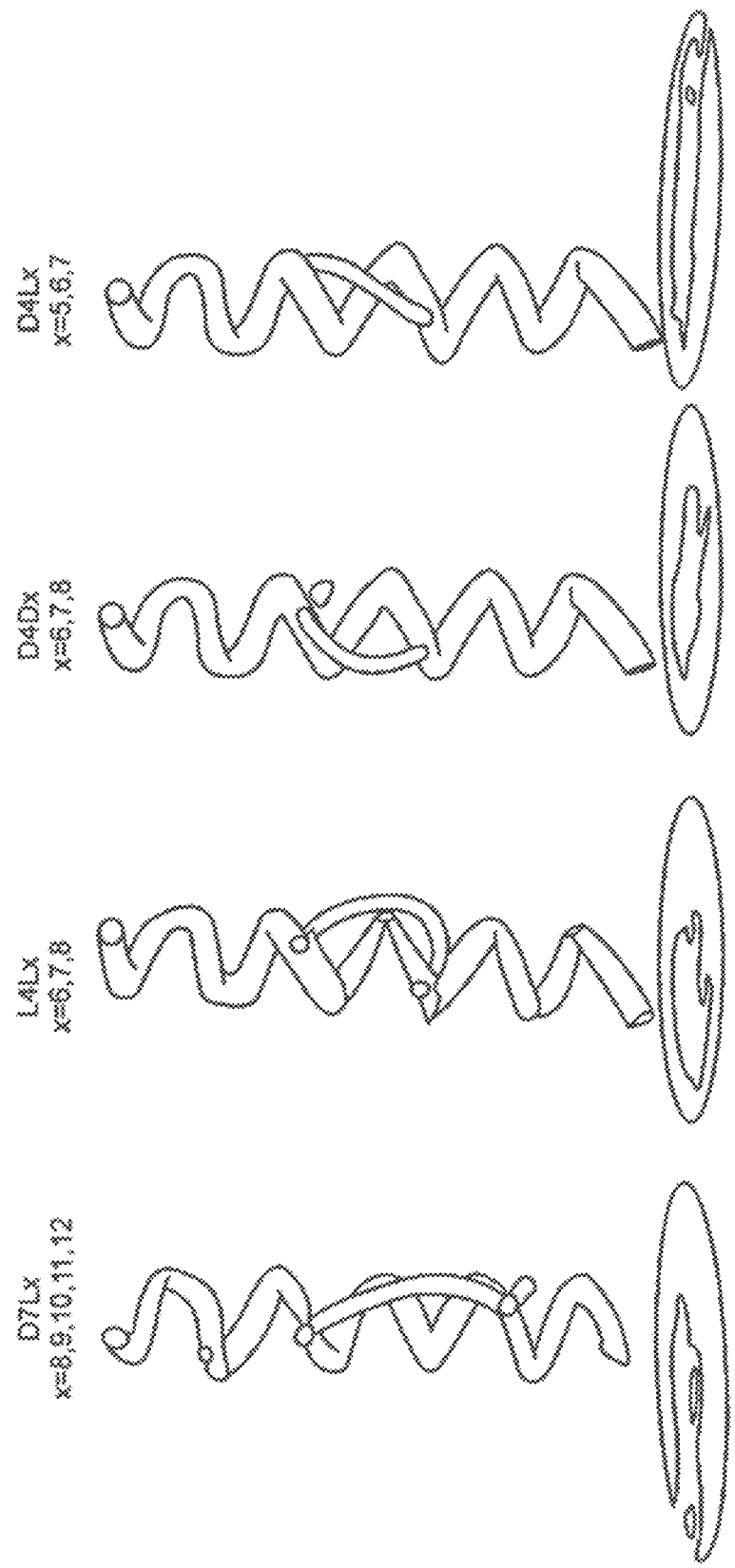
FIG. 6A depicts experimental determination of exemplary helix stabilizers.
Figure 7:
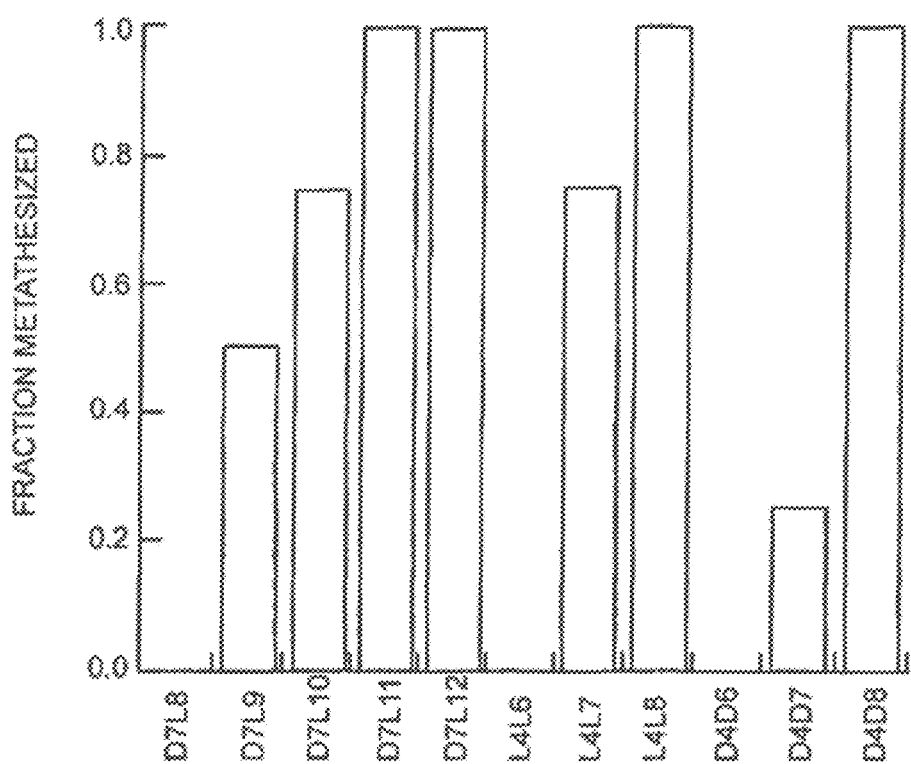
FIG. 7 depicts variations in metathesis yields in a two hour reaction.
Figure 8:
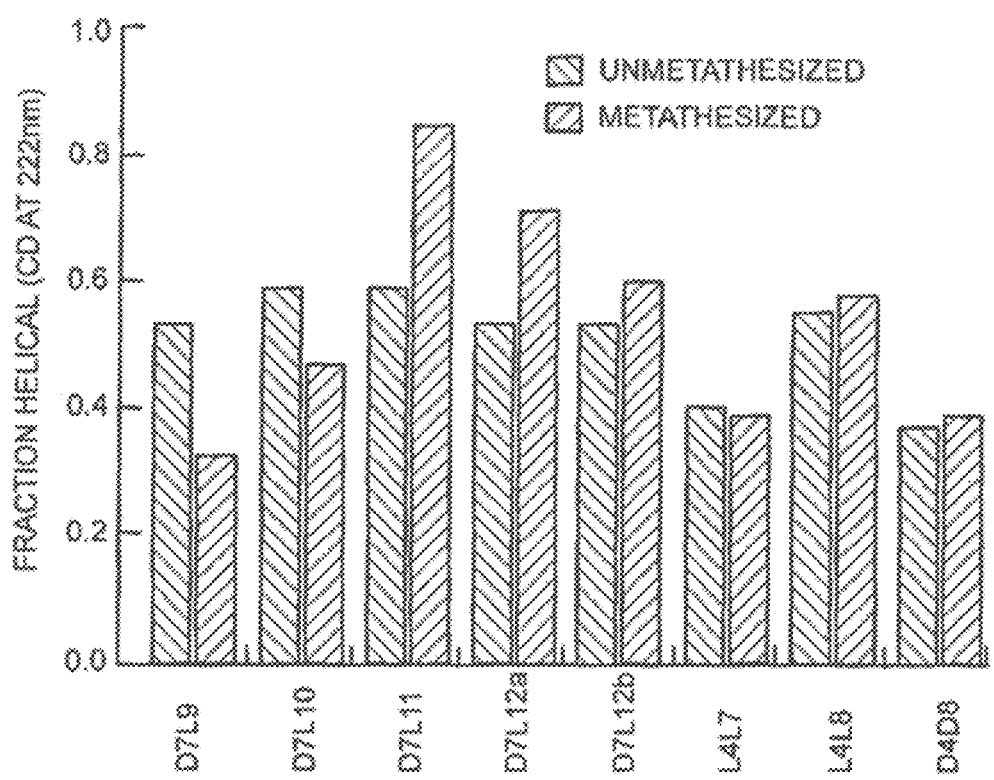
FIG. 8 depicts a graph showing a summary of α-helicity and metathesis percentages.
Figure 9:
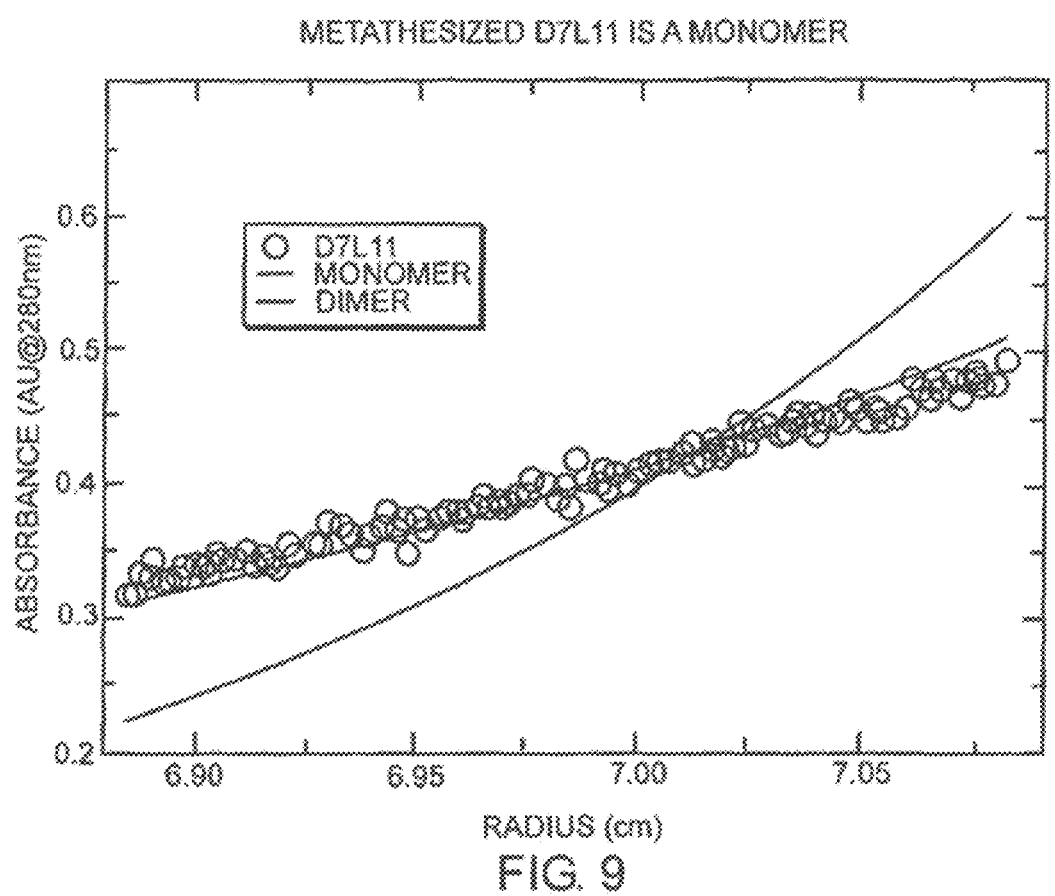
FIG. 9 depicts results showing that metathesized D7L11 is a monomer.

In a particularly preferred embodiment of the present invention, the method of the present invention was utilized to engineer stabilized alpha helical peptides that are capable of binding tightly to a helix acceptor and disrupting native protein/protein interactions. Towards this end, two alpha-methyl, alpha-alkyl terminal olefin unnatural amino acids, were incorporated into the peptide fragment that forms the donor helix in the native complex (p53) and cross-linking the amino acids using a ruthenium metathesis catalyst to form a bridge that stabilizes the peptide in an alpha helical conformation. Using this approach, 14 different model peptides (as shown in FIG. 6), incorporating different stereochemistry, vinyl amino acid placements and carbon chain lengths, were synthesized to explore the different ways of stabilizing the helix. Each of these were characterized by circular dichroism spectroscopy to determine the stabilization in an alpha helical conformation. FIG. 6A also depicts the experimental determination of the best helix stabilizer. FIG. 7 depicts the variation in the metathesis yields in a two hour reaction. As shown in FIG. 8, the % helicity is compared for metathesized and unmetathesized peptides and D7L11 provides the optimal helicity. Thus, it is particularly preferred to generate a structure having a cross link from residue (i) to residue (i+7) with (S) stereochemistry at the alpha carbon of residue (i) and (R) stereochemistry at position (i+7). It is also particularly preferred that the number of carbons in the crosslinker is eleven. As shown in FIG. 8, helix stabilizing cross-linker caused the model peptide to exhibit almost 90% helicity in water. FIG. 9 additionally shows that metathesized D7L11 is a monomer.

Figure 10:
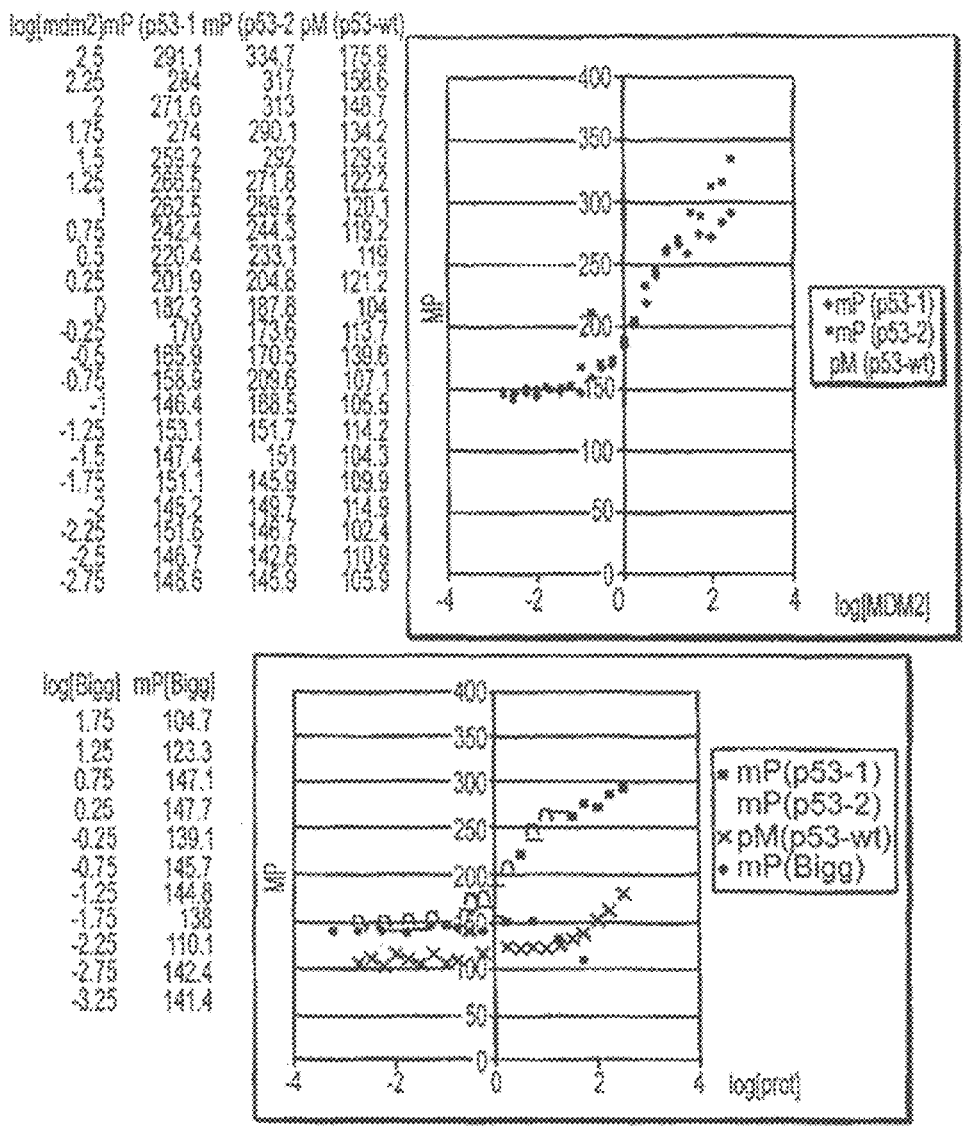
FIG. 10 depicts a fluorescence polarization binding study of p53 peptides with MDM2.

As an example of the utility of these novel stabilized alpha helix structures, this preferred alpha helix structure was implemented in the p53/MDM2 system by synthesizing two stabilized p53 donor helical peptides and determining their binding to the Xenopus MDM2 protein. The unnatural amino acids are incorporated into the p53 donor fragment on the side of the helix that does not interact with MDM2 so as not to disrupt the evolved p53/MDM2 binding interface. Preliminary fluorescence polarization results, as depicted in FIG. 10, show that both stabilized p53 peptides begin to bind MDM2 at 100 fold lower MDM2 concentration, and thus 100 fold tighter, than the native p53 donor fragment.

Figure 11:
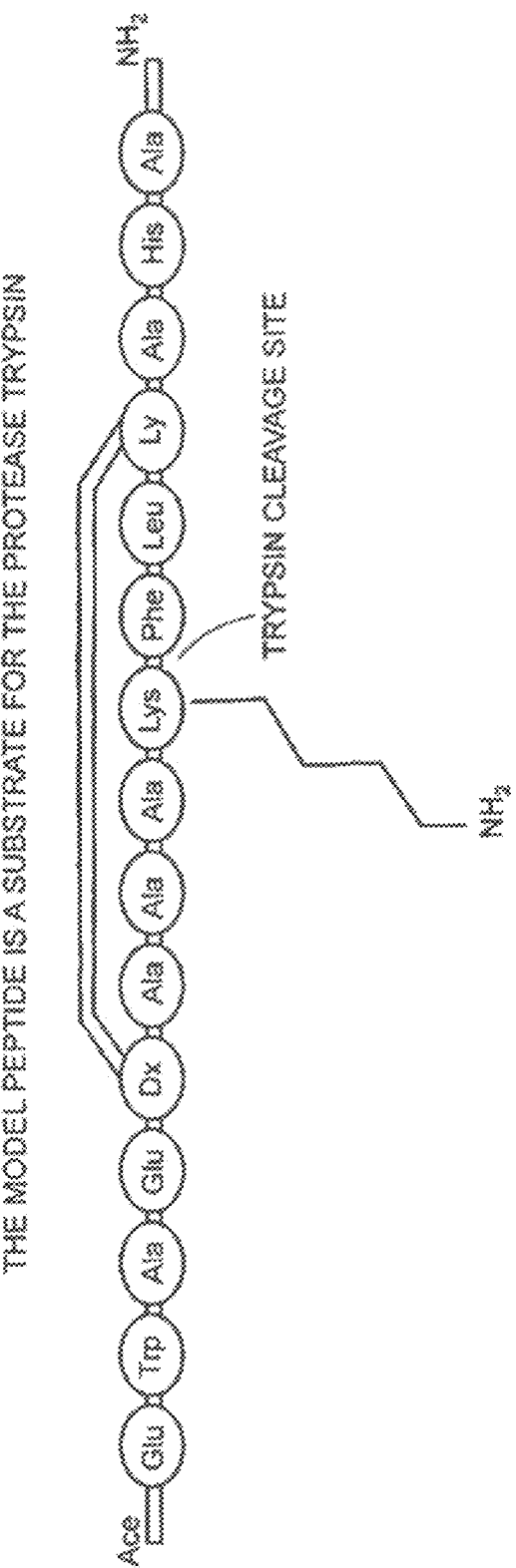
FIG. 11 depicts the model peptide as a substrate for the protease trypsin (represented by SEQ ID NO:2).
Figure 12:
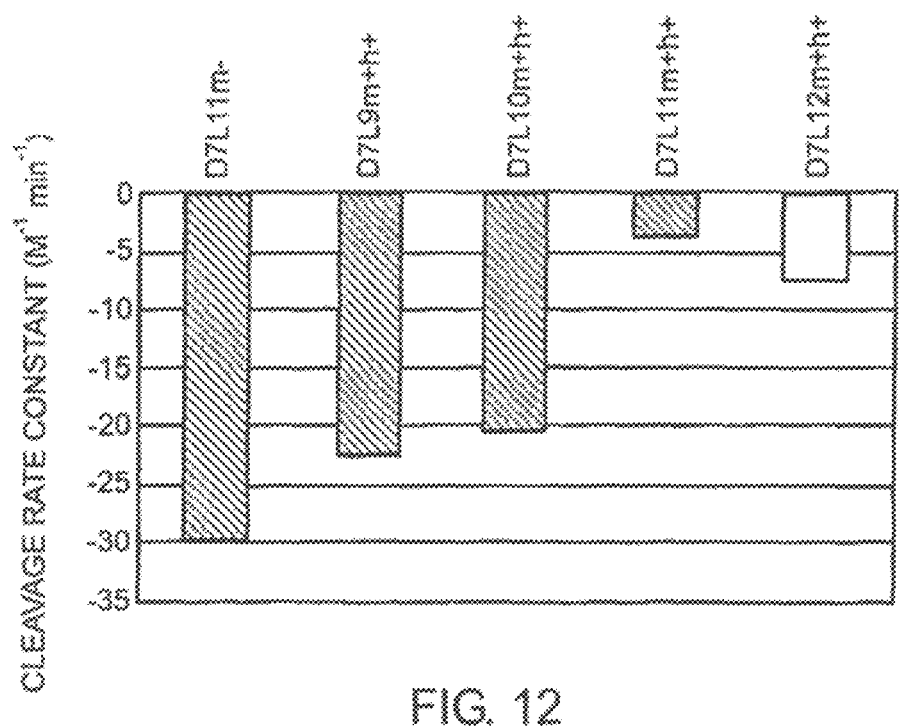
FIG. 12 depicts rates of Trypsin cleavage.
Figure 13:
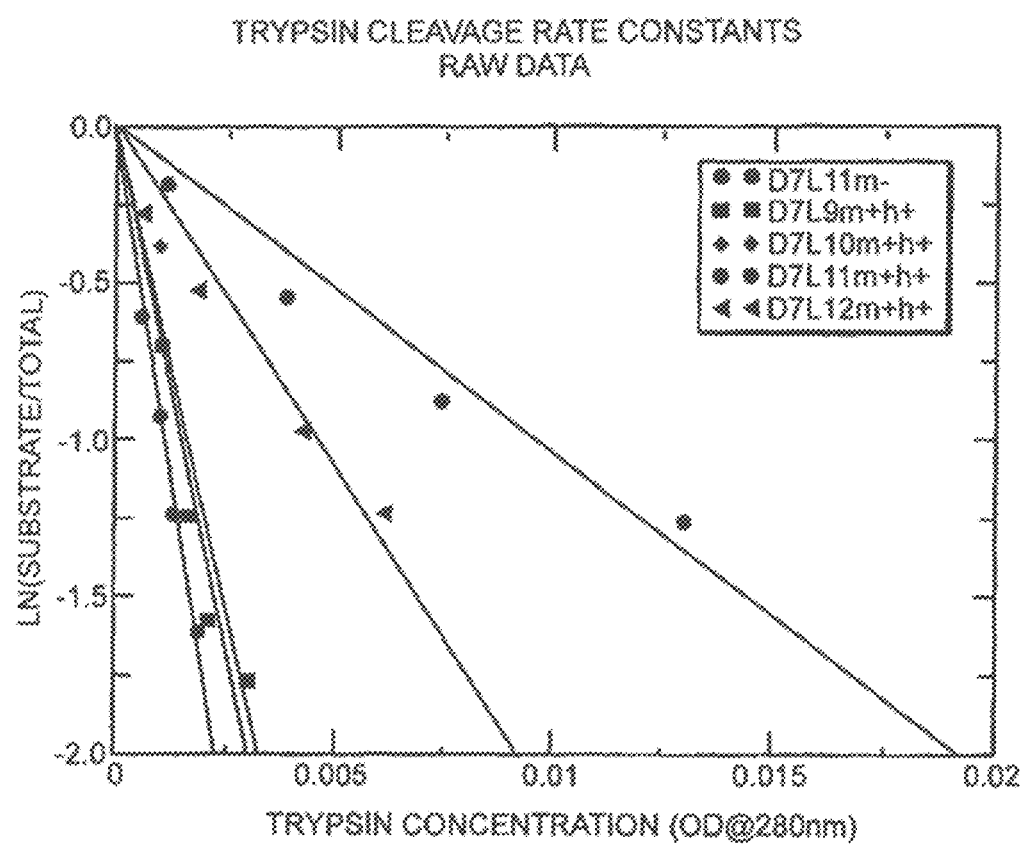
FIG. 13 depicts raw data for trypsin cleavage rate constants.
Figure 14:
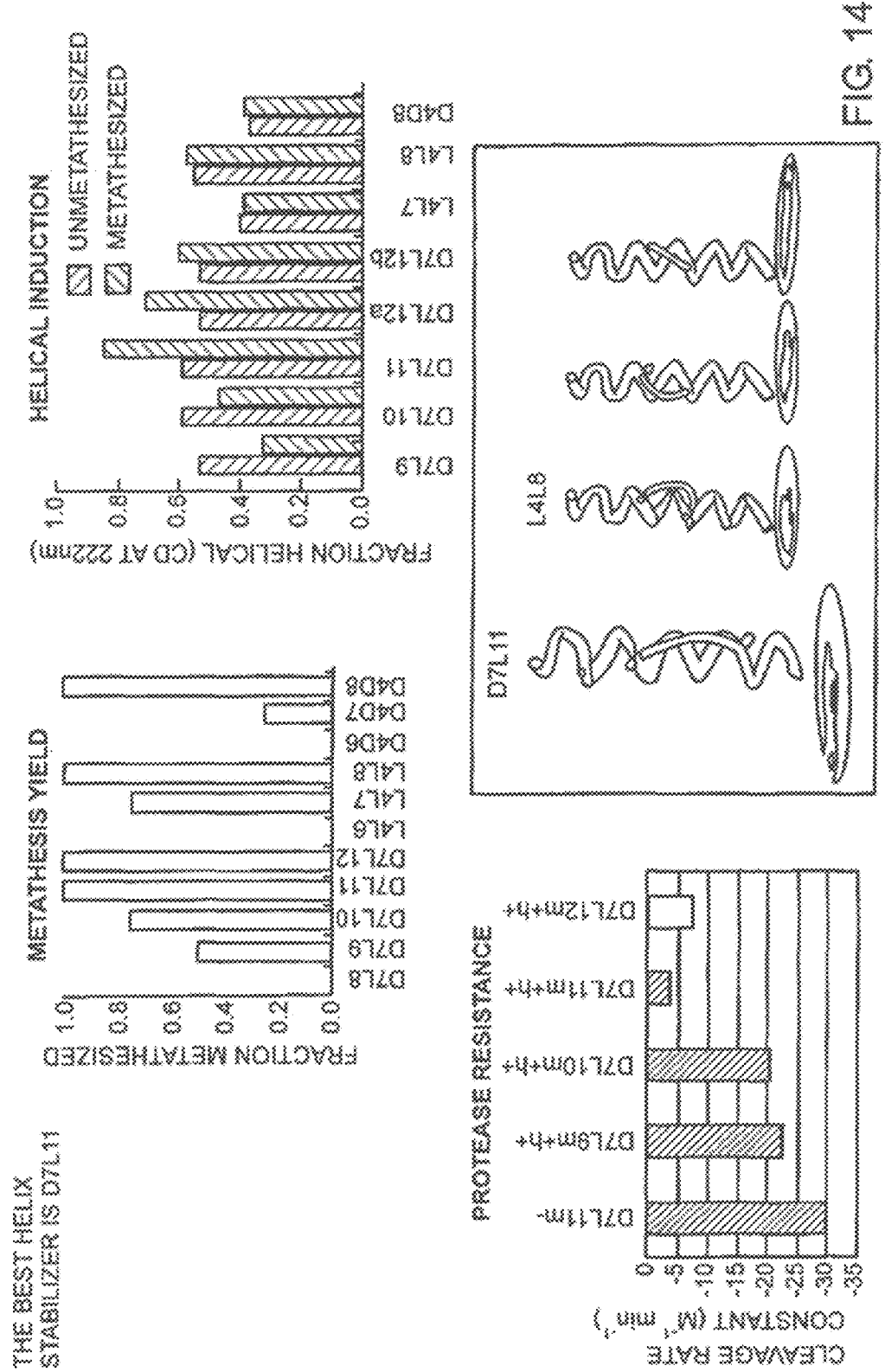
FIG. 14 depicts D7L11 as an exemplary helix stabilizer.

Additionally, FIG. 11 shows that the model peptide is a substrate for the protease trypsin. As depicted in FIGS. 12, 13, and 14, an inventive stabilized compound D7L11 shows the slowest rate of trypsin cleavage, and thus is an exemplary helix stabilizer.

Combinatorial Synthesis of Novel Stabilized Structures

It will also be appreciated by one of ordinary skill in the art that the method described above can also be applied to combinatorial synthesis of the novel stabilized structures having desired secondary structures. Although combinatorial synthesis techniques can be applied in solution, it is particularly preferred that combinatorial techniques are performed on the solid phase using split-and-pool techniques. In general, in a preferred method of the present invention, Solid Phase Peptide Synthesis (SPPS) techniques are utilized. Similarly to solution phase techniques, in solid phase techniques, the choice of the protecting groups must be considered, as well as the specific coupling techniques to be utilized. For a detailed discussion of peptide synthesis techniques for solution phase and solid phase reactions, see, Hecht, ed. "Bioorganic chemistry: Peptides and Proteins, Oxford University Press, New York: 1998, the entire contents of which are incorporated herein by reference.

The present invention, in one aspect, provides methods for the synthesis of libraries of novel stabilized compounds having secondary structure motifs comprising (1) providing a collection of resin-bound amino acids; (2) deprotecting each of said resin bound amino acids; (3) separating said collection of deprotected resin bound amino acids into n equal portions, wherein n represents the number of different types of amino acids to be coupled; (4) coupling of each of n types of amino acids to the deprotected amino acid; (5) combining each of the n portions together; (6) repeating steps (2)-(5) until a desired peptide is obtained, wherein at least two of the amino acids coupled at any step comprise substituted or unsubstituted vinyl amino acids capable of undergoing ring closing metathesis reaction, or wherein at least one amino acid coupled at any step comprises a substituted or unsubstituted divinyl amino acid and at least two of the amino acids incorporated at any step comprise substituted or unsubstituted vinyl amino acids, whereby said divinyl amino acid and said vinyl amino acid are capable of undergoing ring closing metathesis reactions to generate two cross-linkers originating from the same amino acid; and (7) contacting said peptide with a ring closing metathesis catalyst to generate a library of cross-linked stabilized α-helix peptide structures. During the course of the combinatorial synthesis, various parameters can be varied, including, but not limited to vinyl and divinyl amino acid placement, stereochemistry of amino acids, vinyl and divinyl chain length and functionality and amino acid residues utilized. Furthermore, as discussed above, other reactive moieties (such as aldehydes or alkynes, to name a few) can be utilized instead of alkene moieties and thus other carbon-carbon bond forming reactions can be utilized to form stabilized compounds having secondary structure motifs and are within the scope of the present invention.

It will be appreciated by one of ordinary skill in the art that the libraries of compounds having stabilized secondary structures can be further diversified at specific functional moieties after the desired stabilized structures are formed. For example, free or latent amino acid functionalities may be diversified, or alternatively or additionally, free or latent functionality present on the cross-linkers may be diversified. In particularly preferred embodiments, in but one example, the hydrophobicity of stabilized structures may be increased by the introduction of hydroxyl moieties. As one of ordinary skill in the art will realize, the diversification reactions will be selected to introduce functionalities compatible with the particular stabilized structures and the desired biological interactions, and these functionalities include, but are not limited to hydrogen, alkyl, aryl, phenoxy, methoxy, halide, benzene, heteroaryl, carboxyl, carboxalkyl, carboxaryl, aryalkyl, thio and hydroxyl.

Uses of the Novel Stabilized Structures of the Present Invention

The novel stabilized structures, libraries, and methods for making said novel stabilized structures of the present invention can be utilized in various disciplines. Any available method may be employed to screen the libraries produced according to the present invention to identify those with desirable characteristics for a selected application.

To give just a few examples, the present invention can be used to produce novel stabilized structures that control (i.e., promote or inhibit) cell functions. Such compounds may be formulated and utilized as therapeutic pharmaceuticals. For example, such therapeutic pharmaceuticals, through interactions with cellular receptors, can control cell proliferation, viral replication, gene expression, or any other cell signaling process.

Figure 15:
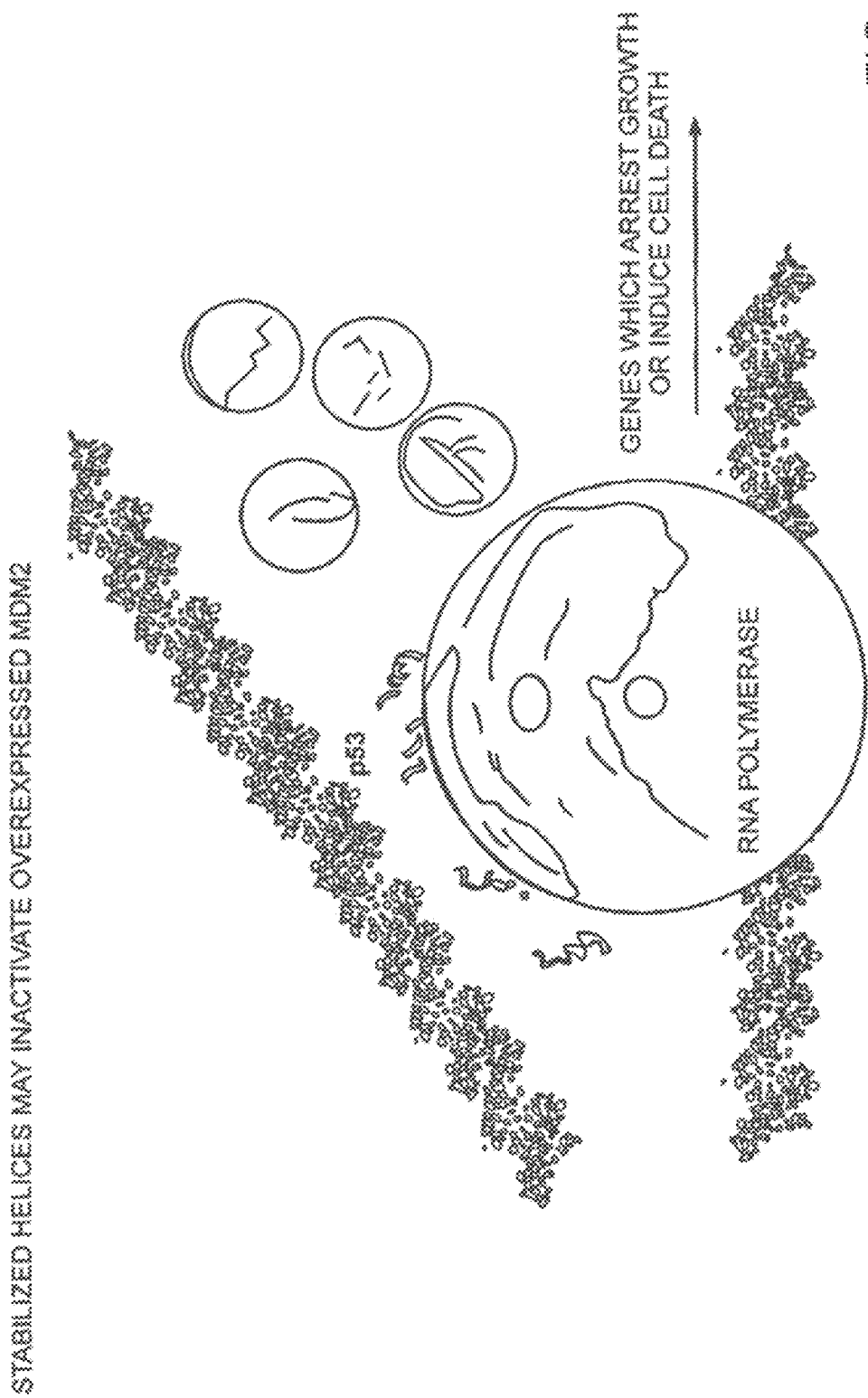
FIG. 15 depicts that stabilized helices may inactivate overexpressed MDM2.
Figure 16:
FIG. 16 depicts exemplary stabilized compounds for use in the P53/Mdm2. P53-wt is represented by SEQ ID NO:10; P53-1 is represented by SEQ ID NO:11; and P53-2 is represented by SEQ ID NO:12.
Figure 17:
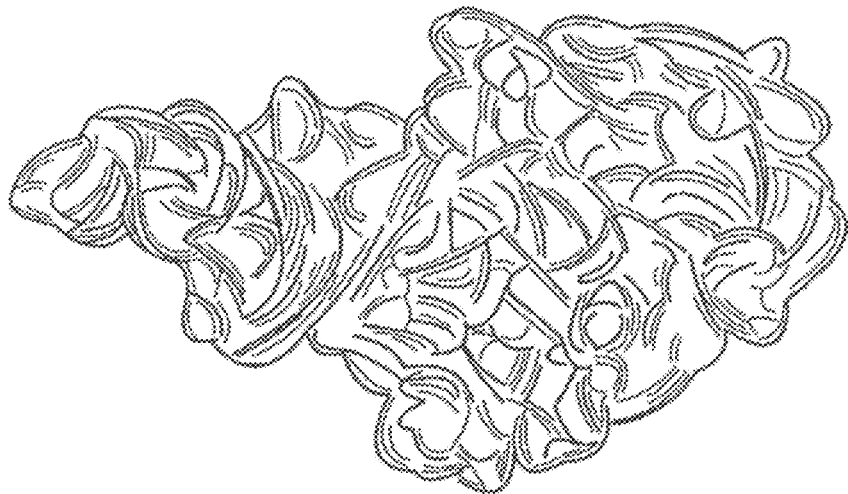
FIG. 17 depicts exemplary stabilized compounds for use in the Bak/Bcl-xL system. Bak-wt is represented by SEQ ID NO:5; Bak-1 is represented by SEQ ID NO:6; Bak-2 is represented by SEQ ID NO:7; Bak-3 is represented by SEQ ID NO:8; and Bak-4 is represented by SEQ ID NO:9.
Figure 18:
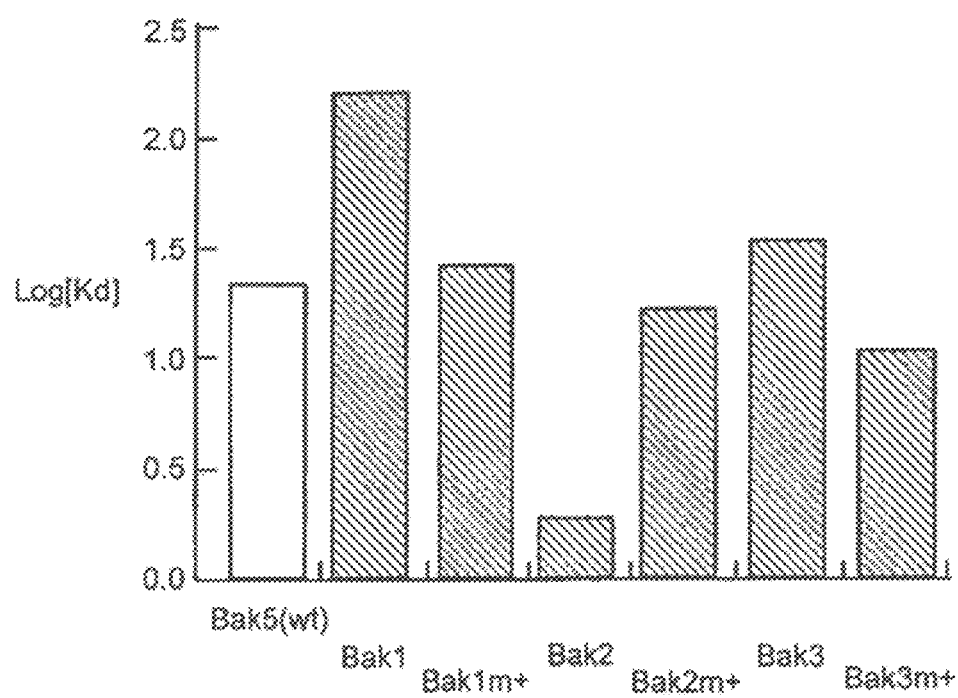
FIG. 18 depicts the binding of Bak peptides to Bcl-$x_L$.

More specifically, as mentioned above, many biologically important protein/protein interactions, such as p53/MDM2 (see FIGS. 15 and 16) and Bcl-X1/Bak (see FIGS. 17 and 18) are mediated by one protein donating a helix into a cleft of its helix-accepting partner. The interaction of p53 and MDM2 has been discussed in detail (see, Shair "A Closer View of an Oncoprotein-tumor Suppressor Interaction, *Chem. & Biol.* 1997, 4, 791, the entire contents of which are incorporated herein by reference) and mutations in the p53 gene have been identified in virtually half of all reported cancer cases. As stresses are imposed on a cell, p53 is believed to orchestrate a response that leads to either cell-cycle arrest and DNA repair, or programmed cell death. As well as mutations in the p53 gene that alter the function of the p53 protein directly, p53 can be altered by changes in MDM2. The MDM2 protein has been shown to bind to p53 and disrupt transcriptional activation by associating with the transactivation domain of p53. For example, an 11 amino-acid peptide derived from the transactivation domain of p53 forms an amphipathic α-helix of 2.5 turns that inserts into the MDM2 crevice. Thus, novel alpha helix structures generated by the method of the present invention can be engineered to generate structures that may bind tightly to the helix acceptor and disrupt native protein-protein interactions. These structures may then be screened using high throughput techniques to identify optimal small molecule peptides. The novel structures that disrupt the MDM2 interaction might be useful for many applications, including, but not limited to, control of soft tissue sarcomas (which overexpresses MDM2 in the presence of wild type p53). These cancers may be held in check with small molecules that could intercept MDM2, thereby preventing suppression of p53. Additionally, small molecules disrupters of MDM2-p53 interactions could be used as adjuvant therapy to help control and modulate the extent of the p53 dependent apoptosis response in conventional chemotherapy. FIG. 15 shows that stabilized helices may inactivate overexpressed MDM2 and FIG. 16 depicts novel stabilized structures to be utilized for the P53/Mdm2 system. Similarly, FIG. 17 depicts novel stabilized structures utilized for the Bak/Bcl-$x_L$ system and FIG. 18 depicts the binding of Bak peptides to Bcl-$x_L$.

In addition to the abovementioned uses, the inventive stabilized structures can be used for studies in bioinorganic chemistry or in catalysis, either as a ligand for a transition metal capable of mimicking an important biological environment, or by acting in concert with a particular transition metal catalyst to effect a desired chemical reaction.

Furthermore, the inventive stabilized structures are also useful in the area of materials science. For example, molecules such as lipids and other polymeric molecules may be attached to the terminal peptide moieties and thus generate potentially important biomaterials.

It will be appreciated by one of ordinary skill in the art that the present invention is not intended to be limited to the abovementioned uses, but rather may be employed in many suitable contexts and disciplines.

Peptides are excellent protein ligands, both for their tight binding and for the ease by which can be discovered using diversity based techniques. On the other hand, peptides are poor therapeutics because of their low membrane permeability and susceptibility to protease cleavage. To enhance the bioavailability of short α-helical peptides, we have developed a chemical system wherein all-hydrocarbon covalent crosslinks are installed across one and two turns of an α-helix using olefin metathesis chemistry. By screening crosslinker position, stereochemistry and crosslinker length, we have determined the optimal crosslinking geometry for maximum metathesis yield and maximum helix-stabilization in a model system. The installation of this optimal crosslink system enhances the helix content of a model peptide from 41% to 85%, which is comparable to the best helix enhancement seen in other systems. Installation of this crosslink system also enhances resistance to trypsin cleavage by over 40-fold when compared to the unmodified control peptide.

Peptides that bind macromolecular receptors in an extended conformation can often be converted to mimetics that retain binding but have improved protease resistance and membrane permeability[1]. However, peptides that must fold upon themselves in order to bind a receptor have proven difficult to improve by similar approaches, because of their larger size and the difficulty of mimicking functionality presented on a complex folded molecular surface. One such folded peptide structure that participates widely in biomolecular recognition events is the α-helix[2,3]. Most peptides that bind their receptors in an α-helical conformation have little helical structure when free in solution. Stabilizing the helical form of such peptides is thus expected to favor receptor binding by virtue of preorganization. Furthermore, the intramolecular hydrogen bonding associated with helix formation reduces the exposure of the polar amide backbone, thereby reducing the barrier to membrane penetration and increasing the resistance to protease cleavage.

A number of approaches for covalent helix-stabilization have been reported[4], but most involve crosslinks that are both polar and pharmacologically labile, such as disulfides[5] and lactam bridges[6,7]. An important conceptual advance on this front is the development by Grubbs and co-workers of chemistry for olefinic crosslinking of helices through 0-allyl serine residues located on adjacent helical turns, via ruthenium-catalyzed ring closing metathesis (RCM)[8]. The particular crosslinks analyzed in that study, however, showed no evidence of enhancing helical stability, highlighting the difficulty of this problem from a design standpoint. Here we have taken an alternate metathesis-based approach, namely to screen multiple configurations of all-hydrocarbon crosslinks differing in position of attachment, stereochemistry, and crosslinker length. Where some configurations impart significant helix-stabilization, others actually destabilize the helix. We show that stabilizing an α-helix in this way leads to markedly increased resistance to proteolysis.

Figure 19:
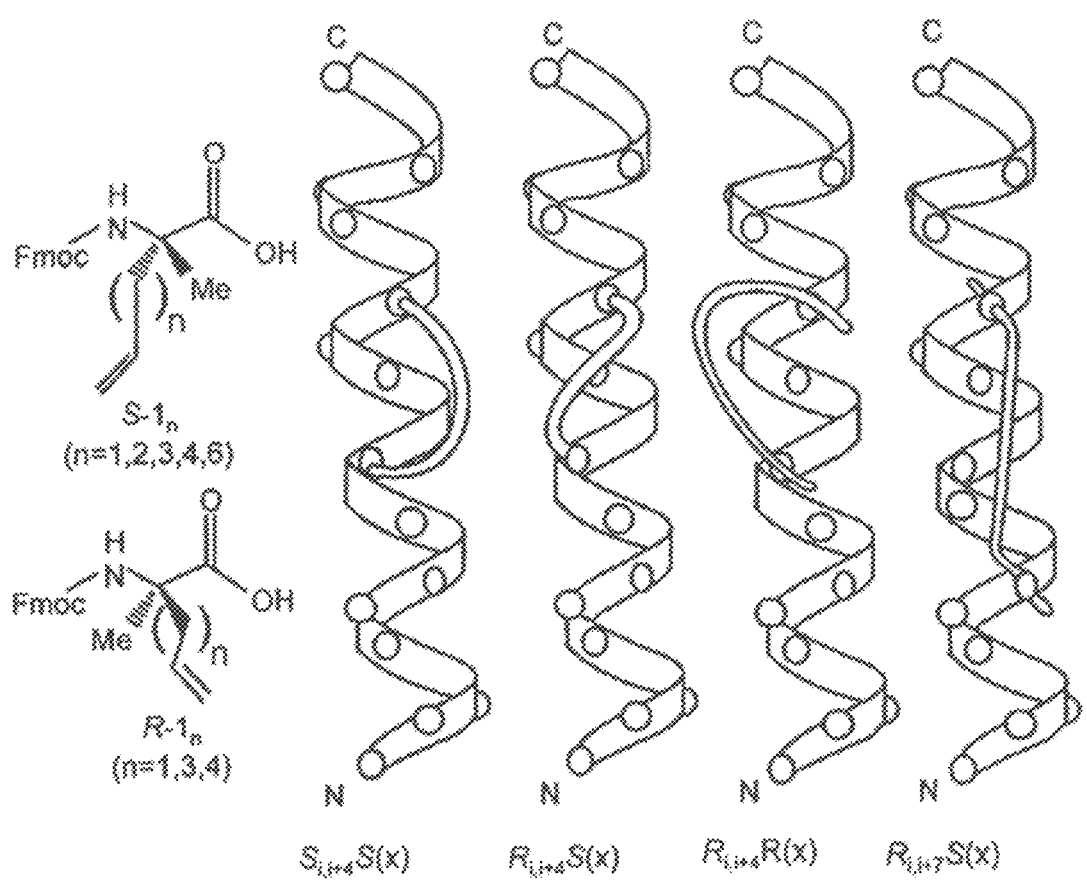
FIG. 19 depicts a strategy for stabilizing α-helices through an all-hydrocarbon crosslinking system. The key components of the system are α-methylated amino acids 1, bearing olefinic side-chains of varying length and configured with either R or S stereochemistry. These are incorporated into peptides at the i and either i+4 or i+7 position, and then connected via olefin metathesis to crosslink one or two turns, respectively, of the helix. The overall side-chain length of 1=n+2, and of the crosslinks=n+n+2. The nomenclature Ri,i+7S(11) refers to a peptide with an R and an S configurated amino acid at positions "i", and "i+7" respectively, and 11 carbons in the metathesized crosslink.

The actual structure of crosslinks positioned on one face of an α-helix is very dependent upon the stereochemistry at the attachment points (FIG. 19). We therefore designed unnatural amino acids 1 having either R or S stereochemistry at the α-carbon, and bearing alkyl tethers of various lengths (FIG. 19). To avoid the intrinsic helix-destabilizing effect of D-configured amino acids while capitalizing on the helix-stabilizing effect of α,α-disubstituted amino acids we introduced an α-methyl group into 1. We incorporated these synthetic amino acids across either one or two turns (i and i+4, or i+7 position, respectively; FIG. 19) of the C-peptide sequence from Rnase A[9]; this particular peptide was chosen because it exhibits partial helicity in water, allowing us to observe both increases and decreases in helical content owing to modifications[10].

None of the peptides in the $R_{i,i+4}S(x)$ series (x=5, 6, 7) underwent metathesis to any measurable extent. In the $R_{i,i+4}R(x)$ series, the peptide having a 6-carbon crosslink (x=6) failed to metathesize, but that having a 7-carbon crosslink (x=7) formed to the extent of 17%, and the metathesis reaction leading to the 8-carbon crosslinked peptide (x=8) went to completion (>98%) (Table 1). In the $S_{i,i+4}S(x)$ series, the shortest member (x=6) again failed to undergo RCM, but the longer versions, x=7 and 8, underwent 68% and >98% conversion, respectively. In the $R_{i,i+7}S(x)$ series the crosslinks were again formed with increasing efficiency as they became longer (x=8, <5%; x=9, 51%; 10, 77%; 11, >98%; 12, >98%). Two general trends are evident from these reactions. First, the conversions by RCM increase as a function of increasing ring size in the macrocyclic crosslink. Indeed, the 34-membered macrocycle in $S_{i,i+7}R(12)$ is formed rapidly and efficiently, despite being one of the largest macrocycles closed by RCM to date[11]. Second, small changes in ring size can cause dramatic effects on the efficiency of crosslinking; for example, the 30-membered macrocycle in $R_{i,i+7}S(8)$ fails to form appreciably, whereas the 31-membered ring of $R_{i,i+7}S(9)$ forms to the extent of 50%. We believe both effects can be explained by templating of the RCM reaction through helix induction of the unmetathesized precursor peptides on the solid support in the solvent dichloroethane. According to this explanation, tethers that are too short to span the gap along the face of the templating helix are not metathesized efficiently.

Figure 20:
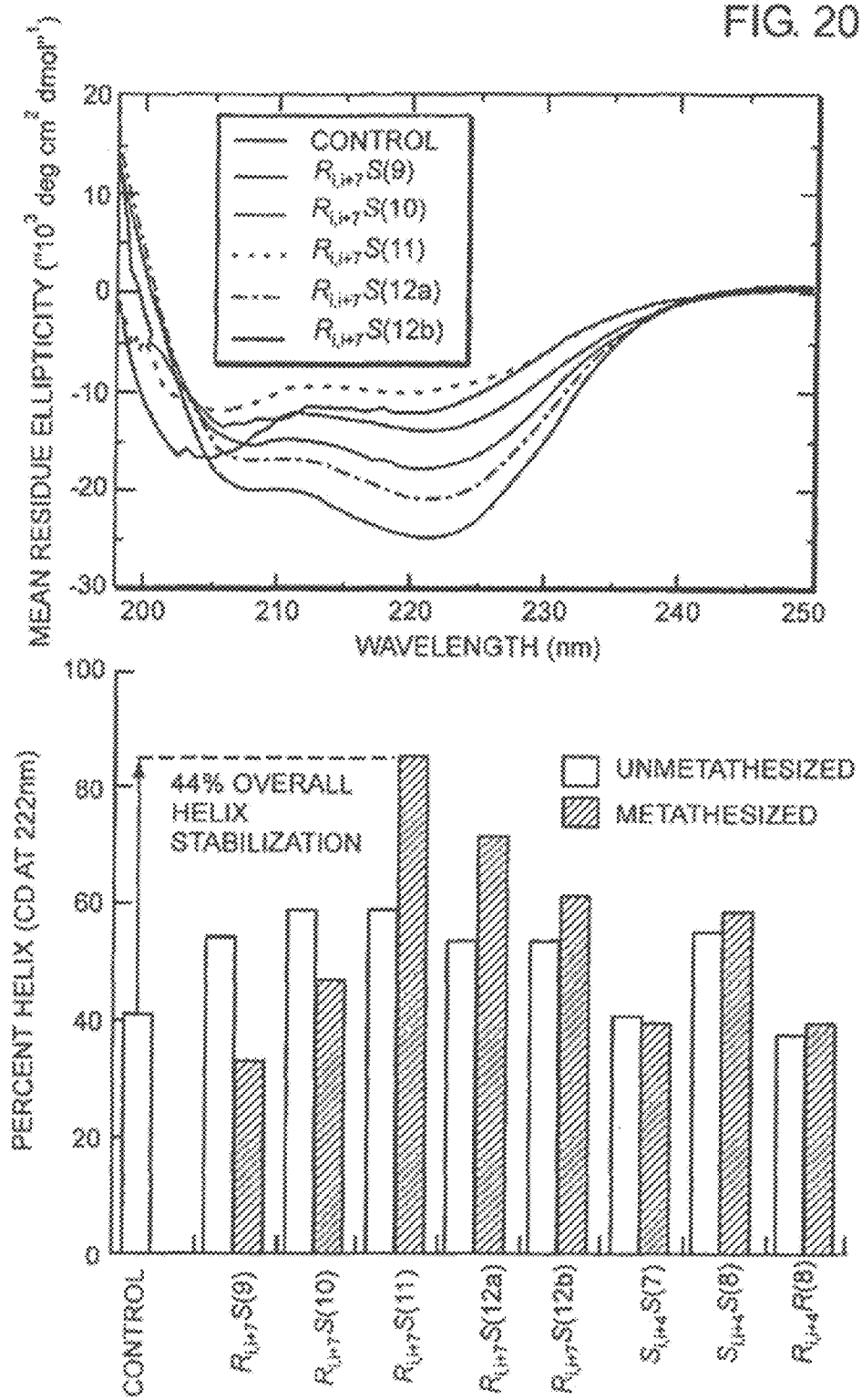
FIG. 20. (A) Different crosslinks destabilize and stabilize the helix to different extents in the Ri,i+7S series. (B) In the Ri,i+7S series α-methyl amino acids increase helical structure by ca. 15%. Inducing a crosslink using olefin metathesis has an effect on helicity that depends on the crosslink length. Ri,i+7S(11) is the best helix stabilizer. The uncertainties in these measurements are no greater than +/−5%.
Figure 21:
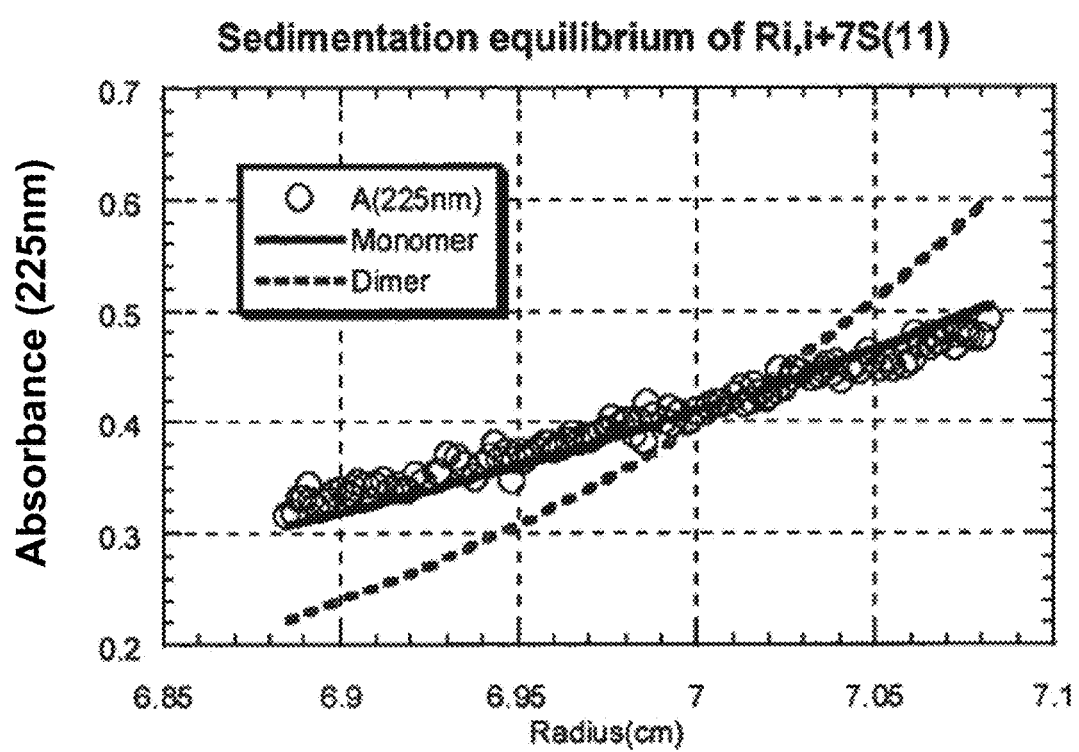
FIG. 21 depicts data relating to the sedimentation equilibrium of Ri,i+7S(11). The graph depicts the experimentally observed absorbance at 225 nm of Ri,i+7S(11) (open circles), the calculated absorbance at 225 nm of a corresponding idealized monomeric peptide (solid line), and the calculated absorbance at 225 nm of a corresponding idealized dimeric peptide (dashed line); all data is presented as a function of the radius of the sample. The experimental data fits the calculated data for the idealized monomeric peptide.

To determine the effect of olefinic crosslinking on the helical propensity of the peptides, we used circular dichroism to provide a quantitative measure of helical content[12] (FIG. 20). As a benchmark, the control unmodified RNase A peptide is ~40% α-helical in water containing 0.1% trifluoroacetic acid at 4° C. All peptides that underwent RCM to the extent of ~50% or more were measured in both uncrosslinked and crosslinked forms. In most cases, and as expected[13], inclusion of the two αα-disubstituted amino acids into the peptide increased its helical content with respect to the unmodified control. In the i,i+4 peptide series, crosslinking neither stabilized nor destabilized the helix with respect to the corresponding uncrosslinked modified peptide; the reasons for this effect are not apparent from inspection of models. RCM crosslinking of the modified i,i+7 peptides produced effects ranging from 21% destabilization to significant stabilization of α-helical structure. Specifically, the helical content of the $R_{i,i+7}S(9)$ and (10) peptides decreased by 21% and 12% following RCM, whereas that of the $R_{i,i+7}S(11)$ peptide increased by 26%. Crosslinking of the $R_{i,i+7}S(12)$ peptide produced cis and trans double bond isomers one of which was more stabilizing than the other (18% vs 7%)[14]. The overall trends seen in the $R_{i,i+7}S$ series can be rationalized as follows: crosslinks of 9 and 10 carbons are too short to permit the formation of an unstrained helix, 11 carbons provides the optimal fit, and 12 carbons are longer than necessary and therefore do not constrain the helix as effectively as the 11 carbon crosslink. Importantly, the introduction and crosslinking of two modified amino acids as an 11 atom hydrocarbon chain stabilizes the helix by 44% when compared to an unmodified control peptide, an extent that is comparable to the best seen with other crosslinking systems[6]. As determined by sedimentation equilibrium, all of the peptides were monomeric under the conditions of the circular dichroism experiments, indicating that the helix induction is not due to aggregation[15].

To assess the effect of the olefin in the crosslink on helix-stability, we reduced the double bonds in the $R_{i,i+7}S$ series by transfer hydrogenation on the solid phase[16,17], purified the saturated, crosslinked peptides and determined their helical content by CD. Remarkably, the helical properties of the entire hydrogenated $R_{i,i+7}S(9-12)$ peptide series was indistinguishable from that of the corresponding olefin containing peptides.

Cleavage by proteases is one of the main pathways for inactivation of peptides in a biological setting. As all known proteases bind their substrates in an extended rather than helical conformation, inducing helical structure is expected to confer protease stability, leading to increased potency in vivo. As an in vitro test of this concept, we took advantage of the fact that the crosslinked stretch of our peptides contains a lysine residue, which can be targeted by the protease trypsin. As expected, the unmodified control peptide is highly susceptible to cleavage by trypsin (k=2.38 $M^{-1} s^{-1}$) (Table 2). Incorporation of the two unnatural amino acids at the i and i+7 positions, without crosslinking, decreases the cleavage rate by almost 5 fold, consistent with the helix-stabilizing effects noted above. Metathesis and subsequent hydrogenation produced a further stabilization, the magnitude of which is markedly dependent on the length of the crosslink. The extent of this crosslink-dependent stabilization precisely mirrored the extent of helix induction, being most pronounced for the $R_{i,i+7}S(11)$ peptide. Overall, the incorporation of the crosslink unit stabilizes this peptide toward trypsin digestion by 41 fold.

The major goal of this research program is to improve the pharmacological properties of α-helical peptides through synthetic modification. The present report is an important first step toward that end. Here we show that an all-hydrocarbon crosslinking system can greatly increase the helical propensity and metabolic stability of peptides.

Experimental Procedures

General: $^1H$ (400 MHz) and $^{13}C$ (100 MHz) NMR spectra were measured in DMSO-$d_6$ using tetramethylsilane as the standard for $^1H$ NMR and the solvent resonance (39.5 ppm) for $^{13}C$ NMR. Mass spectral data were obtained at the Harvard Mass Spectrometry Facility.

Synthesis of Boc protected α-methyl, α-alkenyl amino acids: The synthesis is as described by Williams[1] for Boc protected α-methyl, α-allyl amino acid with the following modifications. The second alkylation with allyl-iodide as the electrophile was performed at −78° C. The second alkylation, with 4-iodo-1-butene, 5-iodo-1-pentene, 6-iodo-1-hexene, or 8-iodo-1-hexene as the electrophile was performed at −40° C. (MeCN/$N_2$ (liquid)) with 3 equivalents of the electrophile and the reaction was stirred for 30 min after the dropwise addition of potassium bis(trimethylsilyl)amide. The second alkylation, when it involved the electrophile 4-iodo-1-butene resulted in lower yields (45%) presumably due to competing elimination of the 4-iodo-1-butene to 1,3-butadiene. Deblocking of the α,α disubstituted amino acids was performed using the sodium in liquid ammonia hydrogenolysis described as described by Williams[1].

Deprotection of the Boc protected α-methyl, α-alkenyl amino acids and acetylation with 9-fluorenylmethyl carbamate: The Boc protected α-methyl, α-alkenyl amino acid was dissolved in $CH_2Cl_2$ (to yield a concentration of 500 mM) and cooled to 0° C. To this solution, an equal volume of trifluoroacetic acid was added and the solution is allowed to stir for 30 min. The product was concentrated on a rotovap fitted with a dry ice/acetone cold finger to trap TFA. The residue is dried on high vacuum until it contained less than 2 equivalents of residual TFA by weight. To this residue was added a 50% water/acetone solution to 300 mM final concentration of amino acid, 3 equivalents of $Na_2CO_3$ and 1.05 equivalents of Fmoc-N-hydroxy-succinimide. The nonhomogenous mixture was stirred for 12 hours at room temperature. The mixture was then acidified to pH 3 using hydrochloric acid and extracted three times with ethyl acetate. The combined ethyl acetate extracts were then dried over anhydrous sodium sulfate, concentrated, and purified using flash chromatography using MeOH:$CH_2Cl_2$:AcOH (3:96:1).

(S)-N-(9-Fluorenylmethyl carbamate)-2-(2'-propenyl)alanine ("Fmoc-$S_{1_1}$"). $^1H$-NMR (400 MHz, DMSO-$d_6$) δ 7.90 (d, J=7.6 Hz, 2H), 7.73 (d, J=7.2 Hz, 2H), 7.42 (t, J=7.2 Hz, 2H), 7.34 (t, J=7.2 Hz, 2H), 5.70 (m, 1H), 5.07 (m, 2H), 4.25 (m, 3H), 2.65 (dd, J=13.6 Hz, J=7.2 Hz, 1H), 2.41 (dd, J=13.6 Hz, J=7.6 Hz, 1H), 1.30 (s, 3H); $^{13}C$-NMR (100 MHz, DMSO-$d_6$) δ 174.7, 154.5, 143.6, 140.5, 133.0, 127.4, 126.9, 125.1, 119.9, 118.4, 65.2, 57.8, 46.7, 22.4, 21.1; HRMS calcd for $C_{21}H_{21}NO_4$ (M+Na) 352.1549, found 352.1561.

(S)-N-(9-Fluorenylmethyl carbamate)-2-(2'-butenyl)alanine ("Fmoc-$S_{1_2}$"). $^1H$-NMR (400 MHz, DMSO-$d_6$) δ 7.90 (d, J=7.2 Hz, 2H), 7.73 (d, J=7.6 Hz, 2H), 7.42 (t, J=7.2 Hz, 2H), 7.33 (t, J=7.6 Hz, 2H), 5.79 (m, 1H), 5.01 (d, J=17.2 Hz, 1H), 4.95 (d, J=10.4 Hz, 1H), 4.25 (m, 3H), 1.93 (m, 3H), 1.75 (m, 1H), 1.35 (s, 3H); $^{13}C$-NMR (100 MHz, DMSO-$d_6$) δ 175.1, 154.6, 143.7, 140.6, 138.1, 127.5, 127.0, 125.2, 120.0, 118.4, 65.2, 58.1, 46.7, 35.6, 27.7, 22.4; HRMS calcd for $C_{22}H_{23}Na_4$ (M+H) 366.1705, found 366.1709.

(S)-N-(9-Fluorenylmethyl carbamate)-2-(2'-pentenyl)alanine ("Fmoc-$S_{1_3}$"). $^1H$-NMR (400 MHz, DMSO-$d_6$) δ 7.894 (d, J=7.6 Hz, 2H), 7.723 (d, J=7.2 Hz, 2H), 7.418 (t, J=8 Hz, 2H), 7.330 (td, J=7.2 Hz, J=1.2 Hz, 2H), 5.775 (m, 1H), 5.001 (dd, J=17.2 Hz, J=1.2 Hz, 1H), 4.955 (dd, J=10.4 Hz, J=1.2 Hz, 1H), 4.229 (m, 3H), 1.994 (t, J=6.4 Hz, 2H), 1.764 (m, 1H), 1.665 (m, 1H), 1.326 (br, 5H); $^{13}C$-NMR (100 MHz, DMSO-$d_6$) δ 175.1, 154.5, 143.6, 140.5, 138.3, 127.4, 126.9, 125.1, 119.9, 114.8, 65.2, 58.2, 46.7, 36.3, 33.3, 22.6, 22.4; HRMS calcd for $C_{23}H_{25}NO_4$ (M+Na) 402.1682, found 402.1678.

(S)-N-(9-Fluorenylmethyl carbamate)-2-(2'-hexenyl)alanine ("Fmoc-$S_{1_4}$"). $^1H$-NMR (400 MHz, DMSO-$d_6$) δ 7.87 (d, J=7.6 Hz, 2H), 7.70 (d, J=7.2 Hz, 2H), 7.40 (t, J=7.2 Hz, 2H), 7.31 (t, J=7.2 Hz, 2H), 5.75 (m, 1H), 4.97 (dd, J=17.2 Hz, J=2 Hz, 1H), 4.91 (dt, J=10 Hz, J=1.2 Hz, 1H), 4.22 (m, 3H), 1.98 (m, 2H), 1.75 (m, 1H), 1.66 (m, 1H), 1.31 (m, 4H), 1.20 (s, 3H); $^{13}C$-NMR (100 MHz, DMSO-$d_6$) δ 175.5, 154.5, 143.6, 140.5, 138.4, 127.4, 126.9, 125.1, 119.9, 114.7, 65.2, 58.2, 46.7, 36.5, 33.2, 28.5, 22.8, 22.4; HRMS calcd for $C_{24}H_{27}NO_4$ (M+Na) 416.1838, found 416.1848.

(S)-N-(9-Fluorenylmethyl carbamate)-2-(2'-octenyl)alanine ("Fmoc-$S_{1_6}$"). $^1H$-NMR (400 MHz, DMSO-$d_6$) δ 7.89 (d, J=8 Hz, 2H), 7.72 (d, J=7.2 Hz, 2H), 7.42 (t, J=7.2 Hz, 2H), 7.33 (td, J=7.2 Hz, J=0.8 Hz, 2H), 5.78 (m, 1H), 4.98 (d, J=17 Hz, 1H), 4.93 (d, J=10 Hz, 1H), 4.23 (m, 3H), 1.99 (dt, J=7.2 Hz, J=6.8 Hz, 2H), 1.76 (m, 1H), 1.68 (m, 1H), 1.33 (br, 4H), 1.23 (br, 7H); $^{13}$C-NMR (100 MHz, DMSO-d$_6$) δ 175.0, 154.5, 143.6, 140.5, 138.5, 127.4, 126.8, 125.1, 119.9, 114.4, 65.2, 58.2, 46.7, 36.6, 33.2, 29.0, 28.4, 28.2, 23.1, 22.4; HRMS calcd for C$_{26}$H$_{31}$NO$_4$ (M+Na) 444.2151, found 444.2151.

(R)-N-(9-Fluorenylmethyl carbamate)-2-(2'-propenyl)alanine ("Fmoc-R-1$_1$"). $^1$H-NMR (400 MHz, DMSO-d$_6$) δ 7.90 (d, J=7.6 Hz, 2H), 7.73 (d, J=7.2 Hz, 2H), 7.42 (t, J=7.2 Hz, 2H), 7.34 (t, J=6.4 Hz, 2H), 5.69 (m, 1H), 5.06 (m, 2H), 4.25 (m, 3H), 2.65 (dd, J=13.6 Hz, J=6.8 Hz, 1H), 2.42 (dd, J=13.2 Hz, J=7.6 Hz, 1H) 1.30 (s, 3H); $^{13}$C-NMR (100 MHz, DMSO-d$_6$) δ 174.7, 154.5, 143.6, 140.5, 133.0, 127.4, 126.9, 125.1, 119.9, 118.4, 65.2, 57.8, 46.7, 22.4, 21.1; HRMS calcd for C$_{21}$H$_{21}$NO$_4$ (M+Na) 374.1369, found 374.1373.

(R)-N-(9-Fluorenylmethyl carbamate)-2-(2'-pentenyl)alanine ("Fmoc-R-1$_3$"). $^1$H-NMR (400 MHz, DMSO-d$_6$) δ 7.90 (d, J=7.6 Hz, 2H), 7.73 (d, J=7.6 Hz, 2H), 7.42 (t, J=7.6 Hz, 2H), 7.33 (t, J=7.6 Hz, 2H), 5.78 (m, 1H), 5.00 (d, J=17.6 Hz, 1H), 4.96 (d, J=10.4 Hz, 1H), 4.24 (m, 3H), 1.99 (m, 2H), 1.78 (m, 1H), 1.68 (m, 1H), 1.33 (br, 5H); $^{13}$C-NMR (100 MHz, DMSO-d$_6$) δ 175.1, 154.5, 143.6, 140.5, 138.3, 127.4, 126.9, 125.1, 119.9, 114.8, 65.2, 58.2, 46.7, 36.2, 33.3, 22.6, 22.4; HRMS calcd for C$_{23}$H$_{25}$NO$_4$ (M+H) 380.1862, found 380.1881.

(R)-N-(9-Fluorenylmethyl carbamate)-2-(2'-hexenyl)alanine ("Fmoc-R-1$_4$"). $^1$H-NMR (400 MHz, DMSO-d$_6$) δ 7.90 (d, J=7.2 Hz, 2H), 7.73 (d, J=7.2 Hz, 2H), 7.42 (t, J=7.6 Hz, 2H), 7.33 (t, J=7.2 Hz, 2H), 5.76 (m, 1H), 5.00 (dd, J=17.2 Hz, J=2 Hz, 1H), 4.94 (dt, J=10.4 Hz, J=0.8 Hz, 1H), 4.24 (m, 3H), 2.02 (br, 2H), 1.77 (m, 1H), 1.68 (m, 1H), 1.32 (br, 4H), 1.23 (br, 3H); $^{13}$C-NMR (100 MHz, DMSO-d$_6$) δ 175.1, 154.5, 143.6, 140.5, 138.4, 127.4, 126.9, 125.1, 119.9, 114.6, 65.2, 58.2, 46.7, 36.5, 33.2, 28.5, 22.7, 22.4; HRMS calcd for C$_{24}$H$_{27}$NO$_4$ (M+Na) 416.1838, found 416.1823.

Peptide Synthesis: The peptides were synthesized manually, using solid phase peptide and Fmoc chemistry on Rink Amide AM resin with a loading of 0.65 mmol/g resin. α,α-Di-substituted amino acids were coupled using O-(7-azabenzotriazol-1-yl)-1,1,3,3-tetramethyluronium hexafluorophosphate (HATU) as the activating agent, three equivalents of the amino acid, and coupling times were typically two hours. The following amino acid coupled to the free amine of the α,α-di-substituted amino acids was double coupled using HATU. The peptides were cleaved using standard protocols, purified using C18 reverse phase chromatography and their identities were confirmed using electrospray mass spectroscopy. The wild type peptide has the sequence: Ac-EWAETAAAKFLAAHA-NH$_2$ (SEQ ID NO: 1). The peptides synthesized in the R$_{i,i+7}$S(x) series have the general sequence: Ac-EWAEyAAAKFLzAHA-NH$_2$ (SEQ ID NO: 2) where (y,z) were substituted with the unnatural amino acid pairs (R-1$_3$,S-1$_3$), (R-1$_3$,S-1$_4$), (R-1$_4$,S-1$_4$), (R-1$_3$,S-1$_6$), and (R-1$_4$,S-1$_6$) for the peptides R$_{i,i+7}$S(8), R$_{i,i+7}$S(9), R$_{i,i+7}$S(10), R$_{i,i+7}$S(11), and R$_{i,i+7}$S(12) respectively. The peptides synthesized in the S$_{i,i+4}$S(x), R$_{i,i+4}$R(x), and R$_{i,i+4}$S(x) series have the general sequence: Ac-EWAETAAyKFLzAHA-NH$_2$ (SEQ ID NO: 3) where (y,z) were substituted with the unnatural amino acid pairs (S-1$_1$,S-1$_3$), (S-1$_1$,S-1$_4$), (S-1$_3$,S-1$_3$), (R-1$_1$,R-1$_3$), (R-1$_1$,R-1$_4$), (R-1$_3$,R-1$_3$), (R-1$_1$,S-1$_2$), (R-1$_1$,S-1$_3$), and (R-1$_1$,S-1$_4$) for the peptides S$_{i,i+4}$S(6), S$_{i,i+4}$S(7), S$_{i,i+4}$S(8), R$_{i,i+4}$S(6), R$_{i,i+4}$S(7), R$_{i,i+4}$S(8), R$_{i,i+4}$S(5), R$_{i,i+4}$S(6), and R$_{i,i+4}$S(7) respectively. Ac and NH$_2$ represent N-terminal acetylation and a C-terminal primary amide respectively.

Peptide metathesis and purification: 200 μL of 10 mM Bis(tricyclohexylphosphine)benzylidine ruthenium (IV) dichloride (Grubbs catalyst) in 1,2-dichloroethane was degassed and added to 20 mg of N-terminal capped peptide still bound to the solid support in a disposable fritted reaction vessel. The reaction was allowed to proceed at room temperature for two hours and then the catalyst was filtered off. The catalyst addition and 2 hour metathesis reaction was repeated once to drive the slow metathesis reactions to completion. The resin bound peptide was then washed, dried and cleaved according to standard Fmoc peptide cleavage protocols (95% TFA, 2.5% H$_2$O, 2.5% triisopropylsilane)[19]. The cleaved peptides are purified using C$_{18}$ reverse phase HPLC. All of the metathesized peptides elute before the unmetathesized starting material.

Olefin hydrogenation on solid support: Hydrogenation of olefin containing peptides on solid support was performed by adding 200 μL of a solution of 0.7 M 2,4,6 tri-isopropyl benzenesulfonyl hydrazide and 1.4 M piperidine in 1-methyl-2-pyrrolidinone to 20 mg of olefin containing peptide on solid support in a disposable fritted reaction vessel. The vessel was sealed and placed in a 47° C. water bath for two hours. After two hours the solution was filtered off and the hydrazine addition and reaction at 47° C. is repeated four more times. The progress of the reaction can be monitored by injecting the cleavage product of a few beads into an electrospray reverse phase LC mass spectrometer or by reverse phase HPLC monitored at 280 nm. The retention time of the hydrogenated peptides falls between the metathesized, unhydrogenated peptides and the unmetathesized peptides.

Circular dichroism: Circular dichroism spectra were collected on a Jasco J-710 spectropolarimeter at 4° C. A typical sample was prepared by lyophilizing a measured volume of peptide solution and then resuspending it in 3 ml of 0.1% TFA in water to obtain a solution with a 280 nm absorbance of approximately 0.06 absorbance units. The sample was placed in a 1 cm CD cuvette and the ultraviolet absorbance was measured. The circular dichroism spectrum was measured and a baseline CD spectrum of 0.1% TFA in water was subtracted from it. The baseline subtracted CD spectrum was then normalized using the 280 nm absorbance.

Analytical centrifugation: Sedimentation Equilibrium Experiments were performed on a Beckman Optima XL-A analytical centrifuge. The samples were centrifuged at 35,000 RPM at 4° C. and monitored at 280 nm. The data was fit to a single species model. The sedimentation equilibrium experiments were run on the identical samples from which circular dichroism spectra were recorded. All of the peptides fit to an ideal monomer indicating that the helix induction seen is not due to aggregation.

Peptide trypsin digest: A typical peptide trypsin digest experiment was performed by adding 5 μL of a 20× trypsin solution in 1 mM HCl to a 100 μL solution of peptide at 9 μM in 10% EtOH in 50 mM Tris at pH 8.3. The reaction was allowed to proceed at room temperature for 30 min at which time it was quenched by adding 100 μL of a 1% trifluoroacetic acid solution and frozen on dry ice. The sample was then thawed and injected into a reverse phase HPLC on a C18 column for quantitation at 280 nm. The cleavage rate constants were obtained by performing the digest experiments at multiple trypsin concentrations and fitting to a kinetic model that is first order in both enzyme and substrate concentration.

REFERENCES AND NOTES

1) Gante, J. *Angew. Chem. Int. Ed. Engl.* 1994, 33, 1699-1720.

2) Sattler, M.; Liang, H.; Nettesheim, D.; Meadows, R. P.; Harlan, J. E.; Eberstadt, M.; Yoon, H. S.; Shuker, S. B.; Chang, B. S.; Minn, A. J.; Thompson, C. B.; Fesik, S. W. *Science* 1997, 275, 983-6.

3) Kussie, P. H.; Gorina, S.; Marechal, V.; Elenbaas, B.; Moreau, J.; Levine, A. J.; Pavletich, N. P. *Science* 1996, 274, 948-53.

4) Andrews, M. J. I.; Tabor, A. B. *Tetrahedron* 1999, 55, 11711-11743.

5) Jackson, D. Y.; King, D. S.; Chmielewski, J.; Singh, S.; Schultz, P. G. *J. Am. Chem. Soc.* 1991, 113, 9391-9392.

6) Phelan, J. C.; Skelton, N. J.; Braisted, A. C.; McDowell, R. S. *J. Am. Chem. Soc.* 1997, 119, 455-460.

7) Bracken, C.; Gulyas, J.; Taylor, J. W.; Baum, J. *J. Am. Chem. Soc.* 1994, 116, 6431-6432.

8) Blackwell, H. E.; Grubbs, R. H. *Angew. Chem. Int. Edn. Engl.* 1998, 37, 3281-3284.

9) Bierzynski, A.; Kim, P. S.; Baldwin, R. L. *Proc. Natl. Acad. Sci USA* 1982, 79, 2470-2474.

10) The wild type peptide has the sequence: Ac-EWAETAAAKFLAAHA-NH$_2$ (SEQ ID NO: 1). The peptides synthesized in the R$_{i,i+7}$S(x) series have the general sequence: Ac-EWAEyAAAKFLzAHA-NH$_2$ (SEQ ID NO: 2) where (y,z) were substituted with the unnatural amino acid pairs (R-1$_3$,S-1$_3$), (R-1$_3$,S-1$_4$), (R-1$_4$,S-1$_4$), (R-1$_3$,S-1$_6$), and (R-1$_4$,S-1$_6$) for the peptides R$_{i,i+7}$S(8), R$_{i,i+7}$S(9), R$_{i,i+7}$S(10), R$_{i,i+7}$S(11), and R$_{i,i+7}$S (12) respectively. The peptides synthesized in the S$_{i,i+4}$S (x), R$_{i,i+4}$R(x), and R$_{i,i+4}$S(x) series have the general sequence: Ac-EWAETAAyKFLzAHA-NH$_2$ (SEQ ID NO: 3) where (y,z) were substituted with the unnatural amino acid pairs (S-1$_1$,S-1$_3$), (S-1$_1$,S-1$_4$), (S-1$_3$,S-1$_3$), (R-1$_1$,R-1$_3$), (R-1$_1$,R-1$_4$), (R-1$_3$,R-1$_3$), (R-1$_1$,S-1$_2$), (R-1$_1$,S-1$_3$), and (R-1$_1$,S-1$_4$) for the peptides S$_{i,i+4}$S(6), S$_{i,i+4}$S(7), S$_{i,i+4}$S(8), R$_{i,i+4}$R(6), R$_{i,i+4}$R(7), R$_{i,i+4}$R(8), R$_{i,i+4}$S(5), R$_{i,i+4}$S(6), and R$_{i,i+4}$S(7) respectively. Ac and NH$_2$ represent N-terminal acetylation and a C-terminal primary amide respectively.

11) Clark, T. D.; Ghadiri, M. R. *J. Am. Chem. Soc.* 1995, 117, 12364-12365.

12) Greenfield, N.; Fasman, G. D. *Biochemistry* 1969, 8, 4108-4116.

13) Kaul, R.; Balaram, P. *Bioorganic and Medicinal Chemistry* 1999, 7, 105-117.

14) C18 reverse phase HPLC of R$_{i,i+7}$S(12) shows two separable product peaks (a) and (b) that have identical molecular masses (1760 Daltons). Peak (a) has an NMR peak at ($\delta$=5.49) and peak (b) has an NMR peak at ($\delta$=5.52). Hydrogenated R$_{i,i+7}$S(12) is a single peak by reverse phase C18 HPLC.

15) See "Analytical Centrifugation" in supporting information.

16) Lacombe, P.; Castagner, B.; Gareau, Y.; Ruel, R. *Tetrahedron Letters* 1998, 39, 6785-6786.

17) Cusack, N. J.; Reese, C. B.; Risius, A. C.; Roozpeikar, B. *Tetrahedron* 1976, 32, 2157-2162.

18) Williams, R. M.; Im, M. *J. Am. Chem. Soc.* 1991, 113, 9276-9286.

19) Novabiochem *Novabiochem Catalog & Peptide Synthesis Handbook*, 1997.

Table 1

Percent conversions for a two hour metathesis reaction performed on solid support with 10 mM Grubbs catalyst in 1,2-dichloroethane. Percent conversion product/(product+starting material) as determined by reverse phase HPLC.

TABLE 1

| Crosslink | % Conversion | Crosslink | % Conversion | Crosslink | % Conversion |
|---|---|---|---|---|---|
| R$_{i,i+7}$S(8) | 0 | S$_{i,i+4}$S(6) | 0 | R$_{i,i+4}$S(6) | 0 |
| R$_{i,i+7}$S(9) | 51 | S$_{i,i+4}$S(7) | 68 | R$_{i,i+4}$S(7) | 17 |
| R$_{i,i+7}$S(10) | 77 | S$_{i,i+4}$S(8) | >98 | R$_{i,i+4}$S(8) | >98 |
| R$_{i,i+7}$S(11) | >98 | | | | |
| R$_{i,i+7}$S(12) | >98 | | | | |

TABLE 2

| | Cleavage rate constant (M$^{-1}$ s$^{-1}$) | |
|---|---|---|
| Crosslink | Unmetathesized | Metathesized and hydrogenated |
| Control | 2.39 | |
| R$_{i,i+7}$S(9) | | 0.37 |
| R$_{i,i+7}$S(10) | | 0.34 |
| R$_{i,i+7}$S(11) | 0.50 | 0.058 |
| R$_{i,i+7}$S(12) | | 0.12 |

EQUIVALENTS

Those skilled in the art will recognize, or be able to ascertain using no more than routine experimentation, numerous equivalents to the inventive stabilized compounds and methods of use thereof described herein. Such equivalents are considered to be within the scope of this invention and are covered by the following claims.

We claim:

1. A method for disrupting the binding of a first protein to a second protein, the method comprising contacting a peptide with the second protein, wherein the first protein is a native protein; the second protein is another native protein; the second protein comprises a helix acceptor; the first protein binds the helix acceptor of the second protein; the peptide binds the helix acceptor of the second protein; the peptide comprises a stabilized alpha helix; and the peptide comprises at least two amino acids connected by a hydrocarbon covalent cross-link.

2. The method of claim 1, wherein the hydrocarbon covalent cross-link stabilizes the alpha-helix of the peptide.

3. The method of claim 1, wherein the peptide comprises a binding site of a donor helix of the first protein.

4. The method of claim 1, wherein the cross-link comprises a carbon-carbon double bond.

5. The method of claim 1, wherein the at least two amino acids connected by the hydrocarbon covalent cross-link are positioned at i,i+4 or at i,i+7.

6. The method of claim 1, wherein the at least two amino acids that are connected by the hydrocarbon covalent cross-link are alpha,alpha-methyl, vinyl; alpha, alpha-methyl, alkylolefin; or divinyl amino acids.

7. The method of claim 6, wherein the at least two amino acids that are connected by the hydrocarbon covalent cross-link are positioned at i,i+4 or at i,i+7.

8. The method of claim 1, wherein at least one amino acid that is connected by the hydrocarbon covalent cross-link comprises an alpha-methyl, alpha-alkenyl amino acid.

9. The method of claim 1, wherein the hydrocarbon covalent cross-link spans from one to two turns on the alpha-helix.

10. A method for synthesizing a peptide comprising a cross-link, the method comprising:
   (a) synthesizing an amino acid sequence, wherein the amino acid sequence comprises a first amino acid comprising a first moiety and a second amino acid comprising a second moiety, and wherein the first and second moieties are reactive toward one another in the presence of a catalyst; and
   (b) reacting the amino acid sequence under conditions sufficient to promote a reaction between the first and second moieties toward each other in the presence of the catalyst, thereby resulting in formation of the cross-link in the peptide; wherein the peptide comprises a stabilized alpha helix and can disrupt binding of a first protein to a second protein; wherein the first protein is a native protein; the second protein is another native protein; the second protein comprises a helix acceptor; and the first protein binds the helix acceptor of the second protein.

11. The method of claim 10, wherein the cross-link spans from one to two turns on the alpha-helix.

12. The method of claim 10, wherein the cross-link comprises a carbon-carbon double bond.

13. The method of claim 10, wherein the peptide is stabilized in comparison to a corresponding uncross-linked peptide.

14. The method of claim 10, wherein the second protein is a natural protein.

15. The method of claim 10, wherein the peptide comprises a binding site of a donor helix of the first protein.

16. The method of claim 10, wherein at least one amino acid in the amino acid sequence is an alpha-allyl amino acid.

17. The method of claim 10, wherein the cross-link stabilizes an alpha-helix of the peptide.

18. The method of claim 1, wherein the peptide is stabilized in comparison to a corresponding uncross-linked peptide.

* * * * *

UNITED STATES PATENT AND TRADEMARK OFFICE
CERTIFICATE OF CORRECTION

| | | |
|---|---|---|
| PATENT NO. | : 10,487,110 B2 | Page 1 of 1 |
| APPLICATION NO. | : 15/917560 | |
| DATED | : November 26, 2019 | |
| INVENTOR(S) | : Gregory L. Verdine et al. | |

It is certified that error appears in the above-identified patent and that said Letters Patent is hereby corrected as shown below:

In the Specification

At Column 1, Lines 30-33, the sentence:
"This invention was made with government support under GM51330 awarded by the National Institutes of Health. The government has certain rights in the invention."
Should be changed to:
-- This invention was made with government support under GM051330 awarded by the National Institutes of Health. The government has certain rights in this invention. --

Signed and Sealed this
Thirteenth Day of August, 2024

Katherine Kelly Vidal
*Director of the United States Patent and Trademark Office*

SEQUENCE LISTING

<160> NUMBER OF SEQ ID NOS: 12

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Glu Trp Ala Glu Thr Ala Ala Ala Lys Phe Leu Ala Ala His Ala
1               5                   10                  15

-continued

```
<210> SEQ ID NO 2
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Unnatural amino acid
<220> FEATURE:
<221> NAME/KEY: MISC_FEATURE
<222> LOCATION: (12)..(12)
<223> OTHER INFORMATION: Unnatural amino acid

<400> SEQUENCE: 2

Glu Trp Ala Glu Xaa Ala Ala Ala Lys Phe Leu Xaa Ala His Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Unnatural amino acid
<220> FEATURE:
<221> NAME/KEY: MISC_FEATURE
<222> LOCATION: (12)..(12)
<223> OTHER INFORMATION: Unnatural amino acid

<400> SEQUENCE: 3

Glu Trp Ala Glu Thr Ala Ala Xaa Lys Phe Leu Xaa Ala His Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Unnatural amino acid
<220> FEATURE:
<221> NAME/KEY: MISC_FEATURE
<222> LOCATION: (8)..(8)
<223> OTHER INFORMATION: Unnatural amino acid
<220> FEATURE:
<221> NAME/KEY: MISC_FEATURE
<222> LOCATION: (15)..(15)
<223> OTHER INFORMATION: Unnatural amino acid

<400> SEQUENCE: 4

Xaa Trp Ala Glu Thr Ala Ala Xaa Lys Phe Leu Ala Ala His Xaa
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Gly Gln Val Gly Arg Gln Leu Ala Ile Ile Gly Asp Asp Ile Asn Arg
1               5                   10                  15
```

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Unnatural amino acid
<220> FEATURE:
<221> NAME/KEY: MISC_FEATURE
<222> LOCATION: (9)..(9)
<223> OTHER INFORMATION: Unnatural amino acid

<400> SEQUENCE: 6

Gly Gln Val Gly Xaa Gln Leu Ala Xaa Ile Gly Asp Asp Ile Asn Arg
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Unnatural amino acid
<220> FEATURE:
<221> NAME/KEY: MISC_FEATURE
<222> LOCATION: (13)..(13)
<223> OTHER INFORMATION: Unnatural amino acid

<400> SEQUENCE: 7

Gly Gln Val Gly Arg Gln Leu Ala Xaa Ile Gly Asp Xaa Ile Asn Arg
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Unnatural amino acid
<220> FEATURE:
<221> NAME/KEY: MISC_FEATURE
<222> LOCATION: (13)..(13)
<223> OTHER INFORMATION: Unnatural amino acid

<400> SEQUENCE: 8

Gly Gln Val Gly Arg Xaa Leu Ala Ile Ile Gly Asp Xaa Ile Asn Arg
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Unnatural amino acid
<220> FEATURE:
<221> NAME/KEY: MISC_FEATURE
<222> LOCATION: (12)..(12)
<223> OTHER INFORMATION: Unnatural amino acid

```
<400> SEQUENCE: 9

Gly Gln Val Gly Xaa Gln Leu Ala Ile Ile Gly Xaa Asp Ile Asn Arg
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Leu Ser Gln Glu Thr Phe Ser Asp Leu Trp Lys Leu Leu Pro Glu Asn
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Unnatural amino acid
<220> FEATURE:
<221> NAME/KEY: MISC_FEATURE
<222> LOCATION: (12)..(12)
<223> OTHER INFORMATION: Unnatural amino acid

<400> SEQUENCE: 11

Leu Ser Gln Glu Xaa Phe Ser Asp Leu Trp Lys Xaa Leu Pro Glu Asn
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Unnatural amino acid
<220> FEATURE:
<221> NAME/KEY: MISC_FEATURE
<222> LOCATION: (11)..(11)
<223> OTHER INFORMATION: Unnatural amino acid

<400> SEQUENCE: 12

Leu Ser Gln Xaa Thr Phe Ser Asp Leu Trp Xaa Leu Leu Pro Glu Asn
1               5                   10                  15
```